United States Patent
Spencer et al.

(10) Patent No.: US 12,053,260 B2
(45) Date of Patent: Aug. 6, 2024

(54) CATHETER-BASED OFF-AXIS OPTICAL COHERENCE TOMOGRAPHY IMAGING SYSTEM

(71) Applicant: Avinger, Inc., Redwood City, CA (US)

(72) Inventors: Maegan K. Spencer, Emerald Hills, CA (US); Christopher B. White, San Jose, CA (US); Charles W. McNall, Cottonwood Heights, UT (US); Dennis W. Jackson, San Francisco, CA (US); Michael Zung, San Carlos, CA (US); Nicholas J. Spinelli, San Carlos, CA (US); Benjamin Ngo, San Jose, CA (US); Evangeline Lumabas, San Jose, CA (US); Kin F. Chan, Los Gatos, CA (US); John F. Black, Irmo, SC (US); Michael H. Rosenthal, Menlo Park, CA (US); John B. Simpson, Woodside, CA (US)

(73) Assignee: Avinger, Inc., Redwood City, CA (US)

( * ) Notice: Subject to any disclaimer, the term of this patent is extended or adjusted under 35 U.S.C. 154(b) by 63 days.

(21) Appl. No.: 16/943,446

(22) Filed: Jul. 30, 2020

(65) Prior Publication Data
US 2021/0177262 A1 Jun. 17, 2021

Related U.S. Application Data

(63) Continuation of application No. 13/939,161, filed on Jul. 10, 2013, now Pat. No. 10,729,326, which is a
(Continued)

(51) Int. Cl.
*A61B 5/06* (2006.01)
*A61B 5/00* (2006.01)
*A61B 5/02* (2006.01)

(52) U.S. Cl.
CPC .......... *A61B 5/0066* (2013.01); *A61B 5/0062* (2013.01); *A61B 5/0073* (2013.01);
(Continued)

(58) Field of Classification Search
CPC ... A61B 5/0062; A61B 5/0066; A61B 5/0073; A61B 5/0084; A61B 5/02007; A61B 5/6852; A61B 5/7257
See application file for complete search history.

(56) References Cited

U.S. PATENT DOCUMENTS

| 3,367,727 A | 2/1968 | Ward et al. |
| 3,908,637 A | 9/1975 | Doroshow |

(Continued)

FOREIGN PATENT DOCUMENTS

| CN | 1875242 A | 12/2006 |
| CN | 1947652 A | 4/2007 |

(Continued)

OTHER PUBLICATIONS

Patel et al.; U.S. Appl. No. 17/347,419 entitled "Micro-molded anamorphic reflector lens for image guided therapeutic/diagnostic catheters," filed Jun. 14, 2021.
(Continued)

*Primary Examiner* — Katherine L Fernandez
(74) *Attorney, Agent, or Firm* — Shay Glenn LLP

(57) ABSTRACT

A system for imaging a body lumen includes a controller and a display. The controller is configured to connect to a proximal end of a catheter having an optical fiber extending along the length of an elongate catheter body. The controller is further configured to rotate a distal end of the optical fiber from a location near a proximal end of the elongate catheter body, acquire optical coherence tomography (OCT) images using the optical fiber as the distal end of the optical fiber rotates, and determine a rotational lag of the distal end of the
(Continued)

optical fiber. The display is configured to display one or more OCT images corrected for the rotational lag.

19 Claims, 34 Drawing Sheets

Related U.S. Application Data continuation of application No. 12/829,267, filed on Jul. 1, 2010, now Pat. No. 9,125,562.

(60) Provisional application No. 61/258,100, filed on Nov. 4, 2009, provisional application No. 61/244,408, filed on Sep. 21, 2009, provisional application No. 61/222,238, filed on Jul. 1, 2009.

(52) U.S. Cl.
CPC ........ *A61B 5/0084* (2013.01); *A61B 5/02007* (2013.01); *A61B 5/6852* (2013.01); *A61B 5/7257* (2013.01)

(56) References Cited

U.S. PATENT DOCUMENTS

| | | |
|---|---|---|
| 4,178,935 A | 12/1979 | Gekhaman et al. |
| 4,487,206 A | 12/1984 | Aagard |
| 4,527,553 A | 7/1985 | Upsher |
| 4,552,554 A | 11/1985 | Gould et al. |
| 4,578,061 A | 3/1986 | Lemelson |
| 4,598,710 A | 7/1986 | Kleinberg et al. |
| 4,611,600 A | 9/1986 | Cohen |
| 4,621,353 A | 11/1986 | Hazel et al. |
| 4,639,091 A | 1/1987 | Huignard et al. |
| 4,651,753 A | 3/1987 | Lifton |
| 4,654,024 A | 3/1987 | Crittenden et al. |
| 4,681,106 A | 7/1987 | Kensey et al. |
| 4,686,982 A | 8/1987 | Nash |
| 4,691,708 A | 9/1987 | Kane |
| 4,729,763 A | 3/1988 | Henrie |
| 4,771,774 A | 9/1988 | Simpson et al. |
| 4,781,186 A | 11/1988 | Simpson et al. |
| 4,841,977 A | 6/1989 | Griffith et al. |
| 4,842,578 A | 6/1989 | Johnson et al. |
| 4,850,354 A | 7/1989 | McGurk-Burleson et al. |
| 4,857,046 A | 8/1989 | Stevens et al. |
| 4,920,961 A | 5/1990 | Grossi et al. |
| 4,926,858 A | 5/1990 | Gifford, III et al. |
| 5,000,185 A | 3/1991 | Yock |
| 5,018,529 A | 5/1991 | Tenerz et al. |
| 5,041,082 A | 8/1991 | Shiber |
| 5,047,040 A | 9/1991 | Simpson et al. |
| 5,085,662 A | 2/1992 | Willard |
| 5,099,850 A | 3/1992 | Matsui et al. |
| 5,178,153 A | 1/1993 | Einzig |
| 5,182,291 A | 1/1993 | Gubin et al. |
| 5,190,050 A | 3/1993 | Nitzsche |
| 5,192,291 A | 3/1993 | Pannek, Jr. |
| 5,217,479 A | 6/1993 | Shuler |
| 5,312,415 A | 5/1994 | Palermo |
| 5,312,425 A | 5/1994 | Evans et al. |
| 5,321,501 A | 6/1994 | Swanson et al. |
| 5,333,142 A | 7/1994 | Scheps |
| 5,358,472 A | 10/1994 | Vance et al. |
| 5,366,464 A | 11/1994 | Belknap |
| 5,372,601 A | 12/1994 | Lary |
| 5,383,460 A | 1/1995 | Jang et al. |
| 5,383,467 A | 1/1995 | Auer et al. |
| 5,425,273 A | 6/1995 | Chevalier |
| 5,425,371 A | 6/1995 | Mischenko |
| 5,429,136 A | 7/1995 | Milo et al. |
| 5,431,673 A | 7/1995 | Summers et al. |
| 5,437,284 A | 8/1995 | Trimble |
| 5,459,570 A | 10/1995 | Swanson et al. |
| 5,460,168 A | 10/1995 | Masubuchi et al. |
| 5,465,147 A | 11/1995 | Swanson |
| 5,507,725 A | 4/1996 | Savage et al. |
| 5,507,760 A | 4/1996 | Wynne et al. |
| 5,507,795 A | 4/1996 | Chiang et al. |
| 5,517,998 A | 5/1996 | Madison |
| 5,529,580 A | 6/1996 | Kusunoki et al. |
| 5,556,405 A | 9/1996 | Lary |
| 5,607,394 A | 3/1997 | Andersen et al. |
| 5,620,426 A | 4/1997 | Braithwaite |
| 5,632,754 A | 5/1997 | Farley et al. |
| 5,632,755 A | 5/1997 | Nordgren et al. |
| 5,674,232 A | 10/1997 | Halliburton |
| 5,676,012 A | 10/1997 | Ceriale |
| 5,681,336 A | 10/1997 | Clement et al. |
| 5,690,634 A | 11/1997 | Muller et al. |
| 5,722,403 A | 3/1998 | McGee et al. |
| 5,728,148 A | 3/1998 | Bostrom et al. |
| 5,749,846 A | 5/1998 | Edwards et al. |
| 5,795,295 A | 8/1998 | Hellmuth et al. |
| 5,807,339 A | 9/1998 | Bostrom et al. |
| 5,830,145 A | 11/1998 | Tenhoff |
| 5,836,957 A | 11/1998 | Schulz et al. |
| 5,843,050 A | 12/1998 | Jones et al. |
| 5,843,103 A | 12/1998 | Wulfman |
| 5,851,212 A | 12/1998 | Zirps et al. |
| 5,868,778 A | 2/1999 | Gershony et al. |
| 5,872,879 A | 2/1999 | Hamm |
| 5,904,651 A | 5/1999 | Swanson et al. |
| 5,907,425 A | 5/1999 | Dickensheets et al. |
| 5,935,075 A | 8/1999 | Casscells et al. |
| 5,938,602 A | 8/1999 | Lloyd |
| 5,938,671 A | 8/1999 | Katoh et al. |
| 5,951,482 A | 9/1999 | Winston et al. |
| 5,951,581 A | 9/1999 | Saadat et al. |
| 5,951,583 A | 9/1999 | Jensen et al. |
| 5,956,355 A | 9/1999 | Swanson et al. |
| 5,957,952 A | 9/1999 | Gershony et al. |
| 5,987,995 A | 11/1999 | Sawatari et al. |
| 5,997,558 A | 12/1999 | Nash |
| 6,001,112 A | 12/1999 | Taylor |
| 6,007,530 A | 12/1999 | Domhofer et al. |
| 6,010,449 A | 1/2000 | Selmon et al. |
| 6,013,072 A | 1/2000 | Winston et al. |
| 6,017,359 A | 1/2000 | Gershony et al. |
| 6,027,514 A | 2/2000 | Stine et al. |
| 6,032,673 A | 3/2000 | Savage et al. |
| 6,048,349 A | 4/2000 | Winston et al. |
| 6,080,170 A | 6/2000 | Nash et al. |
| 6,106,515 A | 8/2000 | Winston et al. |
| 6,110,164 A | 8/2000 | Vidlund |
| 6,120,515 A | 9/2000 | Rogers et al. |
| 6,120,516 A | 9/2000 | Selmon et al. |
| 6,134,002 A | 10/2000 | Stimson et al. |
| 6,134,003 A | 10/2000 | Tearney et al. |
| 6,152,938 A | 11/2000 | Curry |
| 6,152,951 A | 11/2000 | Hashimoto et al. |
| 6,160,826 A | 12/2000 | Swanson et al. |
| 6,175,669 B1 | 1/2001 | Colston et al. |
| 6,176,871 B1 | 1/2001 | Pathak et al. |
| 6,183,432 B1 | 2/2001 | Milo |
| 6,193,676 B1 | 2/2001 | Winston et al. |
| 6,206,898 B1 | 3/2001 | Honeycutt et al. |
| 6,228,076 B1 | 5/2001 | Winston et al. |
| 6,241,744 B1 | 6/2001 | Imran et al. |
| 6,283,957 B1 | 9/2001 | Hashimoto et al. |
| 6,285,903 B1 | 9/2001 | Rosenthal et al. |
| 6,290,668 B1 | 9/2001 | Gregory et al. |
| 6,294,775 B1 | 9/2001 | Seibel et al. |
| 6,299,622 B1 | 10/2001 | Snow et al. |
| 6,307,985 B1 | 10/2001 | Murakami et al. |
| 6,375,615 B1 | 4/2002 | Flaherty et al. |
| 6,402,719 B1 | 6/2002 | Ponzi et al. |
| 6,416,527 B1 | 7/2002 | Berg et al. |
| 6,445,939 B1 | 9/2002 | Swanson et al. |
| 6,445,944 B1 | 9/2002 | Ostrovsky |
| 6,447,525 B2 | 9/2002 | Follmer et al. |
| 6,451,036 B1 | 9/2002 | Heitzmann et al. |
| 6,454,717 B1 | 9/2002 | Pantages et al. |

(56) References Cited

U.S. PATENT DOCUMENTS

| | | |
|---|---|---|
| 6,454,779 B1 | 9/2002 | Taylor |
| 6,482,216 B1 | 11/2002 | Hiblar et al. |
| 6,482,217 B1 | 11/2002 | Pintor et al. |
| 6,485,413 B1 | 11/2002 | Boppart et al. |
| 6,497,649 B2 | 12/2002 | Parker et al. |
| 6,501,551 B1 | 12/2002 | Tearney et al. |
| 6,503,261 B1 | 1/2003 | Bruneau et al. |
| 6,511,458 B2 | 1/2003 | Milo et al. |
| 6,517,528 B1 | 2/2003 | Pantages et al. |
| 6,542,665 B2 | 4/2003 | Reed et al. |
| 6,544,230 B1 | 4/2003 | Flaherty et al. |
| 6,546,272 B1 | 4/2003 | MacKinnon et al. |
| 6,551,302 B1 | 4/2003 | Rosinko et al. |
| 6,563,105 B2 | 5/2003 | Seibel et al. |
| 6,564,087 B1 | 5/2003 | Pitris et al. |
| 6,565,588 B1 | 5/2003 | Clement et al. |
| 6,572,563 B2 | 6/2003 | Ouchi et al. |
| 6,572,643 B1 | 6/2003 | Gharibadeh |
| 6,575,995 B1 | 6/2003 | Huter et al. |
| 6,579,298 B1 | 6/2003 | Bruneau et al. |
| 6,599,296 B1 | 7/2003 | Gillick et al. |
| 6,615,071 B1 | 9/2003 | Casscells, III et al. |
| 6,629,953 B1 | 10/2003 | Boyd |
| 6,638,233 B2 | 10/2003 | Corvi et al. |
| 6,645,217 B1 | 11/2003 | MacKinnon et al. |
| 6,657,727 B1 | 12/2003 | Izatt et al. |
| 6,666,874 B2 | 12/2003 | Heitzmann et al. |
| 6,687,010 B1 | 2/2004 | Horii |
| 6,728,571 B1 | 4/2004 | Barbato |
| D489,973 S | 5/2004 | Root et al. |
| 6,730,063 B2 | 5/2004 | Delaney et al. |
| 6,758,854 B1 | 7/2004 | Butler et al. |
| 6,760,112 B2 | 7/2004 | Reed et al. |
| 6,800,085 B2 | 10/2004 | Selmon et al. |
| 6,818,001 B2 | 11/2004 | Wulfman et al. |
| 6,824,550 B1 | 11/2004 | Noriega et al. |
| 6,830,577 B2 | 12/2004 | Nash et al. |
| 6,845,190 B1 | 1/2005 | Smithwick et al. |
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,682,319 B2 | 3/2010 | Martin et al. |
| 7,706,863 B2 | 4/2010 | Imanishi et al. |
| 7,728,985 B2 | 6/2010 | Feldchtein et al. |
| 7,729,745 B2 | 6/2010 | Maschke |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,002,763 B2 | 8/2011 | Berthiaume et al. |
| 8,059,274 B2 | 11/2011 | Splinter |
| 8,062,316 B2 | 11/2011 | Patel et al. |
| 8,068,921 B2 | 11/2011 | Prakash et al. |
| 8,313,493 B2 | 11/2012 | Fisher |
| 8,361,097 B2 | 1/2013 | Patel et al. |
| 8,548,571 B2 | 10/2013 | He et al. |
| 8,548,603 B2 | 10/2013 | Swoyer et al. |
| 8,632,557 B2 | 1/2014 | Thatcher et al. |
| 8,644,913 B2 | 2/2014 | Simpson et al. |
| 8,647,335 B2 | 2/2014 | Markus |
| 8,696,695 B2 | 4/2014 | Patel et al. |
| 8,911,459 B2 | 12/2014 | Simpson et al. |
| 9,119,662 B2 | 9/2015 | Moberg |
| 9,125,562 B2 | 9/2015 | Spencer et al. |
| 9,333,007 B2 | 5/2016 | Escudero et al. |
| 9,345,398 B2 | 5/2016 | Tachibana et al. |
| 9,345,406 B2 | 5/2016 | Spencer et al. |
| 9,345,510 B2 | 5/2016 | Patel et al. |
| 9,498,247 B2 | 11/2016 | Patel et al. |
| 9,498,600 B2 | 11/2016 | Rosenthal et al. |
| 9,557,156 B2 | 1/2017 | Kankaria |
| 9,572,492 B2 | 2/2017 | Simpson et al. |
| 9,592,075 B2 | 3/2017 | Simpson et al. |
| 9,642,646 B2 | 5/2017 | Patel et al. |
| 9,788,790 B2 | 10/2017 | Black et al. |
| 9,854,979 B2 | 1/2018 | Smith et al. |
| 9,918,734 B2 | 3/2018 | Patel et al. |
| 9,949,754 B2 | 4/2018 | Newhauser et al. |
| 10,052,125 B2 | 8/2018 | Rosenthal et al. |
| 10,130,386 B2 | 11/2018 | Simpson et al. |
| 10,244,934 B2 | 4/2019 | Tachibana et al. |
| 10,342,491 B2 | 7/2019 | Black et al. |
| 10,349,974 B2 | 7/2019 | Patel et al. |
| 10,357,277 B2 | 7/2019 | Patel et al. |
| 10,363,062 B2 | 7/2019 | Spencer et al. |
| 10,470,795 B2 | 11/2019 | Patel et al. |
| 10,548,478 B2 | 2/2020 | Simpson et al. |
| 10,568,520 B2 | 2/2020 | Patel et al. |
| 10,568,655 B2 | 2/2020 | Simpson et al. |
| 10,722,121 B2 | 7/2020 | Smith et al. |
| 10,729,326 B2 | 8/2020 | Spencer et al. |
| 10,806,484 B2 | 10/2020 | Simpson et al. |
| 10,860,484 B2 | 10/2020 | Simpson et al. |
| 10,869,685 B2 | 12/2020 | Patel et al. |
| 2001/0005788 A1 | 6/2001 | McGuckin, Jr. |
| 2001/0020126 A1 | 9/2001 | Swanson et al. |
| 2002/0019644 A1 | 2/2002 | Hastings et al. |
| 2002/0072706 A1 | 6/2002 | Hiblar et al. |
| 2002/0082585 A1 | 6/2002 | Carroll et al. |
| 2002/0082626 A1 | 6/2002 | Donohoe et al. |
| 2002/0097400 A1 | 7/2002 | Jung et al. |
| 2002/0111548 A1 | 8/2002 | Swanson et al. |
| 2002/0115931 A1 | 8/2002 | Strauss et al. |
| 2002/0138091 A1 | 9/2002 | Pflueger |
| 2002/0147459 A1 | 10/2002 | Bashiri et al. |
| 2002/0158547 A1 | 10/2002 | Wood |

(56) References Cited

U.S. PATENT DOCUMENTS

| | | | |
|---|---|---|---|
| 2002/0198457 A1* | 12/2002 | Tearney | A61B 5/0084 356/479 |
| 2003/0002038 A1 | 1/2003 | Mawatari | |
| 2003/0028100 A1 | 2/2003 | Tearney et al. | |
| 2003/0032880 A1 | 2/2003 | Moore | |
| 2003/0045835 A1 | 3/2003 | Anderson et al. | |
| 2003/0095248 A1 | 5/2003 | Frot | |
| 2003/0097044 A1 | 5/2003 | Rovegno | |
| 2003/0114875 A1 | 6/2003 | Sjostrom | |
| 2003/0120150 A1 | 6/2003 | Govari | |
| 2003/0120295 A1 | 6/2003 | Simpson et al. | |
| 2003/0125756 A1 | 7/2003 | Shturman et al. | |
| 2003/0125757 A1 | 7/2003 | Patel et al. | |
| 2003/0125758 A1 | 7/2003 | Simpson et al. | |
| 2003/0139751 A1 | 7/2003 | Evans et al. | |
| 2003/0181855 A1 | 9/2003 | Simpson et al. | |
| 2004/0002650 A1 | 1/2004 | Mandrusov et al. | |
| 2004/0039371 A1 | 2/2004 | Tockman et al. | |
| 2004/0057667 A1 | 3/2004 | Yamada et al. | |
| 2004/0059257 A1 | 3/2004 | Gaber | |
| 2004/0082850 A1 | 4/2004 | Bonner et al. | |
| 2004/0092915 A1 | 5/2004 | Levatter | |
| 2004/0093001 A1 | 5/2004 | Hamada | |
| 2004/0147934 A1 | 7/2004 | Klester | |
| 2004/0167553 A1* | 8/2004 | Simpson | A61B 1/3137 606/159 |
| 2004/0167554 A1 | 8/2004 | Simpson et al. | |
| 2004/0181249 A1 | 9/2004 | Torrance et al. | |
| 2004/0186368 A1 | 9/2004 | Ramzipoor et al. | |
| 2004/0193140 A1 | 9/2004 | Griffin et al. | |
| 2004/0202418 A1 | 10/2004 | Ghiron et al. | |
| 2004/0220519 A1 | 11/2004 | Wulfman et al. | |
| 2004/0230212 A1 | 11/2004 | Wulfman | |
| 2004/0230213 A1 | 11/2004 | Wulfman et al. | |
| 2004/0236312 A1 | 11/2004 | Nistal et al. | |
| 2004/0243162 A1 | 12/2004 | Wulfman et al. | |
| 2004/0254599 A1 | 12/2004 | Lipoma et al. | |
| 2004/0260236 A1 | 12/2004 | Manning et al. | |
| 2005/0020925 A1 | 1/2005 | Kleen et al. | |
| 2005/0027199 A1 | 2/2005 | Clarke | |
| 2005/0043614 A1 | 2/2005 | Huizenga et al. | |
| 2005/0054947 A1 | 3/2005 | Goldenberg | |
| 2005/0075660 A1 | 4/2005 | Chu et al. | |
| 2005/0085708 A1 | 4/2005 | Fauver et al. | |
| 2005/0085721 A1 | 4/2005 | Fauver et al. | |
| 2005/0105097 A1 | 5/2005 | Fang-Yen et al. | |
| 2005/0141843 A1 | 6/2005 | Warden et al. | |
| 2005/0149096 A1 | 7/2005 | Hilal et al. | |
| 2005/0154407 A1 | 7/2005 | Simpson | |
| 2005/0159712 A1 | 7/2005 | Andersen | |
| 2005/0159731 A1 | 7/2005 | Lee | |
| 2005/0171478 A1 | 8/2005 | Selmon et al. | |
| 2005/0177068 A1 | 8/2005 | Simpson | |
| 2005/0182295 A1 | 8/2005 | Soper et al. | |
| 2005/0187571 A1 | 8/2005 | Maschke | |
| 2005/0192496 A1 | 9/2005 | Maschke | |
| 2005/0197623 A1 | 9/2005 | Leeflang et al. | |
| 2005/0201662 A1 | 9/2005 | Petersen et al. | |
| 2005/0203553 A1 | 9/2005 | Maschke | |
| 2005/0222519 A1 | 10/2005 | Simpson | |
| 2005/0222663 A1 | 10/2005 | Simpson et al. | |
| 2005/0251116 A1 | 11/2005 | Steinke et al. | |
| 2006/0011820 A1 | 1/2006 | Chow-Shing et al. | |
| 2006/0032508 A1 | 2/2006 | Simpson | |
| 2006/0046235 A1 | 3/2006 | Alexander | |
| 2006/0049587 A1 | 3/2006 | Cornwell | |
| 2006/0064009 A1 | 3/2006 | Webler et al. | |
| 2006/0084911 A1 | 4/2006 | Belef et al. | |
| 2006/0109478 A1 | 5/2006 | Tearney et al. | |
| 2006/0135870 A1 | 6/2006 | Webler | |
| 2006/0173475 A1 | 8/2006 | Lafontaine et al. | |
| 2006/0229646 A1 | 10/2006 | Sparks | |
| 2006/0229659 A1 | 10/2006 | Gifford et al. | |
| 2006/0235262 A1 | 10/2006 | Arnal et al. | |
| 2006/0235366 A1 | 10/2006 | Simpson | |
| 2006/0236019 A1 | 10/2006 | Solto et al. | |
| 2006/0239982 A1 | 10/2006 | Simpson | |
| 2006/0241503 A1 | 10/2006 | Schmitt et al. | |
| 2006/0244973 A1 | 11/2006 | Yun et al. | |
| 2006/0252993 A1 | 11/2006 | Freed et al. | |
| 2006/0264741 A1 | 11/2006 | Prince | |
| 2006/0264743 A1 | 11/2006 | Kleen et al. | |
| 2006/0264907 A1 | 11/2006 | Eskridge et al. | |
| 2007/0010840 A1 | 1/2007 | Rosenthal et al. | |
| 2007/0015969 A1 | 1/2007 | Feldman et al. | |
| 2007/0015979 A1 | 1/2007 | Redel | |
| 2007/0035855 A1 | 2/2007 | Dickensheets | |
| 2007/0038061 A1 | 2/2007 | Huennekens et al. | |
| 2007/0038125 A1 | 2/2007 | Kleen et al. | |
| 2007/0038173 A1 | 2/2007 | Simpson | |
| 2007/0050019 A1 | 3/2007 | Hyde | |
| 2007/0078469 A1 | 4/2007 | Soito et al. | |
| 2007/0078500 A1 | 4/2007 | Ryan et al. | |
| 2007/0081166 A1 | 4/2007 | Brown et al. | |
| 2007/0088230 A1 | 4/2007 | Terashi et al. | |
| 2007/0106155 A1* | 5/2007 | Goodnow | A61B 8/5276 600/437 |
| 2007/0135712 A1 | 6/2007 | Maschke | |
| 2007/0167710 A1 | 7/2007 | Unal et al. | |
| 2007/0196926 A1 | 8/2007 | Soito et al. | |
| 2007/0213618 A1 | 9/2007 | Li et al. | |
| 2007/0219484 A1 | 9/2007 | Straub | |
| 2007/0250080 A1 | 10/2007 | Jones et al. | |
| 2007/0255252 A1 | 11/2007 | Mehta | |
| 2007/0270647 A1 | 11/2007 | Nahen et al. | |
| 2007/0276419 A1 | 11/2007 | Rosenthal | |
| 2007/0288036 A1 | 12/2007 | Seshadri | |
| 2007/0299309 A1 | 12/2007 | Seibel et al. | |
| 2008/0004643 A1 | 1/2008 | To et al. | |
| 2008/0004644 A1 | 1/2008 | To et al. | |
| 2008/0004645 A1 | 1/2008 | To et al. | |
| 2008/0004646 A1 | 1/2008 | To et al. | |
| 2008/0015491 A1 | 1/2008 | Bei et al. | |
| 2008/0015618 A1 | 1/2008 | Sonnenschein et al. | |
| 2008/0027334 A1 | 1/2008 | Langston | |
| 2008/0033396 A1 | 2/2008 | Danek et al. | |
| 2008/0045986 A1 | 2/2008 | To et al. | |
| 2008/0049234 A1 | 2/2008 | Seitz | |
| 2008/0058629 A1 | 3/2008 | Seibel et al. | |
| 2008/0065124 A1 | 3/2008 | Olson | |
| 2008/0065125 A1 | 3/2008 | Olson | |
| 2008/0065205 A1 | 3/2008 | Nguyen et al. | |
| 2008/0095421 A1 | 4/2008 | Sun et al. | |
| 2008/0103439 A1 | 5/2008 | Torrance et al. | |
| 2008/0103446 A1 | 5/2008 | Torrance et al. | |
| 2008/0103516 A1 | 5/2008 | Wulfman et al. | |
| 2008/0132929 A1 | 6/2008 | O'Sullivan et al. | |
| 2008/0139897 A1 | 6/2008 | Ainsworth et al. | |
| 2008/0146942 A1 | 6/2008 | Dala-Krishna | |
| 2008/0147000 A1 | 6/2008 | Seibel et al. | |
| 2008/0154293 A1 | 6/2008 | Taylor et al. | |
| 2008/0154296 A1 | 6/2008 | Taylor et al. | |
| 2008/0177138 A1 | 7/2008 | Courtney et al. | |
| 2008/0186501 A1 | 8/2008 | Xie | |
| 2008/0207996 A1 | 8/2008 | Tsai | |
| 2008/0221388 A1 | 9/2008 | Seibel et al. | |
| 2008/0228033 A1 | 9/2008 | Tumlinson et al. | |
| 2008/0243030 A1 | 10/2008 | Seibel et al. | |
| 2008/0243031 A1 | 10/2008 | Seibel et al. | |
| 2008/0262312 A1 | 10/2008 | Carroll et al. | |
| 2008/0275485 A1 | 11/2008 | Bonnette et al. | |
| 2008/0287795 A1 | 11/2008 | Klingensmith et al. | |
| 2009/0018393 A1* | 1/2009 | Dick | A61B 5/0066 600/109 |
| 2009/0018565 A1 | 1/2009 | To et al. | |
| 2009/0018566 A1 | 1/2009 | Escudero et al. | |
| 2009/0018567 A1 | 1/2009 | Escudero et al. | |
| 2009/0024084 A1 | 1/2009 | Khosla et al. | |
| 2009/0024085 A1 | 1/2009 | To et al. | |
| 2009/0024191 A1 | 1/2009 | Seibel et al. | |
| 2009/0028407 A1 | 1/2009 | Seibel et al. | |
| 2009/0028507 A1 | 1/2009 | Jones et al. | |
| 2009/0043191 A1 | 2/2009 | Castella et al. | |
| 2009/0073444 A1 | 3/2009 | Wang | |

(56) References Cited

U.S. PATENT DOCUMENTS

| | | | |
|---|---|---|---|
| 2009/0073455 A1* | 3/2009 | Onimura | A61B 5/6852 356/479 |
| 2009/0076447 A1 | 3/2009 | Casas et al. | |
| 2009/0093764 A1 | 4/2009 | Pfeffer et al. | |
| 2009/0099641 A1 | 4/2009 | Wu et al. | |
| 2009/0125019 A1 | 5/2009 | Douglass et al. | |
| 2009/0135280 A1 | 5/2009 | Johnston et al. | |
| 2009/0137893 A1 | 5/2009 | Seibel et al. | |
| 2009/0152664 A1 | 6/2009 | Tian et al. | |
| 2009/0185135 A1 | 7/2009 | Volk | |
| 2009/0196477 A1* | 8/2009 | Cense | G01B 9/02083 382/131 |
| 2009/0196554 A1 | 8/2009 | Irisawa | |
| 2009/0198125 A1 | 8/2009 | Nakabayashi et al. | |
| 2009/0208143 A1 | 8/2009 | Yoon et al. | |
| 2009/0216180 A1 | 8/2009 | Lee et al. | |
| 2009/0221904 A1 | 9/2009 | Shealy et al. | |
| 2009/0221920 A1 | 9/2009 | Boppart et al. | |
| 2009/0234220 A1* | 9/2009 | Maschke | A61B 90/98 604/523 |
| 2009/0235396 A1 | 9/2009 | Wang et al. | |
| 2009/0244485 A1 | 10/2009 | Walsh et al. | |
| 2009/0244547 A1* | 10/2009 | Ozawa | G01B 9/02091 356/511 |
| 2009/0264826 A1 | 10/2009 | Thompson | |
| 2009/0268159 A1* | 10/2009 | Xu | A61B 3/1233 351/246 |
| 2009/0275966 A1 | 11/2009 | Mitusina | |
| 2009/0284749 A1 | 11/2009 | Johnson et al. | |
| 2009/0292199 A1 | 11/2009 | Bielewicz et al. | |
| 2009/0306520 A1 | 12/2009 | Schmitt et al. | |
| 2009/0316116 A1* | 12/2009 | Melville | G03B 21/00 348/742 |
| 2009/0318862 A1 | 12/2009 | All et al. | |
| 2010/0004544 A1 | 1/2010 | Toida | |
| 2010/0021926 A1 | 1/2010 | Noordin | |
| 2010/0049225 A1 | 2/2010 | To et al. | |
| 2010/0080016 A1 | 4/2010 | Fukul et al. | |
| 2010/0082000 A1 | 4/2010 | Honeck et al. | |
| 2010/0125253 A1 | 5/2010 | Olson | |
| 2010/0130996 A1 | 5/2010 | Doud et al. | |
| 2010/0198081 A1* | 8/2010 | Hanlin | A61B 5/02007 600/478 |
| 2010/0217245 A1 | 8/2010 | Prescott | |
| 2010/0241147 A1 | 9/2010 | Maschke | |
| 2010/0253949 A1 | 10/2010 | Adler et al. | |
| 2010/0292539 A1 | 11/2010 | Lankenau et al. | |
| 2010/0292721 A1 | 11/2010 | Moberg | |
| 2010/0312263 A1 | 12/2010 | Moberg et al. | |
| 2010/0317973 A1 | 12/2010 | Nita | |
| 2010/0324472 A1 | 12/2010 | Wulfman | |
| 2011/0023617 A1 | 2/2011 | Yu et al. | |
| 2011/0028977 A1 | 2/2011 | Rauscher et al. | |
| 2011/0040238 A1 | 2/2011 | Wulfman et al. | |
| 2011/0058250 A1 | 3/2011 | Liu et al. | |
| 2011/0060186 A1 | 3/2011 | Tilson et al. | |
| 2011/0071401 A1 | 3/2011 | Hastings et al. | |
| 2011/0092955 A1 | 4/2011 | Purdy et al. | |
| 2011/0106004 A1 | 5/2011 | Eubanks et al. | |
| 2011/0118660 A1 | 5/2011 | Torrance et al. | |
| 2011/0130777 A1 | 6/2011 | Zhang et al. | |
| 2011/0144673 A1 | 6/2011 | Zhang et al. | |
| 2011/0201924 A1 | 8/2011 | Tearney et al. | |
| 2011/0208222 A1 | 8/2011 | Ljahnicky et al. | |
| 2011/0257478 A1 | 10/2011 | Kleiner et al. | |
| 2011/0264125 A1 | 10/2011 | Wilson et al. | |
| 2011/0270187 A1 | 11/2011 | Nelson | |
| 2011/0295148 A1 | 12/2011 | Destoumieux et al. | |
| 2011/0301625 A1 | 12/2011 | Mauch et al. | |
| 2011/0319905 A1 | 12/2011 | Palme et al. | |
| 2012/0002928 A1 | 1/2012 | Irisawa | |
| 2012/0004506 A1 | 1/2012 | Tearney et al. | |
| 2012/0238869 A1 | 9/2012 | Schmitt et al. | |
| 2012/0277730 A1 | 11/2012 | Salahich et al. | |
| 2013/0023865 A1* | 1/2013 | Steinke | A61B 5/0066 606/7 |
| 2013/0184549 A1 | 7/2013 | Avitall et al. | |
| 2013/0331819 A1 | 12/2013 | Rosenman et al. | |
| 2014/0005534 A1 | 1/2014 | He et al. | |
| 2015/0141816 A1 | 5/2015 | Gupta et al. | |
| 2015/0320975 A1 | 11/2015 | Simpson et al. | |
| 2016/0008025 A1 | 1/2016 | Gupta et al. | |
| 2016/0038030 A1 | 2/2016 | Smith et al. | |
| 2016/0144155 A1 | 5/2016 | Simpson et al. | |
| 2016/0262839 A1 | 9/2016 | Spencer et al. | |
| 2017/0238803 A1 | 8/2017 | Kankaria | |
| 2017/0238808 A1 | 8/2017 | Simpson et al. | |
| 2018/0042520 A1 | 2/2018 | Patel et al. | |
| 2018/0207417 A1 | 7/2018 | Zung et al. | |
| 2019/0021679 A1 | 1/2019 | Christensen | |
| 2019/0021760 A1 | 1/2019 | Newhauser et al. | |
| 2019/0029714 A1 | 1/2019 | Patel et al. | |
| 2019/0110809 A1 | 4/2019 | Rosenthal et al. | |
| 2019/0209206 A1 | 7/2019 | Patel et al. | |
| 2019/0313941 A1 | 10/2019 | Radjabi | |
| 2020/0029801 A1 | 1/2020 | Tachibana et al. | |
| 2020/0060718 A1 | 2/2020 | Patel et al. | |
| 2020/0069253 A1 | 3/2020 | Black et al. | |
| 2020/0069327 A1 | 3/2020 | Patel et al. | |
| 2020/0315654 A1 | 10/2020 | Patel et al. | |
| 2020/0323553 A1 | 10/2020 | Fernandez et al. | |
| 2021/0345903 A1 | 11/2021 | Patel et al. | |
| 2022/0039828 A1 | 2/2022 | Patel et al. | |
| 2022/0168011 A1 | 6/2022 | Patel et al. | |
| 2022/0183545 A1 | 6/2022 | Tachibana et al. | |
| 2022/0240860 A1 | 8/2022 | Black et al. | |
| 2022/0273336 A1 | 9/2022 | Fernandez et al. | |
| 2022/0273337 A1 | 9/2022 | Patel et al. | |
| 2022/0323099 A1 | 10/2022 | Patel et al. | |
| 2022/0346638 A1 | 11/2022 | Patel | |
| 2023/0225616 A1 | 7/2023 | Patel et al. | |
| 2024/0041491 A1 | 2/2024 | Patel | |
| 2024/0057942 A1 | 2/2024 | Black et al. | |

FOREIGN PATENT DOCUMENTS

| | | |
|---|---|---|
| CN | 101601581 A | 12/2009 |
| DE | 202006018883.5 U | 2/2007 |
| EP | 0347098 A2 | 12/1989 |
| EP | 0808638 A1 | 11/1997 |
| EP | 0845692 B1 | 11/2005 |
| EP | 1859732 A1 | 11/2007 |
| EP | 2090245 A1 | 8/2009 |
| EP | 2353526 B1 | 9/2013 |
| JP | S62-275425 A | 11/1987 |
| JP | 03502060 A | 2/1990 |
| JP | H05501065 A | 3/1993 |
| JP | 05103763 A | 4/1993 |
| JP | 06027343 A | 2/1994 |
| JP | H07184888 A | 7/1995 |
| JP | 07308393 A | 11/1995 |
| JP | 2002214127 A | 7/2002 |
| JP | 2004509695 A | 4/2004 |
| JP | 2004516073 A | 6/2004 |
| JP | 2005114473 A | 4/2005 |
| JP | 2005230550 A | 9/2005 |
| JP | 2005249704 A | 9/2005 |
| JP | 2005533533 A | 11/2005 |
| JP | 2008175698 A | 7/2006 |
| JP | 2006288775 A | 10/2006 |
| JP | 2006313158 A | 11/2006 |
| JP | 2006526790 A | 11/2006 |
| JP | 2006326157 A | 12/2006 |
| JP | 200783053 A | 4/2007 |
| JP | 200783057 A | 4/2007 |
| JP | 2007225349 A | 9/2007 |
| JP | 2007533361 A | 11/2007 |
| JP | 2008023627 | 2/2008 |
| JP | 2008128708 A | 6/2008 |
| JP | 2008145376 A | 6/2008 |
| JP | 2008183208 A | 8/2008 |
| JP | 2008253492 A | 10/2008 |
| JP | 200914751 A | 1/2009 |

(56) References Cited

FOREIGN PATENT DOCUMENTS

| | | |
|---|---|---|
| JP | 2009509690 A | 3/2009 |
| JP | 200978150 A | 4/2009 |
| JP | 2009066252 A | 4/2009 |
| JP | 2009201969 A | 9/2009 |
| JP | 2010042182 A | 2/2010 |
| JP | 2010518900 A | 6/2010 |
| JP | 2011521747 A | 7/2011 |
| JP | 2012533353 A | 12/2012 |
| JP | 2013512736 A | 4/2013 |
| JP | 2013/524930 A | 6/2013 |
| KR | 2007/0047221 A | 5/2007 |
| RU | 2185859 C2 | 7/2002 |
| RU | 2218191 C2 | 12/2003 |
| WO | WO91/17698 A1 | 11/1991 |
| WO | WO99/23958 A1 | 5/1999 |
| WO | WO00/54659 A1 | 9/2000 |
| WO | WO01/15609 A1 | 3/2001 |
| WO | WO01/76680 A1 | 10/2001 |
| WO | WO2006/133030 A2 | 12/2006 |
| WO | WO2008/005888 A2 | 1/2008 |
| WO | WO2008/029506 A1 | 3/2008 |
| WO | WO2008/042987 A2 | 4/2008 |
| WO | WO2008/051951 A1 | 5/2008 |
| WO | WO2008/065600 A2 | 6/2008 |
| WO | WO2008/086613 A1 | 7/2008 |
| WO | WO2008/087613 A2 | 7/2008 |
| WO | WO2008/151155 A2 | 12/2008 |
| WO | WO2009/005779 A1 | 1/2009 |
| WO | WO2009/006335 A1 | 1/2009 |
| WO | WO2009/009799 A1 | 1/2009 |
| WO | WO2009/009802 A1 | 1/2009 |
| WO | WO2009/023635 A1 | 2/2009 |
| WO | WO2009/024344 A1 | 2/2009 |
| WO | WO2009/094341 A2 | 7/2009 |
| WO | WO2009/140617 A2 | 11/2009 |
| WO | WO2009/148317 A1 | 12/2009 |
| WO | WO2010/039464 A1 | 4/2010 |
| WO | WO2010/056771 A1 | 5/2010 |
| WO | WO2011/044387 A2 | 4/2011 |
| WO | WO2011/062087 A1 | 5/2011 |
| WO | WO2022/192102 A1 | 9/2022 |

OTHER PUBLICATIONS

Gupta et al.; U.S. Appl. No. 17/445,648 entitled "Tissue collection device for catheter," filed Aug. 23, 2021.

Simpson et al.; U.S. Appl. No. 17/449,867 entitled "Occlusion-crossing devices, imaging, and atherectomy devices," filed Oct. 4, 2021.

Spencer et al.; U.S. Appl. No. 17/449,895 entitled "Occlusion-crossing devices, atherectomy devices, and imaging," filed Oct. 4, 2021.

Aziz et al.; Chronic total occlusions—a stiff challege requiring a major breakthrough: is there light at the end of the tunnel?; Heart; vol. 91; suppl. III; pp. 42-48; Jun. 2005.

Bayer Material Science: ; Snap-Fit Joints for Plastics; 26 pages; retrieved from the Internet: ( https://web.archive.org/web/20121119232733if_/http://fab.cba.mit.edu:80/classes/S62.12/people/vernelle.noel/Plastic_Snap_fit_design.pdf) on Sep. 26, 2018.

Choma et al.; Sensitivity advantage of swept source and fourier domain optical coherence tomography; Optics Express; 11(18); pp. 2183-2189; Sep. 8, 2003.

De Boer et al.; Improved signal-to-noise ratio in spectral-domain compared with time-domain optical coherence tomography; Optics Letters; 28(21); pp. 2067-2069; Nov. 2003.

Emkey et al.; Analysis and evaluation of graded-index fiber-lenses; Journal of Lightwave Technology; vol. LT-5; No. 9; pp. 1156-1164; Sep. 1987.

Gonzalo et al.; Optical coherence tomography patterns of stent restenosis; Am. Heart J.; 158(2); pp. 284-293; Aug. 2009.

Han et al.; In situ Frog Retina Imaging Using Common-Path OCT with a Gold-Coated Bare Fiber Probe; CFM6; San Jose, California; CLEO, May 4, 2008; 2 pages.

Leitgeb et al.; Performance of fourier domain vs time domain optical coherence tomography; Optics Express; 11(8); pp. 889-894; Apr. 21, 2003.

Linares et al.; Arbitrary single-mode coupling by tapered and nontapered grin fiber lenses; Applied Optics; vol. 29; No. 28; pp. 4003-4007; Oct. 1, 1990.

Muller et al.; Time-gated infrared fourier-domain optical coherence tomography; CFM5; San Jose, California; CLEO May 4, 2008; 2 pages.

Rollins et al.; Optimal interferometer designs for optical coherence tomography; Optics Letters; 24(21); pp. 1484-1486; Nov. 1999.

Schmitt et al.; A new rotational thrombectomy catheter: System design and first clinical experiences; Cardiovascular and Interventional Radiology; Springer-Verlag; 22(6); pp. 504-509; Nov. 1, 1999.

Sharma et al.; Common-path optical coherence tomography with side-viewing bare fiber probe for endoscopic optical coherence tomography; Rev. Sci. Instrum.; vol. 78; 113102; 5 pages; Nov. 6, 2007.

Sharma et al.; Optical coherence tomography based on an all-fiber autocorrelator using probe-end reflection as reference; CWJ13; San Francisco, California; CLEO May 16, 2004; 4 pages.

Stamper et al.; Plaque characterization with optical coherence tomography. Journal of the American College of Cardiology. 47(8); pp. 69-79; Apr. 18, 2006.

Suparno et al.; Light scattering with single-mode fiber collimators; Applied Optics; vol. 33; No. 30; pp. 7200-7205; Oct. 20, 1994.

Tanaka et al.; Challenges on the frontier of intracoronary imaging: atherosclerotic plaque macrophage measurement by optical coherence tomography; Journal of Biomedical Optics; 15(1); pp.(011104-1)-(011104-8); Jan.-Feb. 2010.

Wang et al.; Common-path endoscopic Fourier domain OCT with a reference Michelson interferometer; Proceedings of the SPIE; vol. 7566; pp. 75660L-75660L-7; Jan. 2010.

Patel et al.; U.S. Appl. No. 16/801,047 entitled "Micro-molded anamorphic reflector lens for image guided therapeutic/diagnostic catheters," filed Feb. 25, 2020.

Smith et al.; U.S. Appl. No. 16/941,310 entitled "Chronic total occlusion crossing devices with imaging," filed Jul. 28, 2020.

Patel et al.; U.S. Appl. No. 17/046,066 entitled "Occlusion-crossing devices," filed Oct. 8, 2020.

Simpson et al.; U.S. Appl. No. 17/075,548 entitled "Identification of elastic lamina to guide interventional therapy," filed Oct. 20, 2020.

Patel et al.; U.S. Appl. No. 17/455,655 entitled "Atherectomy catheter with shapeable distal tip," filed Nov. 18, 2021.

Merriam Webster; Proximal (Definition); 10 pages; retrieved from the internet (https://www.merriam-webster.com/dictionary/proximal) on Jun. 9, 2021.

Wikipedia; Hinge; 4 pages; retrieved from the internet (https://en.wikipedia.org/w/index.php?title=Hinge&oldid=479569345) on Jun. 9, 2021.

Smith et al.; U.S. Appl. No. 17/189,123 entitled "Optical pressure sensor assembly," filed Mar. 1, 2021.

Kankaria; U.S. Appl. No. 17/209,162 entitled "Optical coherence tomography with graded index fiber for biological imaging," filed Mar. 22, 2021.

Newhauser et al.; U.S. Appl. No. 17/209,168 entitled "Occlusion-crossing devices," filed Mar. 22, 2021.

Patel et al.; U.S. Appl. No. 17/816,673 entitled "Atherectomy catheter with serrated cutter," filed Aug. 1, 2022.

Rosenthal et al.; U.S. Appl. No. 18/337,852 entitled "Atherectomy catheter with laterally-displaceable tip," filed Jun. 20, 2023.

Patel et al.; U.S. Appl. No. 18/550,243 entitled "Occlusion-crossing devices," filed Sep. 12, 2023.

Smith et al.; U.S. Appl. No. 18/393,399 entitled "Chronic total occlusion crossing devices with imaging," filed Dec. 21, 2023.

Simpson et al.; U.S. Appl. No. 18/416,264 entitled "Occlusion-crossing devices, imaging, and atherectomy devices," filed Jan. 18, 2024.

Patel et al.; U.S. Appl. No. 18/439,575 entitled "High speed chronic total occlusion crossing devices," filed Feb. 12, 2024.

\* cited by examiner

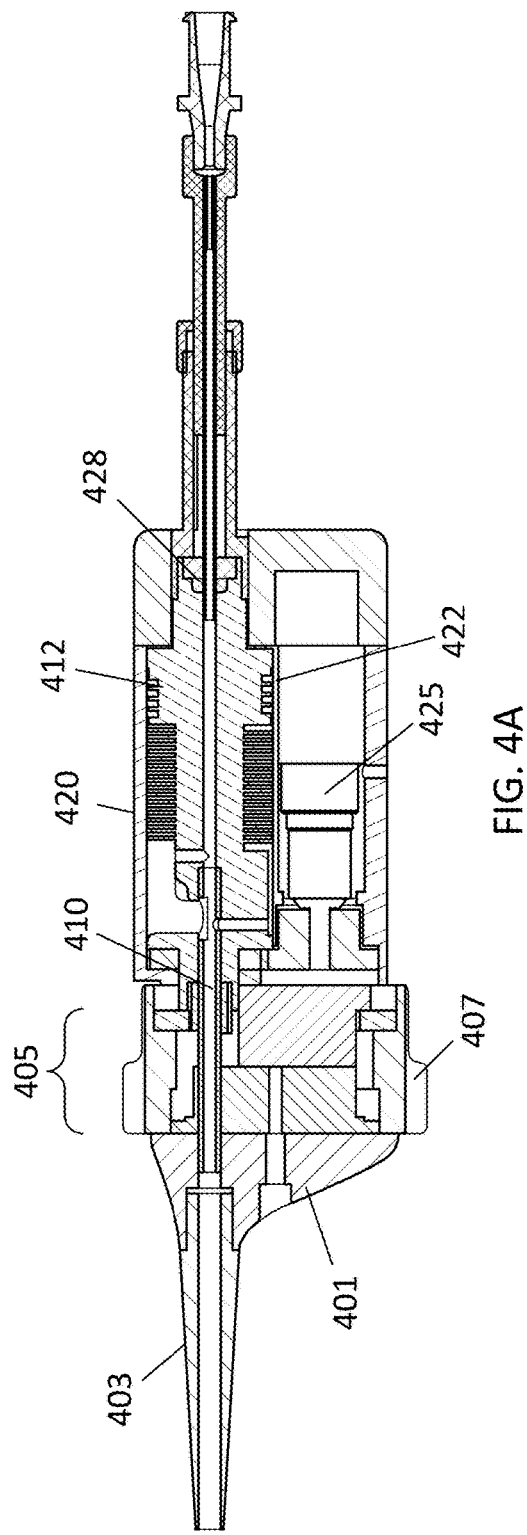
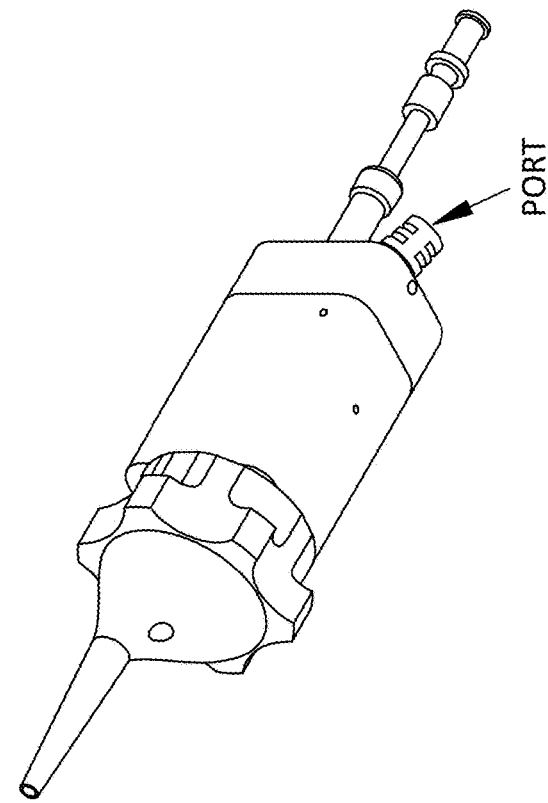
FIG. 4A
FIG. 4B
FIG. 4C

CATHETER-BASED OFF-AXIS OPTICAL COHERENCE TOMOGRAPHY IMAGING SYSTEM

CROSS REFERENCE TO RELATED APPLICATIONS

This application is a continuation of U.S. patent application Ser. No. 13/939,161, titled "CATHETER-BASED OFF-AXIS OPTICAL COHERENCE TOMOGRAPHY IMAGING SYSTEM," filed on Jul. 10, 2013, now U.S. Publication No. US-2013-0296695-A1, which is a continuation of U.S. patent application Ser. No. 12/829,267, titled "CATHETER-BASED OFF-AXIS OPTICAL COHERENCE TOMOGRAPHY IMAGING SYSTEM," filed on Jul. 1, 2010, now U.S. Pat. No. 9,125,562, which claims priority to U.S. Provisional Patent Application No. 61/222,238, titled "CATHETER FOR INTRALUMINAL CIRCUMFERENTIAL IMAGING WITH ROTATION ANGLE AND LONGITUDINAL POSITION ENCODING," filed on Jul. 1, 2009, U.S. Provisional Patent Application No. 61/244,408, titled "CATHETER-BASED OPTICAL COHERENCE TOMOGRAPHY IMAGING SYSTEM" and filed on Sep. 21, 2009 and U.S. Provisional patent application Ser. No. 61/258,100, titled "CATHETER PROXIMAL END EMBODIMENTS FOR INTRALUMINAL CIRCUMFERENTIAL IMAGING WITH ROTATION ANGLE AND LONGITUDINAL POSITION ENCODING" and filed on Nov. 4, 2009, each of which is herein incorporated by reference its entirety.

This application may also be related to pending U.S. patent application Ser. No. 12/790,703, titled "OPTICAL COHERENCE TOMOGRAPHY FOR BIOLOGICAL IMAGING," filed on May 28, 2010, Publication No. US-2010-0305452-A1 which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

Described herein are imaging catheters. In particular, OCT imaging catheters, systems, and methods of using them with an off-axis optical fiber are described herein.

BACKGROUND OF THE INVENTION

Visualization during minimally invasive surgical procedures has long been understood to enhance the performance and outcomes of surgical procedures. However, successful visualization, particularly visualization into a tissue volume, has proven elusive. One promising catheter-based visualization technology is optical coherence tomography (OCT). OCT has shown promise as an "ultrasound-like" optical visualization method, in which a thickness of the tissue volume may be imaged to reveal internal structures at relatively high resolution.

OCT may be particularly useful in conjunction with a catheter that may traverse tissues and body lumens and may, in some variations, be configured to modify or sample tissue in conjunction with the imaging or guided by the imaging. For example, an OCT imaging catheter may be configured as an atherectomy catheter. A significant body of scientific and clinical evidence supports atherectomy as a viable primary or adjunctive therapy prior to stenting for the treatment of occlusive coronary artery disease. Atherectomy offers a simple mechanical advantage over alternative therapies. By removing the majority of plaque mass (debulking) it creates a larger initial lumen and dramatically increases the compliance of the arterial wall. As a result, for example, stent deployment would be greatly enhanced following site preparation with atherectomy. There are advantages related to the arterial healing response. By removing the disease with minimal force applied to the vessel and reducing the plaque burden prior to stent placement, large gains in lumen size can be created with decreased vessel wall injury and limited elastic recoil. This has been shown to translate into better acute results and lower restenosis rates.

Physician practice is often to a treat target lesion as if it is composed of concentric disease even though intravascular diagnostic devices have consistently shown significantly eccentric lesions. This circumferential treatment approach virtually ensures that native arterial wall and potentially healthy vessel will be stressed, stretched or cut unnecessarily.

Currently available systems are poorly adapted for real-time imaging, particularly for use in catheters including atherectomy catheters. For example, much is already known about FORJ technology (Fiber Optic Rotating Junction), spinning mirrors, spinning prisms, and motors in the distal tips of catheters. However, such embodiments take up a lot of space, so much so that they may not be practical for use in conjunction with a therapeutic embodiment such as an atherectomy device.

It is generally desirable to reduce the crossing profile of the catheter to enable access to distal tortuous vessels in the heart or the periphery without collateral damage. The invention described here may achieve these aims. There are no large, expensive, fragile rotating junctions or rotating mechanisms in the catheter distal tip. The fiber is terminated in an adhesive that forms a single, unique, well-defined reference reflection with no complicating intermediate reflections. The drive shaft can have a small OD (0.012" demonstrated), minimizing the effect on crossing profile.

The devices described herein may form a circumferential view using the imaging catheter, allowing a true full circumferential field of view with a very small impact on crossing profile while preserving the ability to use common-path interferometry. Prior art devices (e.g., Lightlab™ ImageWire, MGH fiber optic rotating junctions, Cardiospectra (Milner)) generate full circumferential views inside a body lumen either by having a fiber rotating junction (e.g., http://www.princetel.com/product_forj.asp) between the OCT console and the catheter tip, with spinning of the optical fiber, by having a mechanism on the end of the catheter that rotates a mirror or prism, or by wagging the fiber in one or two axes or planes.

A FORJ necessarily introduces a break in the fiber. In this type of system, light goes from being confined in the core of the fiber to propagating in free space and is then re-imaged back into the fiber. See, e.g., Bouma (U.S. Pat. No. 7,382, 949). Two problems immediately ensue from this arrangement. First, the break in the fiber and the re-imaging optics create several surfaces with potentially very large return losses (back-reflections) compared to the usual OCT reference reflection. This makes the device difficult to use with common-path interferometry, as the interferometer will index off the first substantial reflection. One cannot simply make the reference reflection brighter than these surfaces, as (a) this would then create a reference reflection that could saturate the detector if it needed to be greater than, for example, 20 microWatts, and (b) the strong reflections present in the proximal optical path could still lead to artifacts in the OCT image, as these reflective surfaces would still be orders of magnitude brighter than the signal from the tissue. Second, the alignment of the two fiber cores has to be maintained to an exceptionally high tolerance, typically less than 0.5 microns of wobble as the device rotates. Such a high level of accuracy drives up the cost of the device significantly, which is something of particular concern in a single-use disposable device.

One attempted solution to the internal reflection problem in the FORJ is to have a rotating junction that incorporates index matching fluid between the fixed and rotating fiber cores. This solution is not really suitable for cost and complexity reasons as a component of a one-time-use disposable catheter. Incorporating the FORJ into the capital equipment complicates the design of the interface as this now has to be a sterilizable multi-use unit resistant to liquid and contaminant ingress. These requirements may be incompatible with the materials and assembly techniques used to make the FORJ.

Furthermore, a rotating mechanism on the distal tip significantly increases the crossing profile and complexity of the device. It is generally unsuitable for use with a single-use disposable device where costs must be minimized. In a device intended for small diameter body lumens, for example coronary arteries, the presence of a large diameter mechanism in the distal tip will define the maximum vessel size that can be safely treated. The mechanism may also increase the rigid length of the catheter, which will in turn restrict the vessel tortuosity into which the catheter may be safely inserted. This may preclude use of the device in the mid- or distal coronary arteries or in the distal peripheral vasculature, for example the dorsalis pedis.

The methods, devices and systems described herein allow intra-luminal common-path low-coherence interferometry with a contiguous fiber path while also allowing the creation of and updating of 360° circumferential views inside a vessel with angle and longitudinal encoding. Common-path interferometry is highly desirable for a catheter, as it eliminates the need for a separate reference arm and makes operation insensitive to manufacturing variations in catheter length. The devices, systems and methods described herein allow for creation of a >360° circumferential view as well as a 3-D reconstruction or rendition of the traversed tissue volume, without a break in fiber continuity. These methods, devices and system are particularly suitable for directional atherectomy or directional re-entry, as the imaging element can be steered towards a region of interest and allowed to dwell there so that the cut progression and depth can be monitored in real time.

There is a need for a method of forming a circumferential image in a lumen in a manner that permits the use of common-path interferometry and that has a minimal impact on crossing profile and work flow in the catheter lab. Common path interferometry eliminates the down-lead sensitivity that makes catheters for Michelson interferometry very costly to produce. This is because the catheter length has to be matched to the reference arm in the console to within a few microns or to within the adjustability of the reference arm. Common-path interferometry also allows the console to be placed an almost arbitrary distance from the patient and fluoroscopy equipment. The invention described here achieves these aims. The fiber is contiguous from console to distal tip, with no breaks to cause large back-reflections thereby permitting common path interferometry.

Furthermore, it would be very useful to provide catheter devices and methods of using them that permit the off-axis placement of the optical fiber used to form the OCT image. Off-axis placement of the fiber would allow the center (core) of the catheter to be used for passing guidewires, additional manipulators, tissue (including cut tissue), drive trains, or the like. However, optical fibers that are positioned off-axis within a catheter may be difficult to manipulate in the formation of a 360° image, since it may be necessary to rotate the entire catheter, rather than just the optical fiber, as is commonly done. Rotation of the entire catheter, including the off-axis optical fiber, relative to a proximate handle or control may result in tangling or binding of the optical fiber at the proximal location. This could ultimately lead to degradation of the image quality and a break in the workflow of the catheter lab environment while the optical fiber is untangled or managed during a surgical procedure.

The devices and systems described herein typically describe catheter-based, off-axis OCT systems that may address many of the needs and problems described above.

SUMMARY OF THE INVENTION

Described herein are catheters having off-axis optical fibers for OCT imaging, OCT imaging systems having off-axis optical fibers and methods of using OCT imaging catheters and systems.

The devices and systems described herein may include a catheter having a handle and a catheter body that is rotatable independently of the catheter body, and an optical fiber extending along the length of the catheter body while being radially displaced (off-axis) from the longitudinal axis (midline) of the catheter body. The optical fiber may be present in a channel.

For example, described herein are Optical Coherence Tomography (OCT) catheter devices for visualizing a body lumen by rotation of the catheter and an off-axis optical fiber within the catheter, the device comprising: a catheter body having an elongate proximal to distal length; an optical fiber extending the length of the catheter body along a path that is off-axis of the elongate length of the catheter body; a proximal handle rotationally coupled to the catheter body; and a fiber management pathway within the handle configured to allow the off-axis optical fiber to rotate with the catheter body, relative to the handle.

The catheter body may include a central lumen and/or any appropriate number of additional lumens, including off-axis (e.g., axially displaced from the central lumen) lumens. In some variations, the catheter body includes a channel for the optical fiber. The channel may be located off-axis of the elongate length of the catheter body.

The catheter devices described herein may also include a rotation knob that is coupled to the catheter body and is configured to rotate the catheter body when manipulated. The handle may comprise a limiter configured to define the allowable number of rotations of the catheter body. The limiter may be configured to restrict rotation of the catheter body to any number of full or fractional revolutions, with the typical range in constructed embodiments being between about two to six full rotations. The limiter may be configured to prevent rotation of the catheter body more than four full rotations. This may be useful, for example, in a monorail-type (Rapid exchange) configuration of a catheter, in which it may prevent the guide wire from getting wrapped around the catheter torque shaft and forming a potentially destructive reaming surface. The limiter may be configured to prevent rotation of the catheter body more than five full rotations.

In some variations, the rotation knob is configured to rotate the catheter body by a ratio of greater than one times the rotation of the rotation knob. The rotation knob may be configured to rotate the catheter body by a ratio of 1:n (knob rotation:catheter body rotation), where n is an arbitrary whole or fractional number. It is possible to construct the knob to enable reverse rotation of the catheter body with respect to the rotation knob (i.e., 1:−n). In practice, the rotation knob has been constructed at ratios of 1:3 and 1:4 with respect to the catheter body. For example, the rotation knob may be configured to rotate the catheter body by a ratio of between about 1.5 and about five times the rotation of the rotation knob; the rotation knob may be configured to rotate the catheter body by a ratio of about four times the rotation of the rotation knob.

In some variations, the device includes a side-facing port that is optically coupled to the distal end region of the optical fiber. The optical fiber may be fixedly attached to the distal end region of the catheter. The optical fiber may be only fixedly attached within the catheter body to the distal end region of the catheter, and is otherwise free to move longitudinally relative to the elongate length of the catheter body.

In some variations, the device further includes a rotational encoder configured to encode the rotational position of the catheter body. In some variations, the device may be used in collaboration with a position sensor subunit/system through which the catheter can be placed to encode the relative rotational and longitudinal position of the device. The position sensor can be of varied operating principles. For example, it may be optical or capacitive, or consisting of singular or plurality of sensing elements. More specifically, for example, the position sensor can be an optical mouse chip or a capacitive fingerprint sensor.

The fiber management pathway may include a helically-arranged channel having a plurality of turns. The helically-arranged channel may be configured as part of a spool. The spool may be positioned or held within the handle, and may rotate with the catheter body. In some variations, the fiber management pathway includes a helically-arranged channel having a plurality of turns, wherein the channel comprises walls having an upper radial height and a lower radial height. For example, the fiber management may be configured so that the fiber does not contact the upper radial height or the lower radial height of the helically arranged channel.

In some variations, the fiber management pathway is configured so that the fiber does not traverse a bend radius of less than the light leakage bend radius for the optical fiber. For example, the fiber management pathway may be configured so that the fiber does not traverse a bend radius of less than about a 5 mm bend radius.

Also described herein are Optical Coherence Tomography (OCT) catheter devices for visualizing a body lumen by rotation of the catheter and an off-axis optical fiber within the catheter that include: a catheter body having an elongate proximal to distal length; an optical fiber fixed to a distal end region of the catheter body and extending the length of the catheter body along a path that is off-axis of the elongate length of the catheter body; a proximal handle rotationally coupled to the catheter body; and a fiber management pathway comprising a helical channel within the handle that has a plurality of turns, an upper radial height and a lower radial height; and a limiter that restricts the number of catheter body revolutions, thereby preventing the optical fiber from exceeding the upper or lower radial heights of the helical channel as the catheter body is rotated relative to the handle.

Also described herein are methods of managing an optical fiber for off-axis rotation of an Optical Coherence Tomography (OCT) system, the method comprising the steps of: taking an OCT image using an optical fiber that is fixed to a distal end region of a catheter body and that extends along the length of the catheter body through an off-axis pathway within the catheter body and into a fiber management channel within a proximal handle to which the catheter body is rotationally fixed; and rotating the catheter body relative to the proximal handle so that the catheter body and optical fiber are simultaneously rotated.

The method may also include the step of limiting the rotation of the catheter body so that the optical fiber does not traverse a bend radius of less than the light leakage bend radius for the optical fiber. For example, the fiber management pathway may be configured so that the optical fiber does not traverse a bend radius of less than about a 5 mm bend radius.

The method may also include the step of encoding the rotation of the catheter relative to the handle.

In some variations, the method also includes the step of permitting the fiber to extend longitudinally within a channel extending off-axis along the length of the catheter.

The method may also include the step of limiting the rotation of the catheter body relative to the handle to a specific number of revolutions, for example, between about 2 and about 6 full rotations. In some variations, the method may limit the rotation of the catheter body relative to the handle to about five full rotations.

The step of rotating may comprise rotating a rotation knob that is coupled to the handle to rotate the catheter body relative to the handle. For example, the rotation knob may be configured to rotate the catheter body by a ratio of 1:n (knob rotation:catheter body rotation), for example, a ratio of greater than one times the rotation of the rotation knob. The rotation knob may be configured to rotate the catheter body by a ratio of 1:4, where about one full clockwise rotation of the knob results in about four full clockwise rotations of the catheter, or (in some variations) between about 1.5 and about five times the rotation of the rotation knob.

Also described herein are methods of managing an optical fiber that is positioned off-axis of a rotating Optical Coherence Tomography (OCT) system, the method comprising the steps of: taking an OCT image using an optical fiber that is fixed to a distal end region of a catheter body and that extends along the length of the catheter body through an off-axis pathway within the catheter body and into a fiber management channel within a proximal handle to which the catheter body is rotationally coupled, the channel having a plurality of helical turns and an upper radial height and a lower radial height; and rotating the catheter body relative to the proximal handle so that the optical fiber winds/unwinds and expands/contracts within helical turns of the fiber management channel between the upper radial height and the lower radial height as the catheter body is rotated in the clockwise and counterclockwise directions.

The method may also include the step of limiting the rotation of the catheter so that the optical fiber does expand/contract (e.g., coil) within the helical turns of the fiber management channel to a height that is greater than the upper radial height or less than the lower radial height.

Also described herein are methods of imaging a body lumen by Optical Coherence Tomography (OCT) using an elongate OCT catheter having an OCT sensor fixedly attached to a distal portion of the catheter. These methods may include the steps of: rotating the catheter from a proximal region of the catheter to rotate the OCT sensor at the distal portion while acquiring OCT images using the OCT sensor; and determining a rotational lag (θ) for the OCT sensor at the distal portion; and providing one or more OCT images corrected for the rotational lag.

In any of the methods described herein, the catheter may comprise an optical fiber extending off-axis along the length of the catheter.

The step of rotating the catheter from a proximal region of the catheter may comprises rotating the catheter at least 360 degrees in a first rotational direction. In some variations, the step of rotating the catheter from a proximal region of the catheter comprises acquiring a first image while rotating the catheter at least 360 degrees in a first rotational direction and acquiring a second image while rotating the catheter at least 360 degrees in a second rotational direction. Thus, the step of determining the rotational lag (θ) may comprise comparing an OCT image acquired while rotating in a first rotational direction to an OCT image acquired while rotating in a second rotational direction.

The method may also include storing the rotational lag (θ) determined for correction of additional OCT images.

The step of rotating the catheter from the proximal region of the catheter may comprise rotating the catheter from the proximal region until motion of the distal region is observed and recording the extent of rotation of the distal region of the catheter. In some variations, the step of rotating the catheter from the proximal region of the catheter comprises rotating the catheter in a first rotational direction and a second rotational direction from the proximal region until motion of the distal region is observed in the first direction and the second rotational direction and recording the extent of rotation of the distal region of the catheter in the first rotational direction and the second rotational directions. For example, the step of determining the rotational lag (θ) may comprise determining the difference of the extents of rotation of the distal regions of the catheter in the first rotational direction and the second rotational directions.

Also described herein are methods of imaging a body lumen by Optical Coherence Tomography (OCT) using an elongate OCT catheter having a central axis and an OCT sensor fixedly attached off-axis at a distal portion of the catheter, where the method includes the steps of: rotating the OCT sensor at the distal portion while acquiring OCT images using the OCT sensor; and displaying the OCT images as a toroidal mapping.

The step of displaying the OCT images may comprise determining the toroidal mapping based on the radial position of the OCT sensor relative to the catheter central axis of the catheter.

In some variations, the method further comprises correcting radial distortion in the image by scaling the OCT images. For example, the method may comprise correcting radial distortion in the image by multiplying the radial positions of the OCT images by a correction factor. In some variations, the method further comprises correcting radial distortion in the image by adding a correction offset to the radial positions of the OCT. In some variations, the method further comprises correcting radial distortion in the image by applying a mapping table of correction offsets to the radial positions of the OCT.

Also described herein are methods of imaging a body lumen by Optical Coherence Tomography (OCT) using an elongate OCT catheter having a central axis and an OCT sensor fixedly attached off-axis at a distal portion of the catheter, the method comprising: acquiring a first plurality of OCT scan lines using the OCT sensor; point-wise averaging of data in the first plurality of scan lines; transforming the averaged first plurality of scan lines by Inverse Fourier Transform; and displaying the OCT images as a toroidal mapping.

In some variations, the method of further comprises repeating the steps of acquiring, point-wise averaging and transforming for multiple pluralities of OCT scan lines, and in some variations, the multiple pluralities of OCT scan lines may be point-wise averaged to post-FFT average the OCT image.

BRIEF DESCRIPTION OF THE DRAWINGS

FIGS. 4A-4D show different views (cross-sectional, front, side perspective, and exploded views, respectively) of another variation of a handle including an optical fiber management mechanism.

DETAILED DESCRIPTION OF THE INVENTION

Described herein are OCT catheters and imaging systems using them, including methods for using them to image. In general, an OCT catheter as described herein is a flexible elongate catheter that includes an optical fiber for OCT imaging that extends the length of the catheter. The pathway taken by the optical fiber is displaced from the central longitudinal (proximal-distal) axis of the catheter, and thus may be referred to as off-axis. The catheter body is typically rotationally coupled to a handle portion so that the catheter body and the optical fiber rotate together relative to the handle.

OCT Catheters Having Off-Axis Optical Fibers

Figure 1:
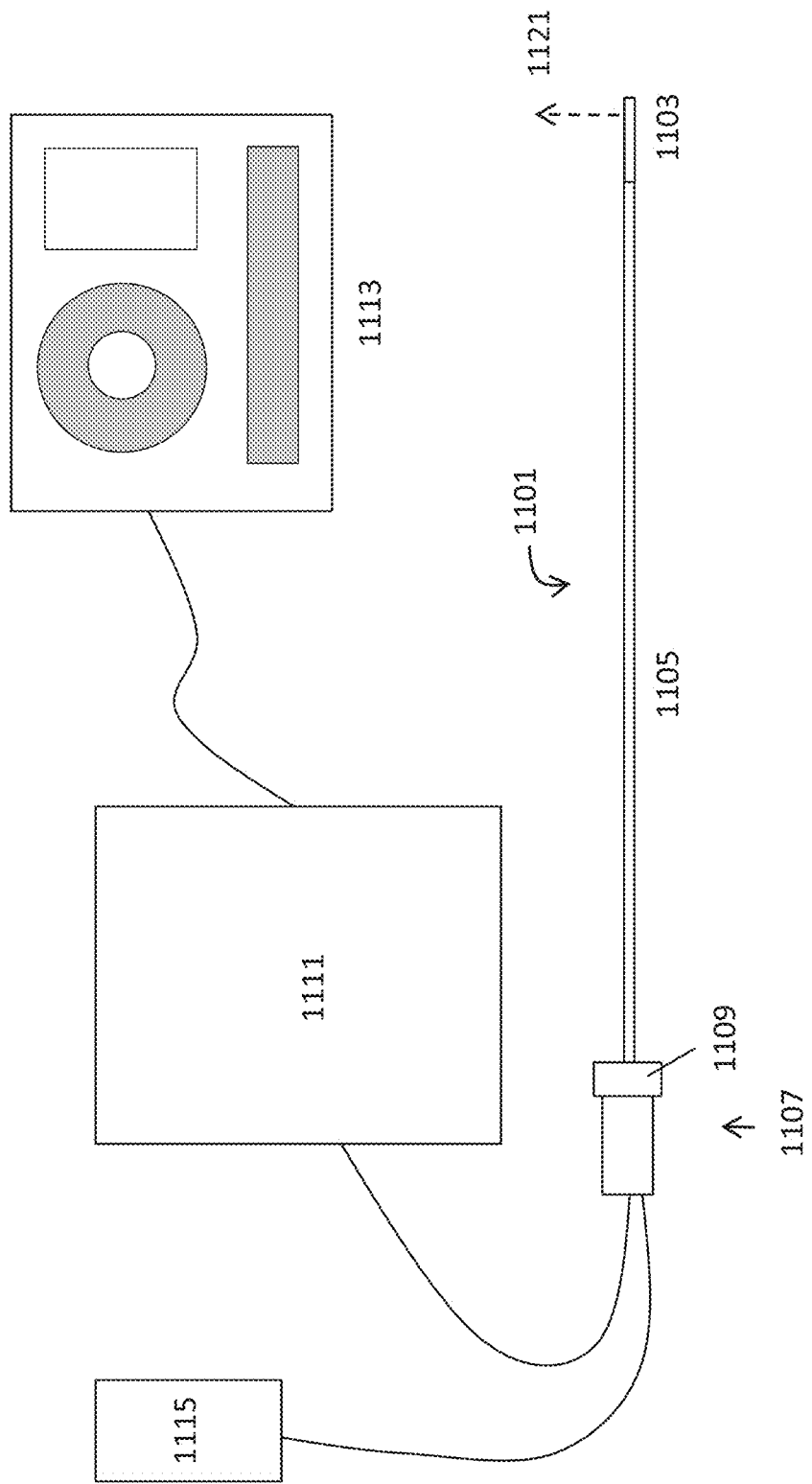
FIG. 1 is a schematic illustrating one variation of a system including an OCT catheter with an off-axis optical fiber.

FIG. 1 illustrates one variation of an OCT catheter having an off-axis optical fiber that may form part of an OCT imaging system configured as described herein. In this example, the device includes a catheter 1101 having a distal end 1103 that includes a one-dimensional OCT sensor (typically configured as a common-path interferometry device that does not require a separate reference arm). The sensor includes an optical fiber that extends through the length of the catheter and is (in this example) attached by an adhesive to the distal end region of the catheter. The "lens" of the OCT optical fiber is positioned facing outwards axially from a side of the distal end 1103 region. The hatched arrow 1121 indicates the imaging pathway (not to scale) from the sensor. The catheter 1101 may have an elongate and flexible catheter body 1105. The device may be configured so that the optical fiber imaging from the distal end is contained within the elongate body. The distal end of the optical fiber may be, as mentioned above, connected or fixed relative to a region (e.g., the distal end region) of the catheter, but may otherwise be unfixed in the body of the catheter. For example, the catheter may include an off-axis channel in which the optical fiber resides along the length of the catheter body. This channel may be lubricated to allow the fiber to slide axially (distal-proximal) as the catheter body bends or curves. In general, however, the optical fiber extends in a pathway that is radially displaced from the midline of the longitudinal axis (long axis) of the catheter. The pathway may be in a channel or lumen within the catheter body or it may be within an annular channel. In some variations, the optical fiber may extend in a straight path along the length of the catheter body, while in other variations, the optical fiber may extend in a helical or arbitrarily winding pathway, wrapping around the longitudinal axis of the catheter body.

The catheter is connected distally to a handle 1107 located at the proximal end of the device. A control 1109 on the handle 1107 may be used to rotate the catheter body, including the fiber optic that forms the one-dimensional scanner at the distal end. The control may be a rotational or rotary control, such as a wheel or knob. The control may be geared so that the rotation of the control 1109 has a mechanical advantage for rotating the catheter body. The system may be geared so that there is a 1:2, 1:3, 1:4, 1:5, 1:6, etc. mechanical/rotational advantage. For example, a 1:4 rotational advantage means that for every full rotation (e.g., 360°) of the control 1109 on the handle, the sensor passes through four full rotations (e.g., 1440°). Partial rotations of the control 1109 are multiplied for increased rotation at the distal end 1103 by the sensor. In practice, any ratio for the mechanical advantage between 1:1 and about 1:6 may be useful. For example a 1:1 ratio is as low one may desire for image quality reasons, and a ratio of 6:1 may be an upper limit to avoid loss of tactile feedback. For example when the catheter gets into a tight lesion, if there is too much mechanical advantage tearing may occur.

The distal end of the catheter may be configured as an atherectomy device and may include one or more tissue-removal elements and controls (not shown). For example, the device may include jaws, thermal/electrical/optical ablation devices, or the like, for removal of material from the vessel. The control for such elements may be positioned on the handle 1107. Rotation of the sensor may also rotate the tissue-removal elements.

The control 1109 controlling rotation of the one-dimensional sensor (rotational control) may be any appropriate control, including a dial, knob, button, etc. The handle may be configured to be hand held, although it may be configured to be operated by one- or two-hands. The handle may be configured to be held by a peripheral device. In some variations the control is configured to be operated by one or more fingers of the hand holding the handle. The handle may also include additional sensors, including an encoder for determining rotation or rotational position of the controller, as described in greater detail below.

The system may also include a connection to a controller 1111 for controlling the sensor, including applying power and receiving input from the sensor. The controller may be configured to perform the OCT image processing and to ultimately display one or more images representing the OCT images. The controller may also receive input from the encoder or other sensor on the handle. The OCT light source and any other OCT elements may also be included and/or connected to the controller 1111.

In some variations one or more additional input devices (not shown in FIG. 11) may also be used to communicate user commands/input to the controller 1111 and/or catheter 1101. An input device (or controller input device) may be a keyboard, keypad, joystick, mouse, etc. and may allow input of commands or selection of options to the system (or presented by the system) for controlling operation of the system. For example, the input device may allow the user to outline/markup regions of interest (e.g., using a mouse, pen, keyboard, etc.), or to toggle on/off recording/memory or determine parameters (including calibration parameters) of the system.

The system may also include one or more displays or monitors 1113 for displaying the imaging.

In some variations, the system may also include one or more fluid application and/or removal components. For example, the catheter 1101 may include one or more ports for connection to a fluid perfusion source 1115 (e.g., saline, etc.) during operation. Thus, fluid may be perfused from the proximal end of the device out of the distal end of the device (e.g., across the imaging sensor at the distal end). In some variations, the system may be adapted to remove cut material from the distal end of the device (e.g., either via suction, aspiration, or internal storage).

As mentioned above, an imaging system as described herein typically includes an optical fiber forming the OCT sensor element at the distal end of a catheter and a processor coupled to the catheter for processing imaging information received from the scanner and catheter. The catheter can be an atherectomy catheter with a cutting device. The processor or controller 1111 can include image processing software, hardware, firmware, or the like.

The OCT images collected may be displayed in any appropriate manner, including using two or more display modalities. For example, a one-dimensional OCT image may be displayed on a rotational axis by displaying as a toroid (e.g., two-dimensional 'doughnut' shape), as described in greater detail below. The one-dimensional OCT image data may also be displayed along a time axis as a waterfall-type display.

Displaying one-dimensional OCT imaging data as a two-dimensional azimuthal image (OCT data with respective rotational angles) can be produced by rotating the catheter and displaying the one-dimensional scans using angular information from the proximal end of the catheter. This rotational image is typically a toroid or doughnut-type display and may emphasize the relative rotational relationship between the different scans. As described in greater detail below, this display roughly approximates a cross-sectional view through the region (e.g., the lumen of a vessel) surrounding the catheter with the one-dimensional scanner. This image may not be scaled; furthermore the orientation of the image may not necessarily reflect absolute orientation in the patient. Instead, the orientation may be relative to the location of the scanning OCT imaging pathway.

Exemplary toroidal or azimuthal images are shown in FIGS. 15-20 and 22. The imaging space is the doughnut-shaped area between inner and outer circles. The inner circle may be thought of as the catheter with the outwardly directed one-dimensional scanner on the outer perimeter. A line (often shown as colored) extending axially outward from this inner circle represents the relative position of the one-dimensional scanner that is imaging outward into the surrounding region (e.g., the lumen of a blood vessel). If the catheter with the one-dimensional scanner (an OCT scanner) is held substantially axially fixed in the lumen of a vessel and rotated, the resulting 2D image may represent an OCT image of a cross-section through the surrounding vessel, including penetrating into the vessel walls. The catheter is typically manually rotatable back and forth axially around the vessel.

One of the challenges of manual rotation of these catheters is that there may be a substantial lag between the rotation applied (e.g., at the proximal end by the user) and the actual rotation of the distal end of the catheter where the one-dimensional imaging system (optical fiber) imaging pathway extends from the catheter. This problem is addressed in greater detail below.

As mentioned briefly above, images from the catheter may also be displayed on a time axis, separately from the angular rotation axis given by the toroidal, azimuthal images just described. Thus, images relating to time and tissue depth can be produced without the angular information; these images may be referred to herein as "waterfall" images. These may also be referred to (per ultrasound nomenclature) as M-mode images (e.g., depth vs. time). Both azimuthal and waterfall images can be displayed simultaneously on a visual display or displays, providing users with information about both the relative position and relative depth of structures related to the one-dimensional scanner. Thus, a display may include both azimuthal and waterfall images of the one-dimensional scanner. The relative importance of the two modes of display can be changed in real time to reflect the nature of the surgical procedure. For example the waterfall or M-mode display is more valuable during a cutting (atherectomy) operation, whereas the radial display is more useful for pre-treatment survey and planning, and post-treatment outcome assessment. The switch may be made automatically with a control on the device handle, or for example by sensing the actuation of the atherectomy cutter. In some variations the system may therefore provide a processor for processing and presenting the information from the scanner, memory for storing information from the scanner and/or user, one or more computer monitors or television screens for displaying the images, a graphical user interface (GUI) allowing interaction with the images, and a control or controller for operating the imaging system. Additional elements (some of which are describe below) may also be included.

Figure 2A:
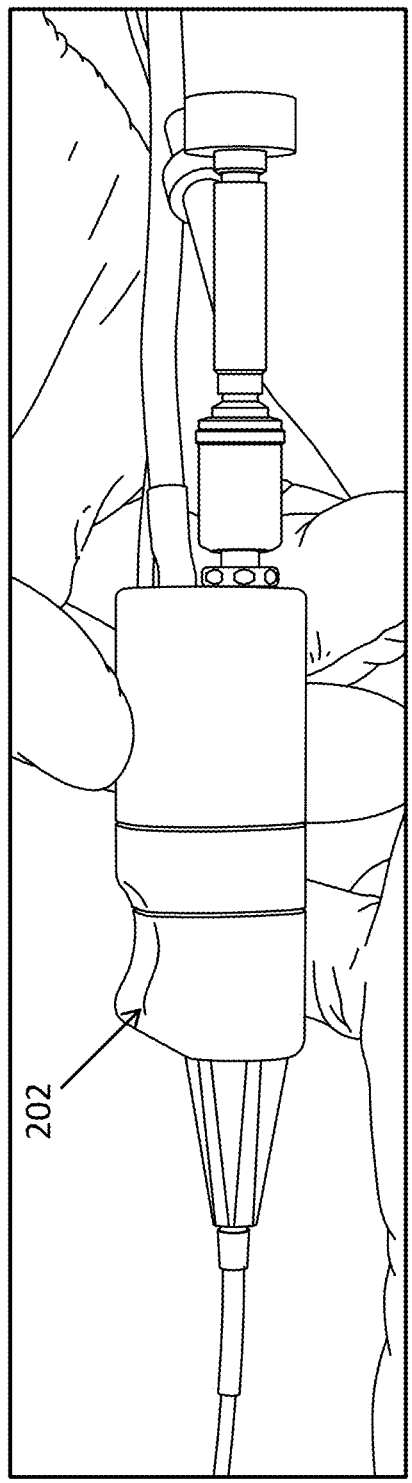
FIGS. 2A and 2B show variations of a handle for an OCT catheter including a fiber management pathway allowing rotation of the catheter and optical fiber relative to the catheter handle body.
Figure 2B:
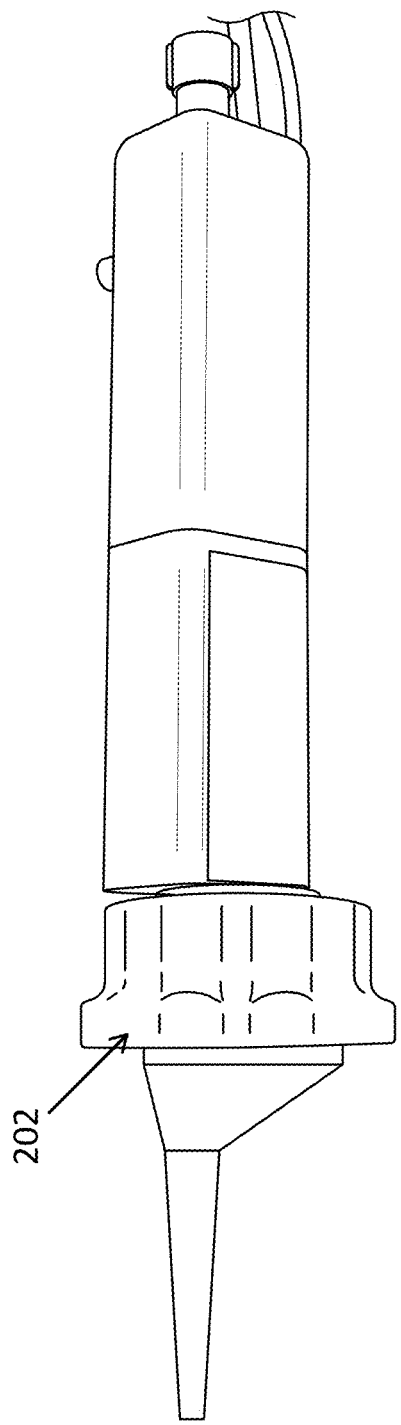

For example, a catheter for imaging as described herein can include a hand piece near the proximal end and a controller configured as a thumb/finger wheel on the hand piece for controlling rotation of the catheter during imaging. FIGS. 2A and 2B show variations of handles or hand pieces. Rotation of the finger wheel 202 in the counter-clockwise direction causes the catheter body (and therefore the OCT imaging element secured at the distal end region of the catheter) to rotate in the counter-clockwise direction, and rotation of the finger wheel 202 in the clockwise direction causes the scanner on the distal end of the catheter to rotate in the clockwise direction. The finger wheel can also be configured to produce opposite rotation of the catheter body (i.e., clockwise finger wheel rotation producing counter clockwise catheter body rotation). As discussed briefly above, the finger wheel 202 can be configured to rotate the catheter at various gearing ratios, such as ½× (½:1), 2× (1:2), 3× (1:3), 4× (1:4), etc. For example, when the finger wheel is implemented with a 4× gear ratio, a 90 degree rotation of the finger wheel translates to a 360 degree rotation of the distal (imaging) end of the catheter.

Figure 3A:
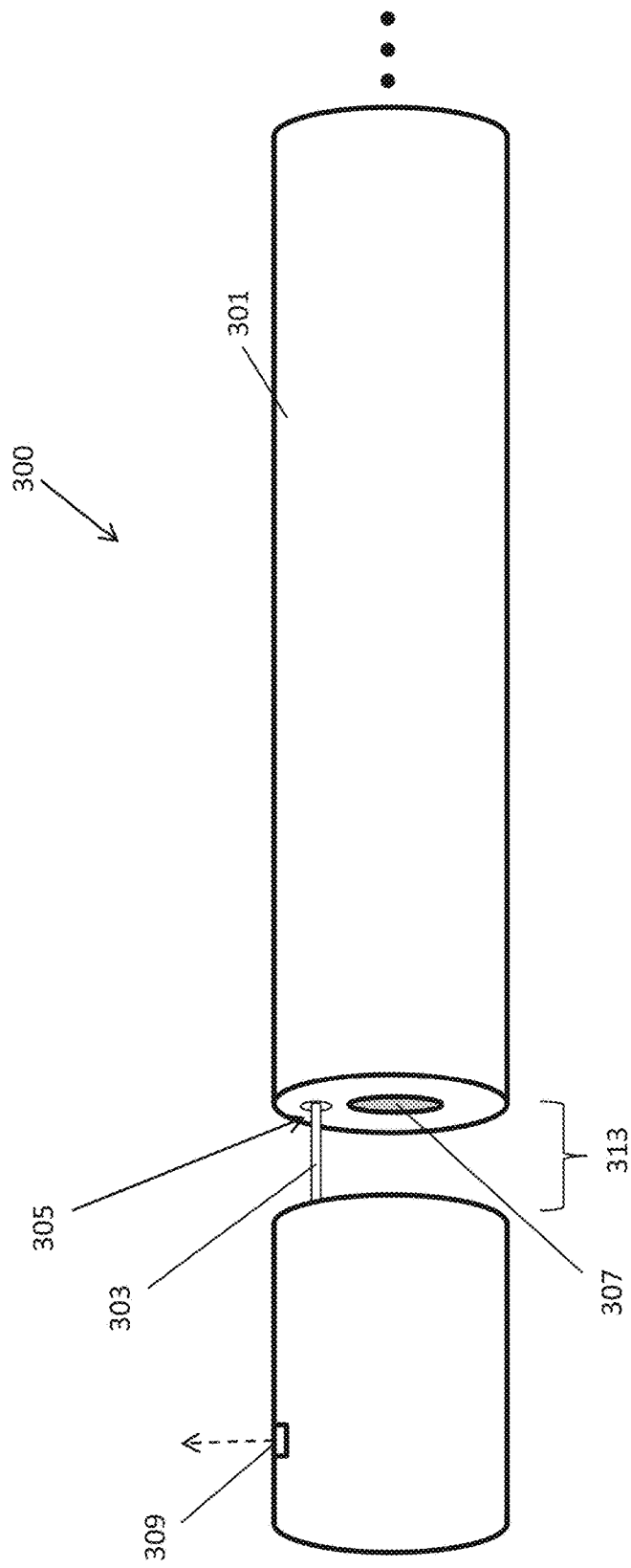
FIGS. 3A and 3B show one variation of a catheter body including an off-axis fiber optic.
Figure 3B:
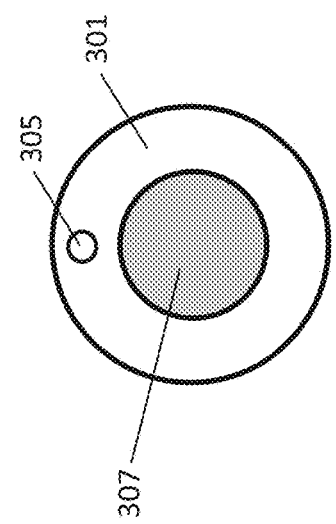

The catheter body region of the OCT catheter generally is an elongate, flexible and thin body region extending distally from the handle. The catheter body is rotationally coupled to the handle. FIGS. 3A and 3B illustrate one variation of a catheter body, showing a cross-section through the catheter body to indicate the off-axis pathway taken by the optical fiber forming the OCT image. For example, in FIG. 3A, the catheter body 301 is an elongate, flexible tube having a central hollow lumen 307 and an off-axis central passage 305 through which an optical fiber 303 may pass. The optical fiber 303 may terminate distally at a window (e.g., a side-facing window) 309, from which the optical pathway forming the OCT image may extend (dashed line). The cut-away region 313 of the catheter body in FIG. 3A shows the internal arrangement of the off-axis pathway 305 for the optical fiber 303, and the center lumen 307.

FIG. 3B shows a cross-section through the catheter, also indicating the arrangement of the off-axis pathway 305 for the optical fiber 303, and the center lumen 307. The catheter body may also include additional internal lumens (not shown).

Any appropriate optical fiber (e.g., fiber optic) may be used, including bend-tolerant fibers (e.g., "bendable" or "bend-loss resistant" fibers). For example, in one variation, the optical fiber has a fiber cut-off of less than 1240 nm and single mode performance between 1270 and 1380 nm (and be manufactured compatible with SMF-28 standards). The outer jacket of the fiber optic cable may be 2 or 3 mm (OD) polyurethane, for example. The optical fiber connectors may be Diamond E2108.6 connectors with a 0.25 dB maximum insertion loss and a −65 dB maximum return loss. Typically, optical fibers have a defined minimum bend radius corresponding to the radius below which the signal loss through the wall of the fiber from the fiber core occurs. For example, a highly bend-loss resistant fiber will have a minimum bend radius threshold of approximately 5 mm. When the fiber is bent to a curve with a radius less than this minimum bend radius, the signal (light) within the fiber will decrease beyond acceptable levels as light is lost through of the wall of the fiber.

As mentioned, by resisting one end of the optical fiber to the rotatable catheter body, the optical fiber will rotate with the catheter body relative to the handle. This off-axis rotation of the optical fiber with the catheter may result in pulling and bending of the optical fiber. As mentioned above, the signal on the fiber may degrade as the fiber is bent, even in the most bend-tolerant (bend-loss resistant) optical fibers. Further, the fiber optic may potentially tangle, making the catheter difficult to use, and may ultimately break if too much mechanical force is applied.

Thus, the catheter handles described herein may be adapted for handling the off-axis rotation and bending of the optical fiber in the catheter. For example, any of the handles described herein may include an optical fiber management pathway through which the optical fiber extends from the rotating catheter body. The optical fiber management pathway may be configured so that the fiber does not bend beyond the minimum bend radius of the optical fiber (which may range between 5 mm and 25 mm). For example, the overall fiber management pathway within the handle may traverse bend radii greater than about 5 mm, greater than about 7.5 mm, greater than 10 mm, etc.

Within the handle, the optical fiber management pathway may include a defined pathway around a spool or drum. For example, the pathway may be configured in a helical geometry. Non-helical pathways are also possible, and may be used. The spool may include a helical channel that curves around an approximately cylindrical body. The channel may have defining elements (e.g., walls, separated ribs, fins, etc.) extending from a top (e.g., upper radius) to a bottom (e.g., lower radius). An optical fiber may pass along this channel in a defined pathway and wind around the spool; within the channel, the turns or windings of the fiber do not overlap or interact with each other, but are kept separate by the defining elements of the channel (e.g., walls). As the optical fiber is rotated off-axis, the windings of the fiber may expand or constrict within the helical channel (simultaneously unwinding and winding, respectively). The stiffness of the optical fiber will allow the tension on the fiber to approximately uniformly expand and unwind within the helical turns around the spool. This is described below, for example in FIG. 5. The dimensions of the channels of the fiber management system, including the size of the spool and the heights of channel walls, for example, as set by the upper and lower radius, may be calculated to allow a predetermined number of rotations of the catheter (and thus the off-axis optical fiber).

Figure 4D:
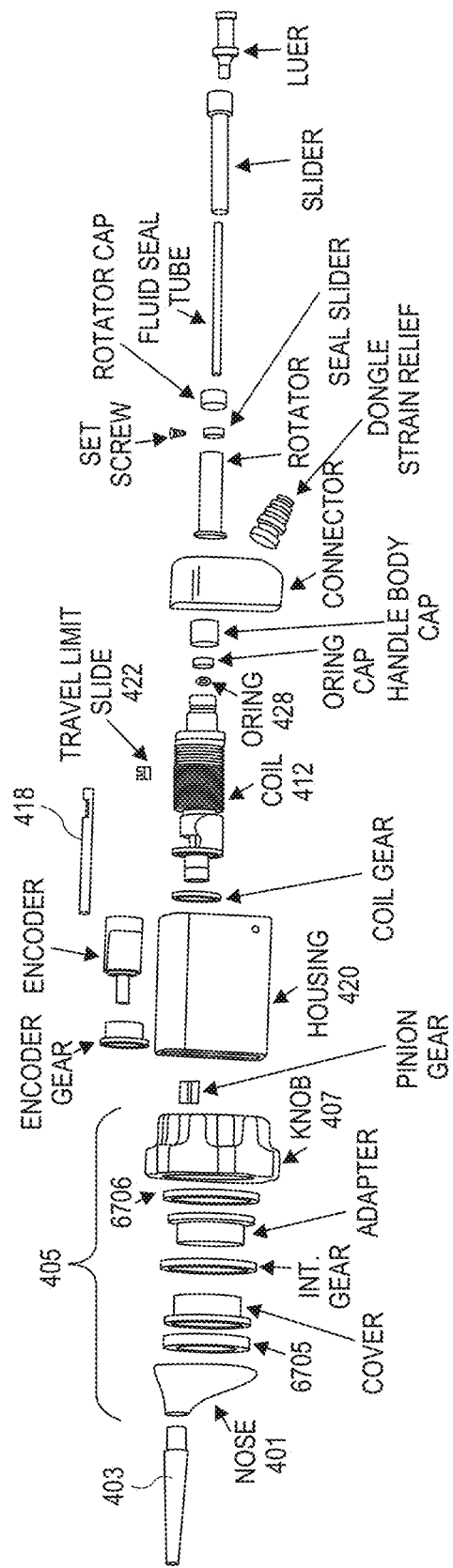

FIGS. 4A-4D illustrate one variation of a handle including a fiber management pathway having a spool. FIG. 4A shows a longitudinal cross-section through a handle, and an exploded view of the handle, showing the component parts of this example, is illustrated in FIG. 4D. FIGS. 4B and 4C show front and side perspective views, respectively. The catheter body (including the optical fiber therein) extends from the distal end of the handle. In FIGS. 4A-4D, the catheter body is not shown, for simplicity. In this example, a nose region may surround the catheter body, which may rotate therein. The nose may include a support extension 403 that may also provide strain relief as the catheter body attaches to the handle. Proximal to the nose, a rotator assembly 405 may include a control such as a knob (e.g., finger knob 407) that may be rotated to rotate the catheter body. The rotator assembly may including one or more rotation transmission elements, including gears or belts for example for multiplying the rotation of the rotator knob (e.g., 407) by a multiplying factor (typically greater than 1×, e.g., 1.5×, 2×, 3×, 4×, 5×) when rotating the catheter body. The catheter body may be fixed or secured to a hypotube liner that connects to the catheter body, and provides an exit (e.g., window) from which the optical fiber may exit the catheter body and enter the fiber management spool 412. After exiting the fiber spool (e.g., the long helically-wound channel of the spool), the fiber may be secured (anchored, fixed, or pinned) to a location next to or proximal to the spool (e.g., within the handle or outside of the handle). For example, the fiber may attach to a connector for connection to the downstream OCT system (light source, processor, etc.). In some variations, the fiber spool rotates with the catheter body and may be affixed to a rigid length of hypodermic needle tubing ("hypotube").

FIGS. 4A and 4D illustrate additional elements that may be included, such as a handle housing (which may include an external grip region) 420, a travel or rotation limiter 422, and seals or o-rings 428. The rotation limiter may prevent overturning or rotation of the catheter body beyond the capacity of the fiber management pathway, i.e., to prevent the fiber from being stressed or placed under tension by over-rotation. In some variations, the rotation limiter may be considered part of the fiber management pathway, and may limit the rotation of the catheter body to a pre-determined number of rotations (complete rotations clockwise or counterclockwise). For example, the pre-determined number of rotations may be between 2 and 10 (e.g., about or less than: 10, 9, 8, 7, 6, 5, 4, 3, etc. including partial rotations of these such as half, quarter, tenth, etc. rotations). For example, the handle (e.g., the fiber management and/or rotational control) may be configured with a limiter that limits the number of full rotations of the catheter body through about 5 complete rotations (1800 degrees of rotation).

In the variation of the handle shown in FIGS. 4A-4D, the catheter may be an atherectomy catheter or a guidewire-placement catheter that includes a distal end region that is manipulated to cut or move as the device is advanced or withdrawn. The catheter body (and particularly the distal end region) may also be steerable. Thus, in FIGS. 4A-4D, the distal end may be manipulated by one or more control elements for steering and/or actuating. The handle may also include one or more ports for the application or withdrawal of materials through the catheter (including perfusion fluid, etc). Exemplary elements are labeled (e.g., slider, rotator, fluid seal tube, luer, etc.) in FIG. 4D.

As described in greater detail below, an encoder 425 may also be included to encode the rotational position of the catheter body and/or the optical window or scanning window near the distal end region of the catheter body, from which the OCT images are recreated. Any appropriate encoder may be used.

The length of the handle may be varied, as may the width or girth of the handle. In general, the handle is configured so that it may be easily manipulated by a single hand, including rotation of the finger knob or wheel. In some variations, the handle may be configured for two hands or be held by a peripheral device. The variations of the handles shown in FIGS. 2A, 2B and 4A-4D are manual handles, in which the catheter body is rotated manually. In some variations, the catheter body is rotated automatically. For example, the catheter body maybe rotated or manipulated electrically. Thus, the handle may also include a motor or driver for rotating the handle, and the handle may include controls (e.g., buttons, sliders, etc.) for controlling the rotation.

Figure 5:
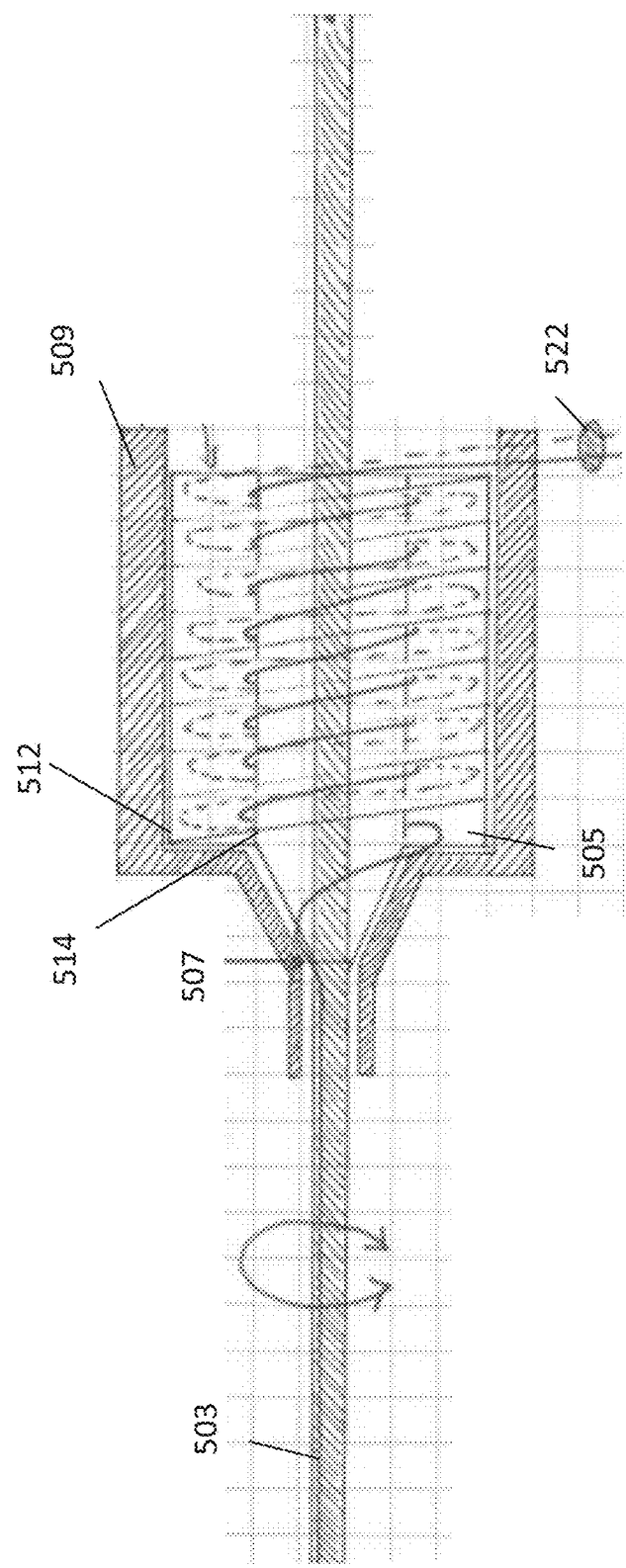
FIG. 5 illustrates one variation of an optical fiber management region within a handle.

FIG. 5 shows a schematic of one variation of a fiber management pathway, including a spool 505. In this example, a catheter body 501 includes an off-axis optical fiber 503. The catheter body is coupled to the spool 505, so that the two rotate together, relative to the outer body of the handle 509. The catheter may include a torque shaft, central lumen, or the like, as mentioned above. The fiber "take off" from the catheter body is controlled to ensure that there are no optical losses, and to prevent stress on the fiber that may lead to breakage. For example, the take off region may be protected by a hypotube liner, as mentioned above. The catheter body may then be skived at a predetermined window location so that the fiber can exit the catheter and enter the spool of the fiber management pathway. The take off region may be configured so that there are no sharp turns (e.g., all bend radii are greater than the threshold bend loss radius of the fiber) , while allowing the fiber to coil around the semi-enclosed windings of the spool. In FIG. 5, the spool is shown schematically and forms a helically wound channel with walls having an upper radius 512 and a lower radius 514. The fiber may coil around the spool within the channel. As the catheter body and off-axis optical fiber are rotated relative to the handle, the optical fiber coiled within the spool may expand (shown as dotted lines) and contract (shown as solid lines) with clockwise and counterclockwise rotation of the catheter body. A region of the optical fiber proximal to the spool may be constrained 522 either loosely or tightly so that it may not move laterally (relative to the handle), while still allowing the fiber to wind/unwind and expand/contract within the fiber management spool. Thus, the optical fiber may extend or retract longitudinally as the catheter body is bent, stretched and/or rotated, by expanding or contracting the coils of optical fiber within the spool.

Figure 8A:
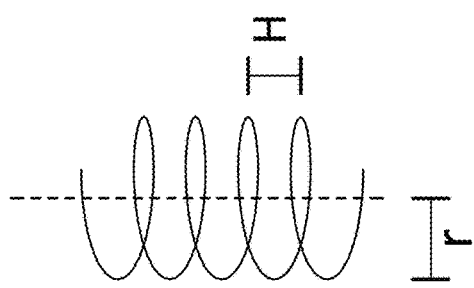
FIGS. 8A-11 illustrate one method of determining the dimensions of the spool of the fiber management pathway.
Figure 8B:
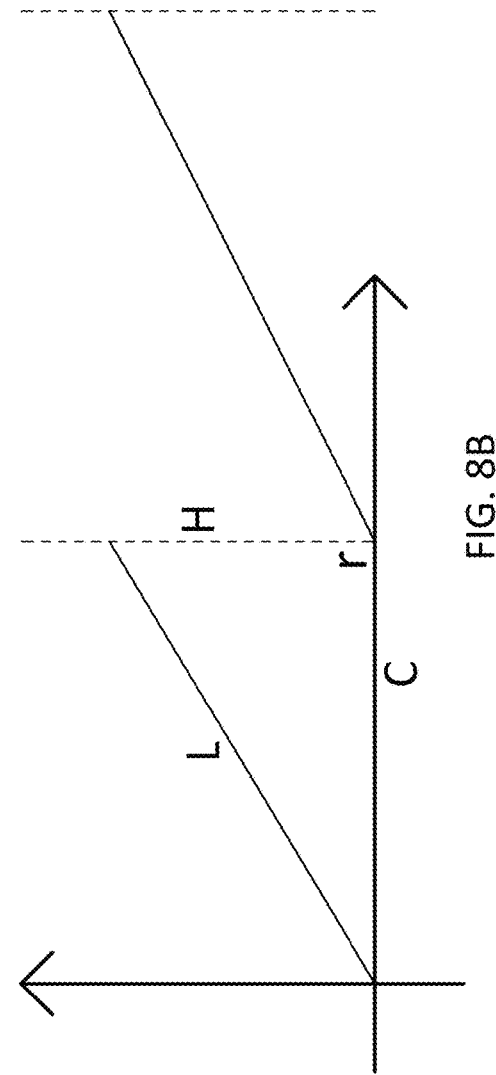

The spool of the fiber management pathway may be configured to allow a pre-determined number of rotations of the catheter body, and may take into account the dimensions of the handle, including the handle length and width. FIGS. 8A-11 describe one method of determining the dimensions of the spool of the fiber management pathway. FIG. 8A illustrates an exemplary helical coil. For any given helical coil, there may be N revolutions, the height of each revolution may be H, the distance from the helix to the center axis may be r (and the circumference, C, is thus $2\pi r$), and the length in one revolution is L, so that N*L is the total length of the helix. An "unrolled" helix may be represented as shown in FIG. 8B, showing that the unrolled helix becomes a repeating line on a plane, which is the hypotenuse of a right triangle having a base length, C, equal to the circumference of the coil ($2\pi r$) and a height of one revolution of the helix. From this relationship, the total length of the helix (N*L) can be expressed as: $L^2 = C^2 + H^2$. Therefore N*L is:

$$NL = N\sqrt{C^2 + H^2}$$

Figure 9:
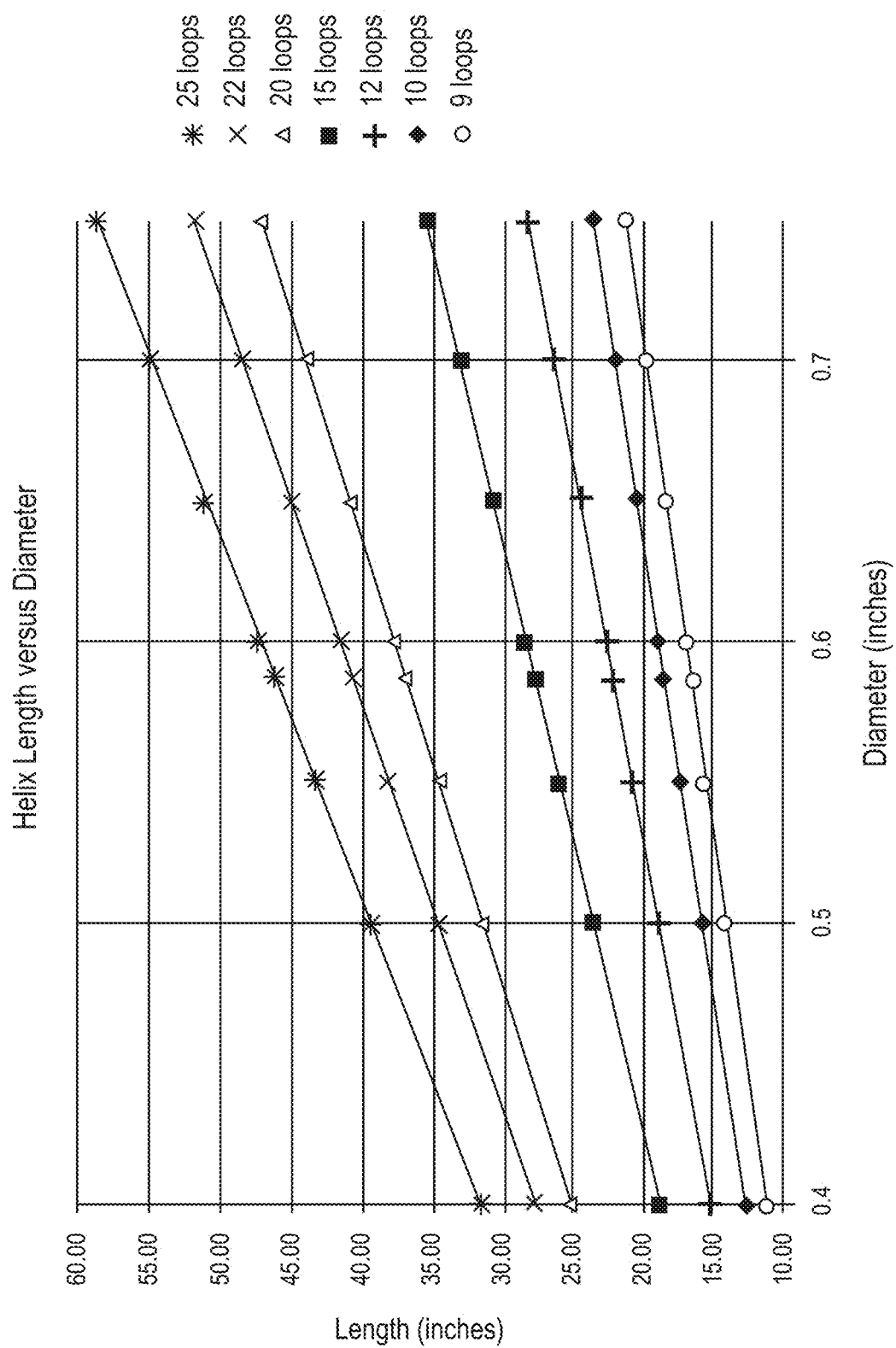
Figure 10:
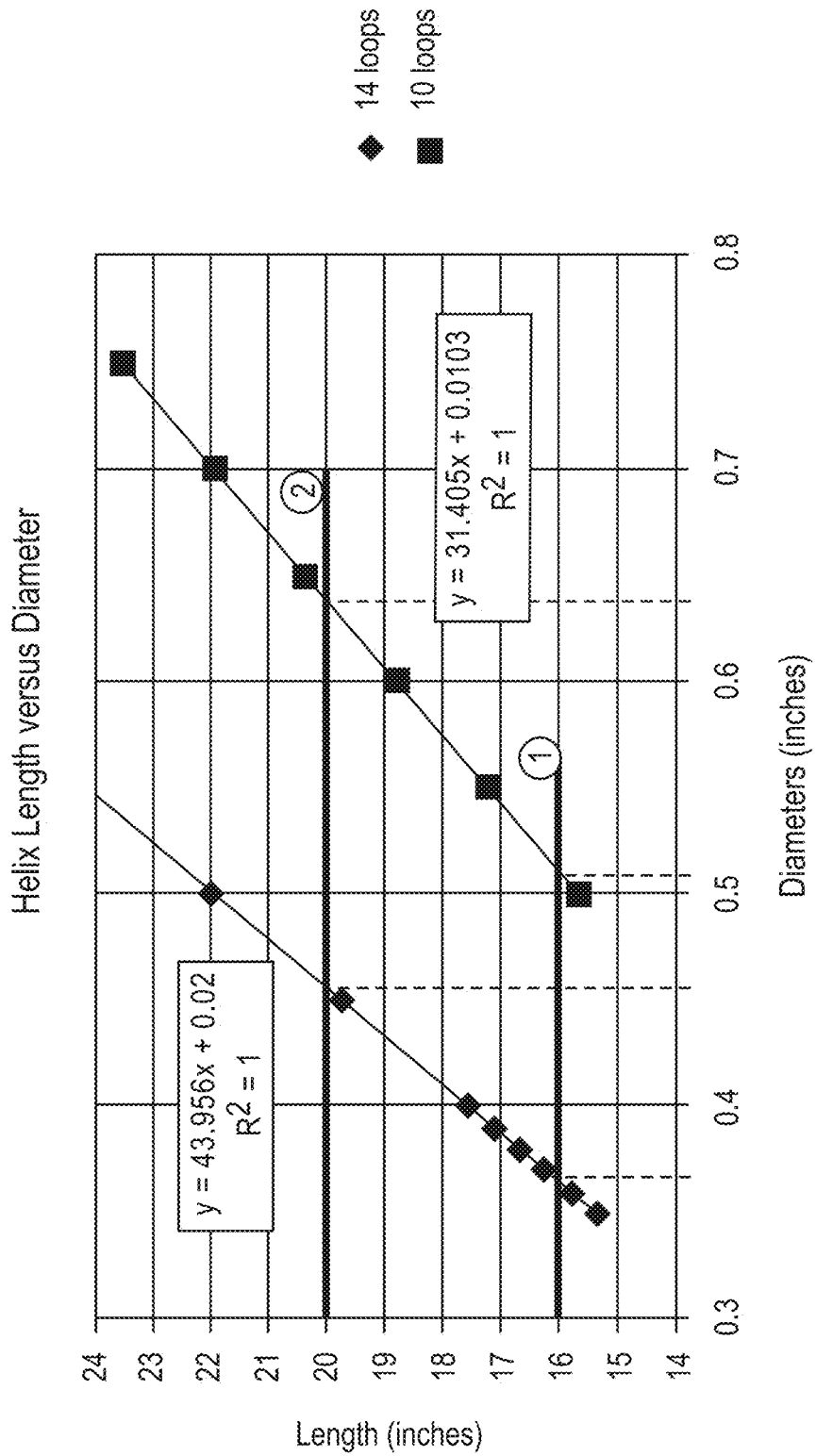

Application of this relationship to various N and C may be expressed and graphed as length versus diameter for different numbers of loops, as shown in FIG. 9. By selecting a desired range of rotations (e.g., between 4 and 5 full rotations), we may use this relationship to determine the internal and external radii of the helical channels of the spool. For example, in FIG. 10, for four rotations (e.g., 10 to 14 coils of fiber on the spool), possible dimensions of the spool channel walls may be determined by extrapolating values (e.g., drawing straight lines) at different values for the fixed length of the optical fiber located on the spool, as shown. Extrapolating from line 1 at N=10, the diameter may be approximately 0.51", and at N=14, the diameter may be 0.37" for the same length of optical fiber. This will therefore suggest a spool with an inner diameter (ID) of less than 0.37" and an outer diameter (OD) of greater than 0.51". Similarly at line 2, a spool with ID<0.46" and an OD>0.63" are suggested.

Figure 11:
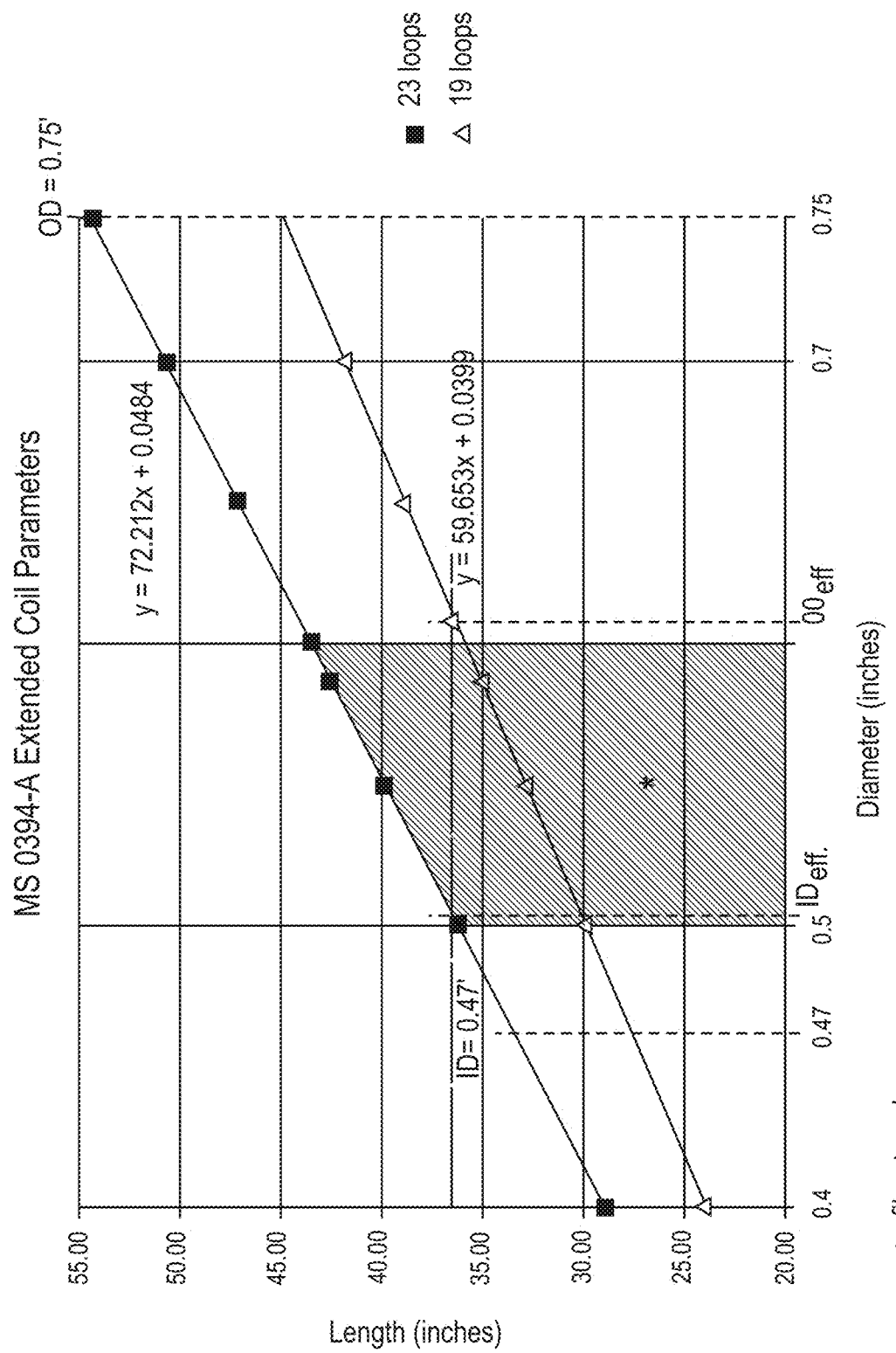

In practice, some slack must be added back to the spool after a fiber is pulled tight at the higher $N_x$ to be used (where N is the number of windings that the optical fiber takes on the spool, x is the target number of catheter body rotations, and $N_x = N+x$). FIG. 11 illustrates an example where four rotations are targeted, so the maximum N ($N_x$) is 23 and the minimum N is 19. The calculated NL curves versus diameter for this scenario are shown in FIG. 11. Applying the analysis above, the suggested OD is 0.75" and the suggested ID is 0.47" for the fiber management spool. However, in this example it is desirable to add some optical fiber "slack" back onto the coil, in addition to the necessary NL. For example, approximately 2.75" of slack may be added to the spool after the fiber is pulled tight at 23 coils. This yields an NL of 36.47" (NL at 0.47" is 33.99, plus 2.75"). The dimensions for 23 and 19 coils with a total optical fiber length of 36.74 are therefore an OD(effective) of 0.615" and an ID(effective) of 0.508". These effective diameters for the optical fiber within the helical channel would therefore allow the optical fiber to expand and contract during rotation through four turns without hitting either the outer diameter of the channel or the inner diameter of the spool.

Figure 6B:
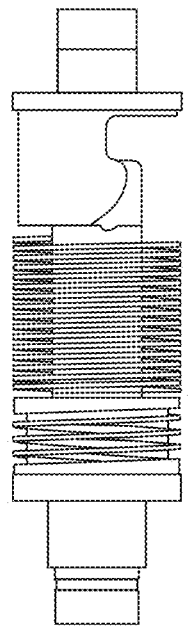
FIGS. 6A-6D show side perspective, side, front, and cross-sectional views, respectively of one variation of an optical fiber management spool that may be used as part of an optical fiber management mechanism.
Figure 6D:
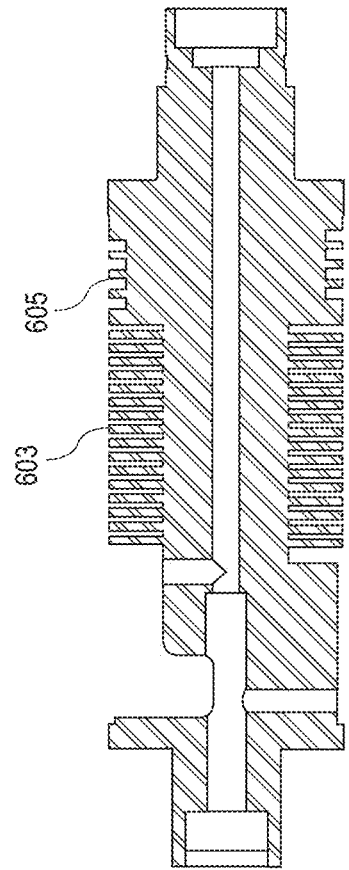
Figure 6A:
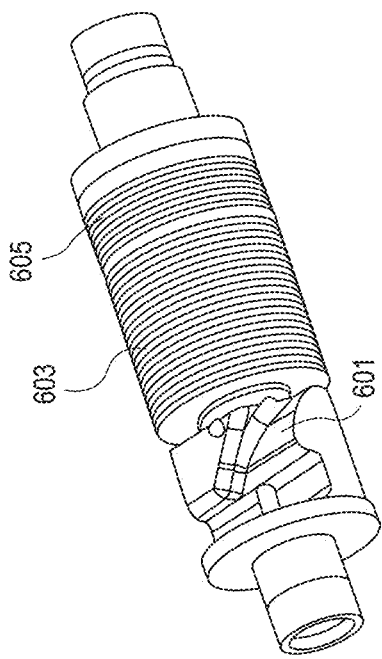
Figure 6C:
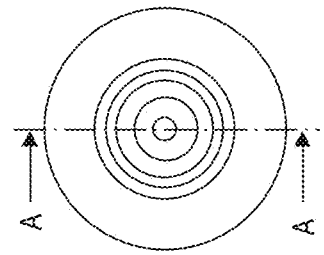
Figure 7B:
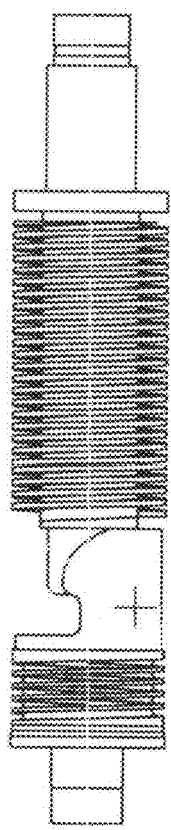
FIGS. 7A-7D show side perspective, side, front, and cross-sectional views, respectively of another variation of an optical fiber management spool that may be used as part of an optical fiber management mechanism.
Figure 7D:
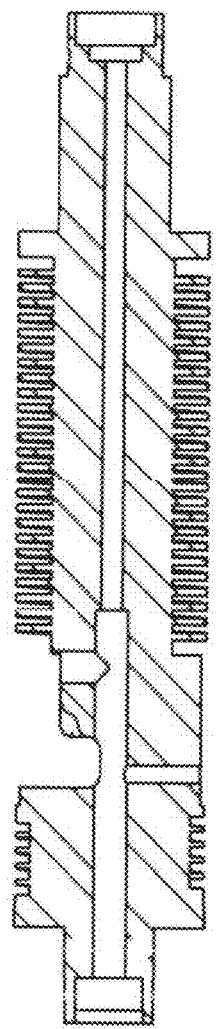
Figure 7A:
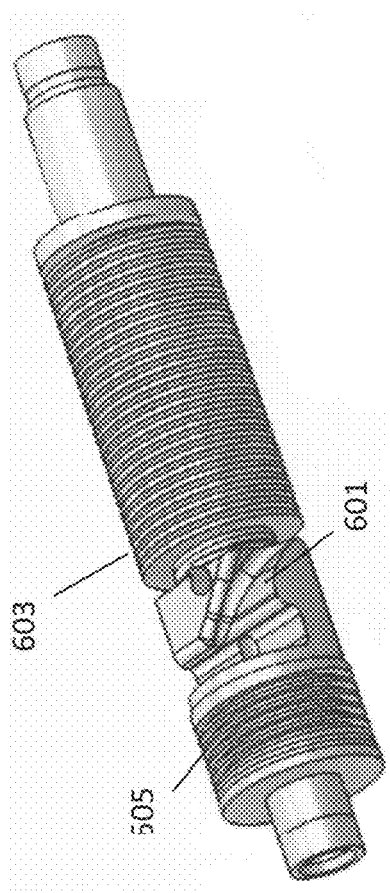
Figure 7C:
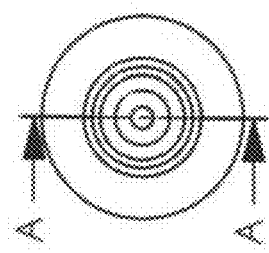

Returning now to FIGS. 6A-7D, two variations of the fiber management pathway that may be positioned within the handle are shown. In FIGS. 6A-6D, the spool is shown including the fiber take off region where the fiber exits the catheter (e.g., a fiber lumen off-axis within the catheter) and wraps around the spool's helical channel. The central region of the spool is left hollow, and may be placed in communication with a central passageway of the catheter (and may hold a torque shaft, passageway, etc.). FIG. 6A shows a perspective view of the spool, including a distal region 601 where the fiber exits the catheter body and enters the spool channel, and a middle region 603 comprising the spool channel into which the optical fiber is wound. The channel is a helical winding around the spool, as described above. A proximal region 605 includes a rotation limiter region. A pin or other limiter portion may mate with limiter grooves on the spool, as illustrated in FIG. 6D.

FIGS. 7A-7D shows another variation of a spool having an extended coil design that may further reduce light loss by avoiding tight radius bending while providing sufficient knob rotations. For example, compared to FIGS. 6A-6D, the embodiment shown in FIGS. 7A-7D includes 24 (vs. 15) fiber coils, and has a larger minimum diameter (0.476" vs. 0.400") and an increased fiber trench width (0.030" vs. 0.020"), while the OD remains the same (0.750"±0.001"). The increased number of fiber coils may increase the available amount of slack, enabling one more knob rotation (5 vs.

4), and an increased minimum diameter may keep the optical fiber from being bent too tightly and reduce the amount of light lost when the fiber is in the tightly wound position. Finally the increased fiber trench width may make the spool easier to manufacture, and may also allow help prevent binding as the fiber expands and contracts within the semi-enclosed channel of the spool. The channel is referred to as semi-enclosed, because the upper surface may be open, though in some variations it may be closed (e.g., within a tube or sleeve). In FIGS. 7A-7D, the rotation stop region 703 has also been shifted to the distal end of the spool.

As mentioned above, the handle may also include an encoder to encode rotational information about the catheter body and/or the image-forming window out of the catheter body. An encoder may provide this rotational position information to a processor (including the OCT image processor) for display or calculation of the image based on rotational position. Because a lag may be present between rotation of the distal and proximal ends of the device when rotating from the proximal end of the catheter body, the processor may include logic (including hardware, firmware and/or software) to correct for the lag. FIGS. 12A-12E illustrate different variations of encoders that may be used.

Figure 12A:
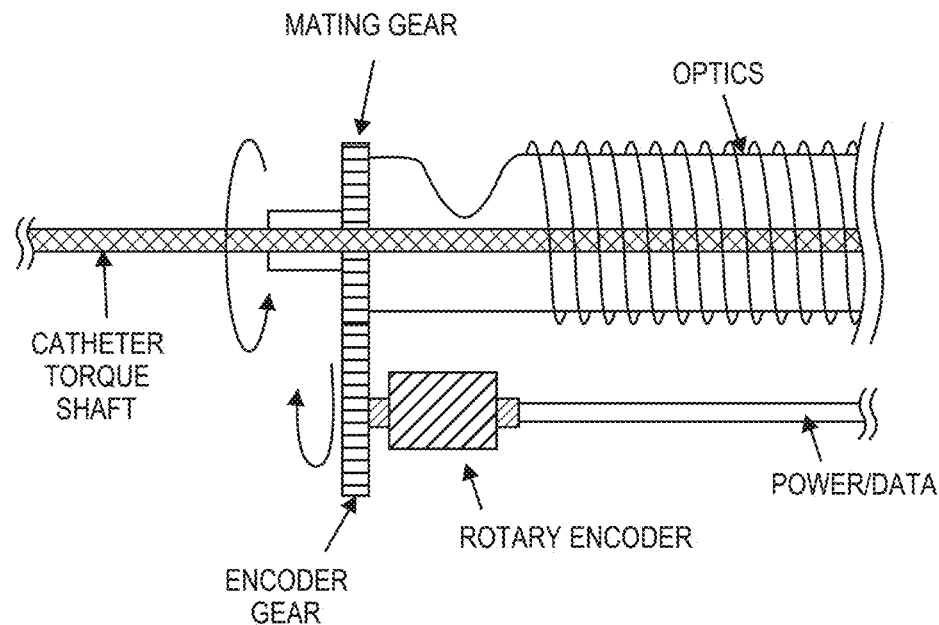
FIGS. 12A-12E illustrate various encoders that may be used with any of the catheters and systems described herein.

In FIG. 12A, a Hall-effect sensor may be used to detect catheter rotation in the device handle. The rotation can be on- or off-axis. In this variation, an encoder gear mates with a gear that is rotated with the catheter body (in this example, the spool, which is connected to the catheter body, is rotated). A rotary encoder provides output information indicating the rotary position of the catheter body.

Figure 12B:
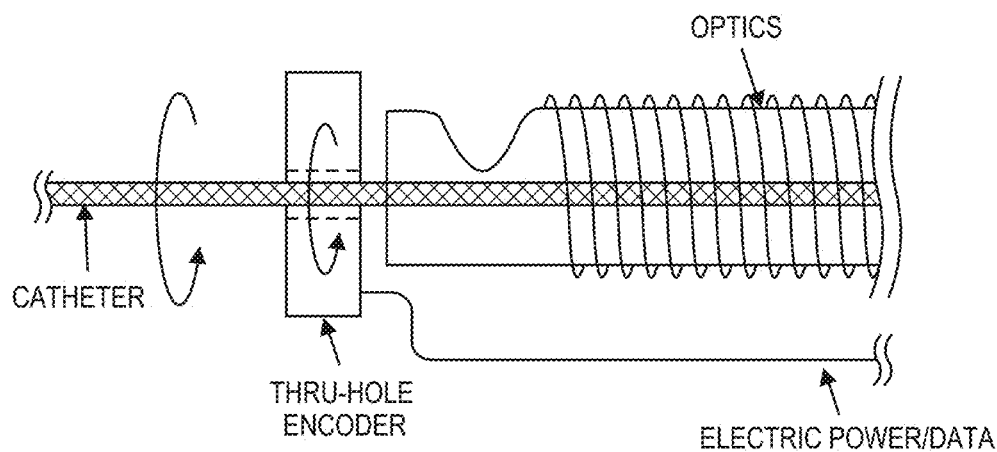
Figure 12C:
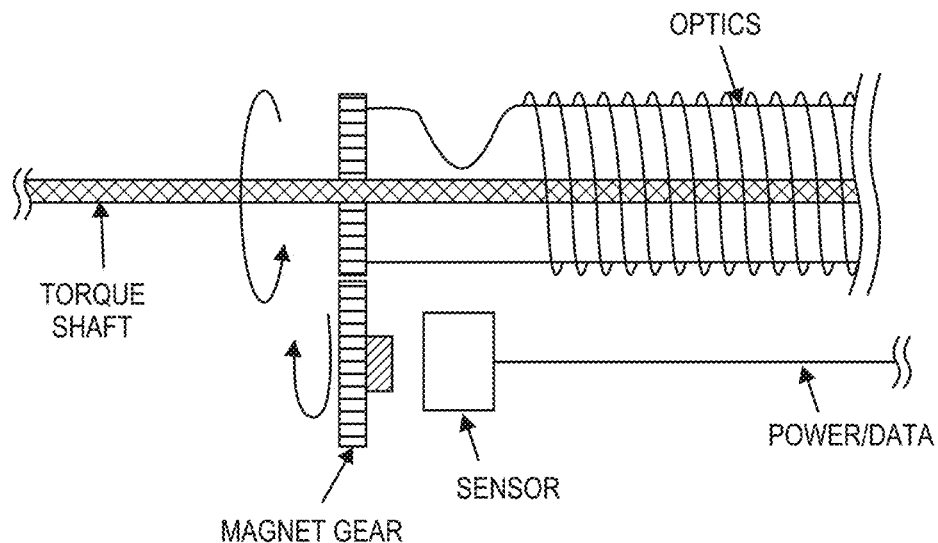
Figure 12D:
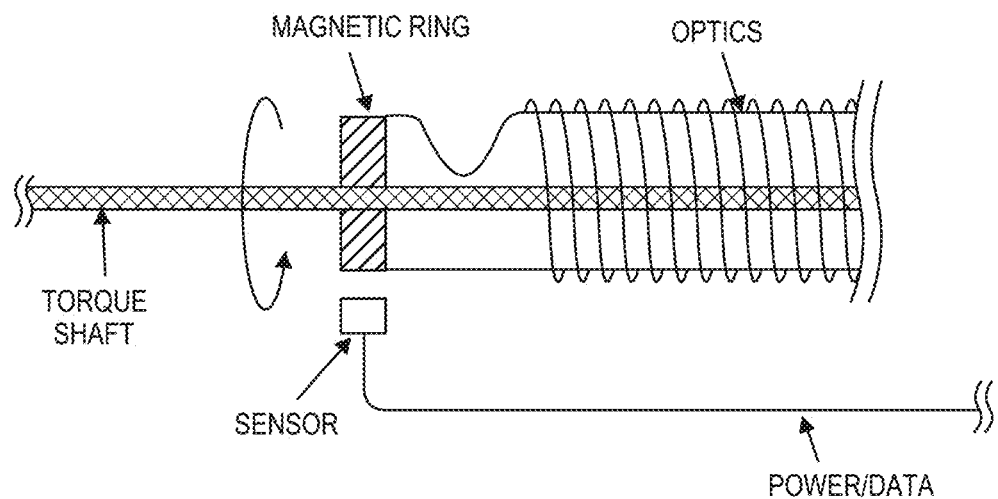
Figure 12E:
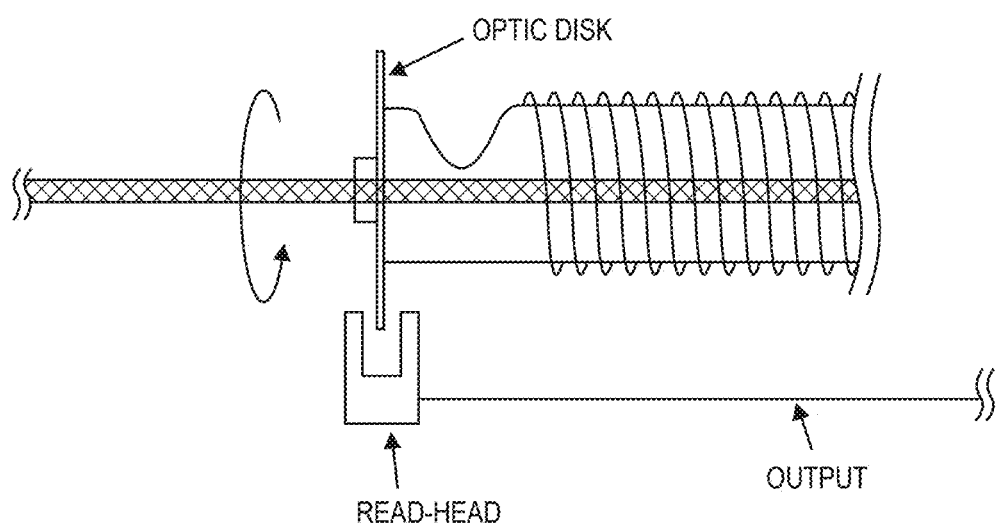

FIG. 12B illustrates a schematic of a variation having an on-axis through-hole encoder. In this example, the rotation of the catheter body results in direct rotation of the encoder. FIG. 12C illustrates one example of a non-contact encoder, in which an air gap exists between the encoder sensor and a magnet coupled to the rotary gear that rotates as the catheter body rotates. The sensor may therefore detect rotation. Similarly, FIG. 12D illustrates another version in which a magnetic ring is attached to the rotatable catheter body/spool. The ring may have bands of opposite polarity alternating around the circumference, in which the number of bands is proportional to the angular resolution. Finally, FIG. 12E illustrates another variation, in which there is optical encoding using a disc attached on-axis to the rotatable catheter body or a contiguous element (e.g., the spool). An off-axis optical read head may detect rotation of the disc.

In some variations, the device or a system for using the device incorporates a "mouse chip" position sensor similar to those used in a computer optical mouse in order to look at the catheter and encode angular and longitudinal motion. Other means of position sensing may involve an element or elements of different operating principles, such as a capacitive fingerprint sensor.

A mouse chip may look at the surface of the catheter (or the braid if the outside laminate is transparent or translucent) and on the basis of the difference in feature position between adjacent snap-shots, it calculates the X and Y motion vectors from which we may deduce rotation and/or longitudinal motion. The features being observed by the mouse image sensor can be in any shape or form, and the pattern can be regular/periodic or random. Preferably, the features are not perfectly periodical at the very least. Most preferably, the features are random. There should be at least one discernible feature within the field of view of the mouse image sensor within each successive frame. Incorporation of the chip into an access port may allow removal of the optical encoder from the device, simplifying the device. Alternatively it may allow compensation for imperfect catheter torque transmission. Rotating the proximal end of the catheter by 360 degrees does not necessarily lead to a 360 degree rotation at the distal tip, particularly if the catheter is experiencing distributed friction over its length, for example from the introducer sheath, guides, and/or tissue friction especially in a tight lesion. A significant fraction of the "wind-up" or "lag" between the rotation of the proximal and distal ends of the catheter may come from the unsupported length of catheter between the proximal handle and a Touhy-Borst hemostasis valve. By placing the mouse chip on the "wet" side of the valve, rotation and longitudinal motion of the catheter may be detected while eliminating the unsupported length effect, thereby increasing the precision of measurement.

The mouse chip output (Z, theta) can be displayed on an image display and potentially integrated into a fluoroscopy unit display, as described below. Longitudinal data in particular could be used by the surgeon to measure the length of a lesion, which would in turn guide the cut on/off positions.

Preliminary data indicates that lesions in arteries show clear eccentricity, with almost healthy tissue in one or more quadrants of the vessel transitioning into atheroma, lipid rich regions, calcium deposits etc. The data clearly underscore the need for directional therapy. Thus, the catheters described herein may be used for passage through cardiovascular vessels, and configured to image a wide angle of tissue to millimeter depths, using a single optical fiber configured as a common-path interferometer in an optical coherence tomography sensor.

Any of the catheters described may be used as part of an OCT system including an off-axis optical fiber within the rotatable catheter body. The system may include any of the elements useful for OCT imaging, such as the OCT light source, OCT detector(s) and image processors, which may also include filtering, signal correction and noise reduction.

In some variations, as mentioned above, the optical fiber may be contained within a passage or lumen of the catheter, which is positioned off-axis of the longitudinal axis of the catheter body (e.g., radially displaced from the midline of the catheter). For example, the single optical fiber may be located in a tube that runs the full length of the device. At the distal catheter end, the optical fiber may terminate in a fixed solid transparent material of particular refractive index (which is preferably mis-matched with the refractive index of the optical fiber core in a manner that provides valuable optical properties as described in U.S. patent application Ser. No. 12/790,703, Publication No. US-2010-0305452-A1 previously incorporated by reference). Rotation of the catheter body will rotate the distal end region where the optical fiber terminates. At the proximal end, the catheter body can be manually (or automatically) reciprocated/oscillated to cause the distal end to rotate around an azimuthal angle (including multiple complete rotations) while avoiding excessive fiber stress or bend losses and allowing the fiber to be contiguous from the console to the distal tip (no fiber optic rotating junction is necessary). The off-axis rotation of the fiber causes the light beam from the fiber to move through a well-defined azimuthal angle or complete rotation(s) around the vascular interior. At the proximal end, noise and image artifacts can be reduced by using a confocal pinhole optical arrangement that separates the main OCT signal transmitted by the core from any background noise transmitted by the cladding. The resulting OCT signals can be processed to produce panoramic images useful for atherectomy and other applications.

Thus, in some variations, the catheter device for optical coherence tomography (OCT) analysis of a distal target includes: a catheter body with a proximal end and a distal end; at least one off-axis optical fiber configured as a common path interferometer disposed along the length of the catheter body; at least one fiber unit having a core, a proximal face, a distal face, and cladding, said core and cladding being contiguous from the connection at the console to the distal catheter tip, and an optically transparent window near the distal end region to which the distal end of the fiber is fixed, allowing radiation to emerge from the tube and impinge on the tissue being imaged at substantially normal incidence. A system including these items may also include an optical radiation source connected at the proximal end of the catheter body by way of a nonreciprocal element and a processor, which may include an optional OCT background correction unit and a detector.

Any of the systems described herein may enable intravascular imaging to determine the extent of a disease (e.g., coronary disease) to be assessed in both the azimuthal and longitudinal positions, and may also allow the identification of disease states (calcium, lipid, atheroma, fibroatheroma). This may in turn allow the treatment to be planned, and a known depth of cut to be superimposed on the image of the disease. Longitudinal and azimuthal indexing may also allow the physician to make a precise estimate of how long a cut should be, whether to take a second cut after a first one, whether the cutting embodiment is facing the disease, and whether the catheter (e.g., cutter) is apposed to the target tissue or in physical contact and therefore more likely to make a cut. Proximal indexing of longitudinal motion coupled with disease/non-disease differentiating imaging may allow the precise length of cut to be planned and executed. This information may be coupled to an automated advancement function of the system to ensure that proximal motion correlates to distal tracking in the vessel and may help prevent the physician from cutting where a cut is not warranted. Directional imaging may allow the catheter, and specifically variations including cutters on the catheter, to be accurately aimed at and apposed to the diseased tissue. Directional imaging may also lead to unambiguous cut/no-cut signals that are difficult to make with fluoroscopy guidance alone, which may help reduce procedure times.

High resolution images of vessel wall morphologies may also be correlated to histologic analysis of excised tissue. This correlation may enable a real-time histologic review of the disease while manipulating the device in the vasculature, which may also make it possible to target specific disease states. In many of the variations of OCT imaging catheters described herein, the devices are capable of resolving an at least 2 mm imaging range that may allow at least one cutter-depths worth of warning of a potential adverse event, for example a perforation. Imaging may also permit the testing of the optimal debulking hypothesis, which proposes a correlation between the volume of diseased tissue removed from the inner lumen of the blood vessel and the long term patency of the vessel. Imaging will show precisely how much tissue has been removed, how much is left, and the treated lumen diameter.

Any of the systems described herein may include an off-axis OCT imaging catheter including a catheter handle with rotation control, cutting control, flush control, and angle/position indexing. An OCT catheter may have an optical fiber that is fixed at a distal position on the elongate catheter body (shaft) and the catheter shaft is allowed to rotate with respect to the proximal handle, although with a well defined number of turns. The optical fiber travels in an off-axis pathway down the length of the rotatable catheter body, and an optical fiber management mechanism in the handle may prevent the fiber from breaking, bending beyond the bend loss threshold, or getting tangled. For example, a single take-up spool in the handle may be used to permit a set number of turns before a physical stop is imposed. The catheter handle, including the fiber management pathway (one embodiment of which is shown in FIG. 5), typically does not require the use of a second take-up spool. The fiber management system incorporates the fiber on a single internal take-up spool. The size of the proximal handle is therefore significantly reduced, as is the complexity.

Any of the catheter devices described herein may include an encoder in the proximal mechanism that detects angle and may constantly relay this information to a processor (e.g., computer) controlling the OCT data acquisition system. The value of the angle may be incorporated into the display algorithm to show a 360 degree view of the inside of the lumen, as illustrated in FIG. 13.

Figure 13:
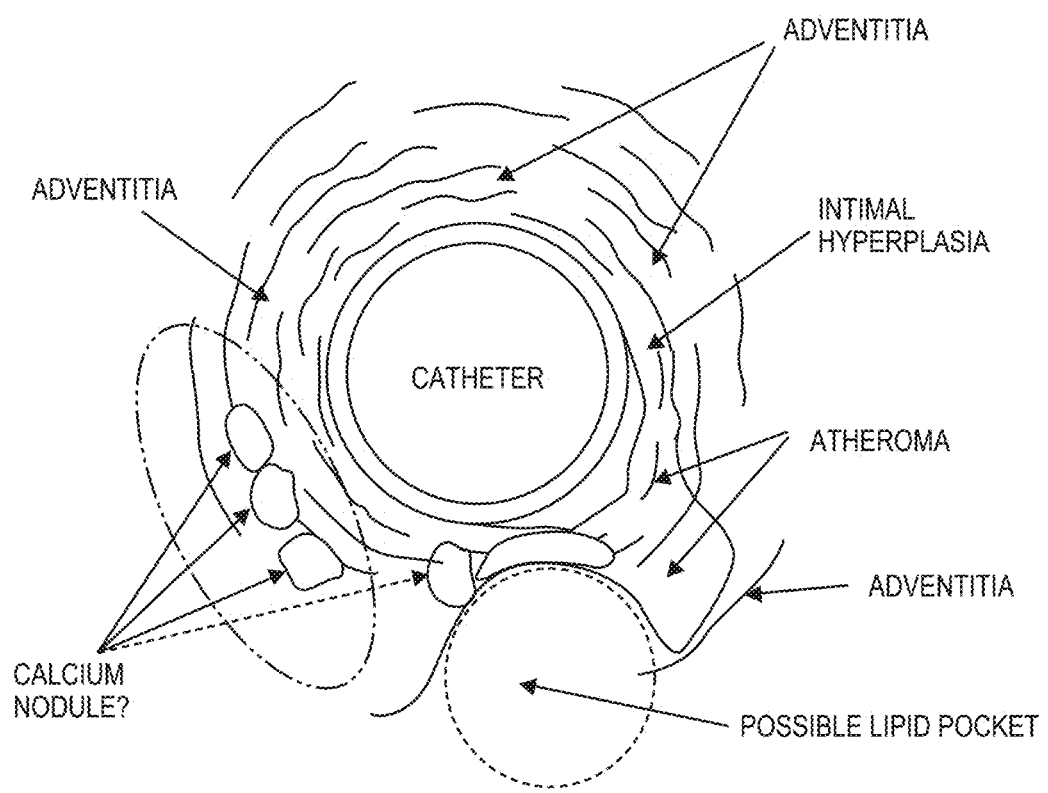
FIG. 13 illustrates one example of a toroidal (annular) display of an OCT image as described herein.

In the image example of FIG. 13, the radial line 1301 denotes the current position of the encoder. The display can be continually refreshed by rotating the catheter in either direction. The whole display can also be rotated and oriented with respect to the fluoroscopic view being acquired simultaneously in the catheter lab. For example, the image may be rotated so that the pericardium is "up" or "down" in the image display. By orienting the display and by knowing the spatial relationship between the cutter position and the display (and by implication, the critical physiological structures in the vessel), the physician may orient the cutter on the device to cut in a safe manner. In the exemplary display shown in FIG. 13, the image is labeled to indicate exemplary structures that may be distinguished by the OCT catheter devices and systems, when used in the vasculature. In addition, as described in more detail below, the image indicates the presence and location of the catheter relative to the surrounding tissue, resulting in an annular display that may accurately reflect the location and orientation of the catheter relative to the tissue.

As can be seen from the above, having a relatively large catheter inside the vessel and having the imaging element disposed on the circumference of this catheter is advantageous as it brings the imaging element into close proximity to the tissue being imaged. There is not a lot of "wasted" imaging distance in the lumen where there would normally be blood. This feature in turn maximizes the imaging range of common path interferometry and reduces the volume of blood to be displaced or trans-illuminated. The catheters in the embodiment have demonstrated an ability to "see" through several hundred microns of blood, significantly better than contemporary designs. It also enables a representative "size" picture of the internal artery structure to be presented. There is little or no NURD—non-uniform rotational distortion—as a result of the relatively large torque shaft having excellent torque transmission properties. This aspect is crucial for accurate cutter guidance (sizing up lesions in both depth and azimuthal extent).

The imaging and image processing using the off-axis OCT catheters described above is discussed in greater detail below.

Figure 14A:
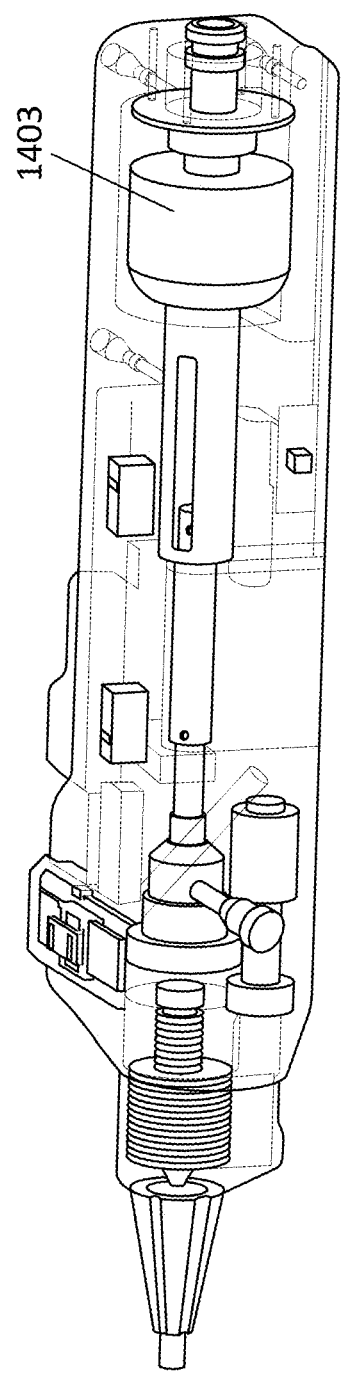
FIG. 14A shows a transparent view of one example of a catheter handle including a motor for rotating the catheter body.
Figure 14B:
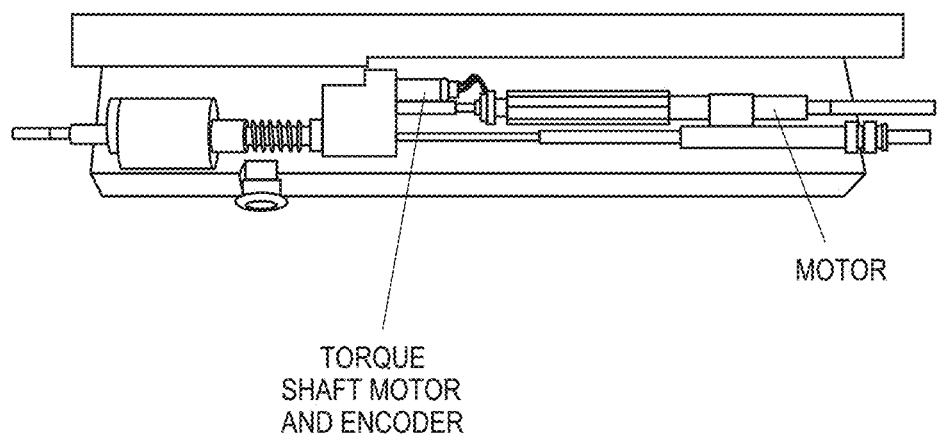
FIG. 14B is a partially opened view of another example of a catheter handle including a motor and a fiber management system.

Alternative variations of the catheters described above may include a motor driving the rotation of the catheter body, and/or the advancement of the catheter longitudinally. For example, a controller can be automated with a motor to drive the rotation of the catheter. Such a controller may be within the handle, or external to the handle. A motorized drive may provide a controlled sector sweep of the imaging element. For example, FIGS. 14A-14B illustrate one variation of a handle having a motor.

Part II: OCT Signal Processing

The OCT images collected by the devices and systems may be displayed in any appropriate manner. For example, the OCT images may be displayed as an "azimuthal view" similar to that shown in the example of FIG. 13, or as a "waterfall view" showing linear scanning from the "one dimensional" OCT scanner at the distal end region of the catheter, or both. Although in the variations described above the OCT imaging scanner (the end of the optical fiber) is shown as near or at the distal end of the catheter, facing perpendicular to the catheter, the OCT imaging scanner may be positioned at any appropriate region of the catheter, including more proximally located positions, and may be oriented more forward-facing or backward-facing (e.g., at a non-90° angle relative to the wall of the catheter).

Images from the catheter can be rendered on the display(s) such that the image remains stationary and a virtual imager position indicates which direction the scanner is pointing around the perimeter of the catheter. This method of rendering the image may be intuitive, providing the sense that the "top" of the image corresponds to the "top" of the vessel or lumen being imaged. In practice, the orientation of the distal end of the catheter may be uncorrelated to the actual "top" or "bottom" of the distal end of the catheter relative to the patient, or it may be correlated.

As an alternate method of rendering the azimuthal image, the system can maintain the virtual imager position in one place (i.e. the "top" of the screen) and rotate the entire image as it is constructed. In a device with a coincident imager and cutter, this may have the advantage of having the cutter always in the "up" position. This view is more akin to riding along with the device and seeing what it would see while in the vessel. In some variations, a pseudo image or marked region may indicate the presence of a cutter or other region or device(s) associated with the catheter near the imaging region.

In some variations of the systems described herein, additional positional or status information on the system may also be displayed in addition to (or alternatively to) the azimuthal and/or waterfall displays of OCT data. For example, in some variations the system may provide information on the longitudinal position or movement of the distal end of the catheter. Movement of the catheter forward/backwards may be represented by a representation of OCT data versus axial distance (e.g., forward/backwards) as the device is moved axially. A similar axial lag (akin to the rotational lag issue mentioned above) may also result, and similar correction methods may be applied.

Lag is a typical problem in rotational catheter system such as those described here. Since a catheter is not an ideal torque transmitting entity, there will be some phase delay ($\theta$) for which the distal end of the catheter does not rotate when the proximal end of the catheter is rotated. This phase delay can cause incorrect orientation of the image when the direction of rotation changes, as well as a smeared sector within the image, and frustration for a user. If the angle $\theta$ can be determined, however, the system can keep track of the current position and direction of travel and account for the phase delay when changing directions. Various methods of determining $\theta$ to allow for proper orientation of the image will be discussed herein.

Figure 15:
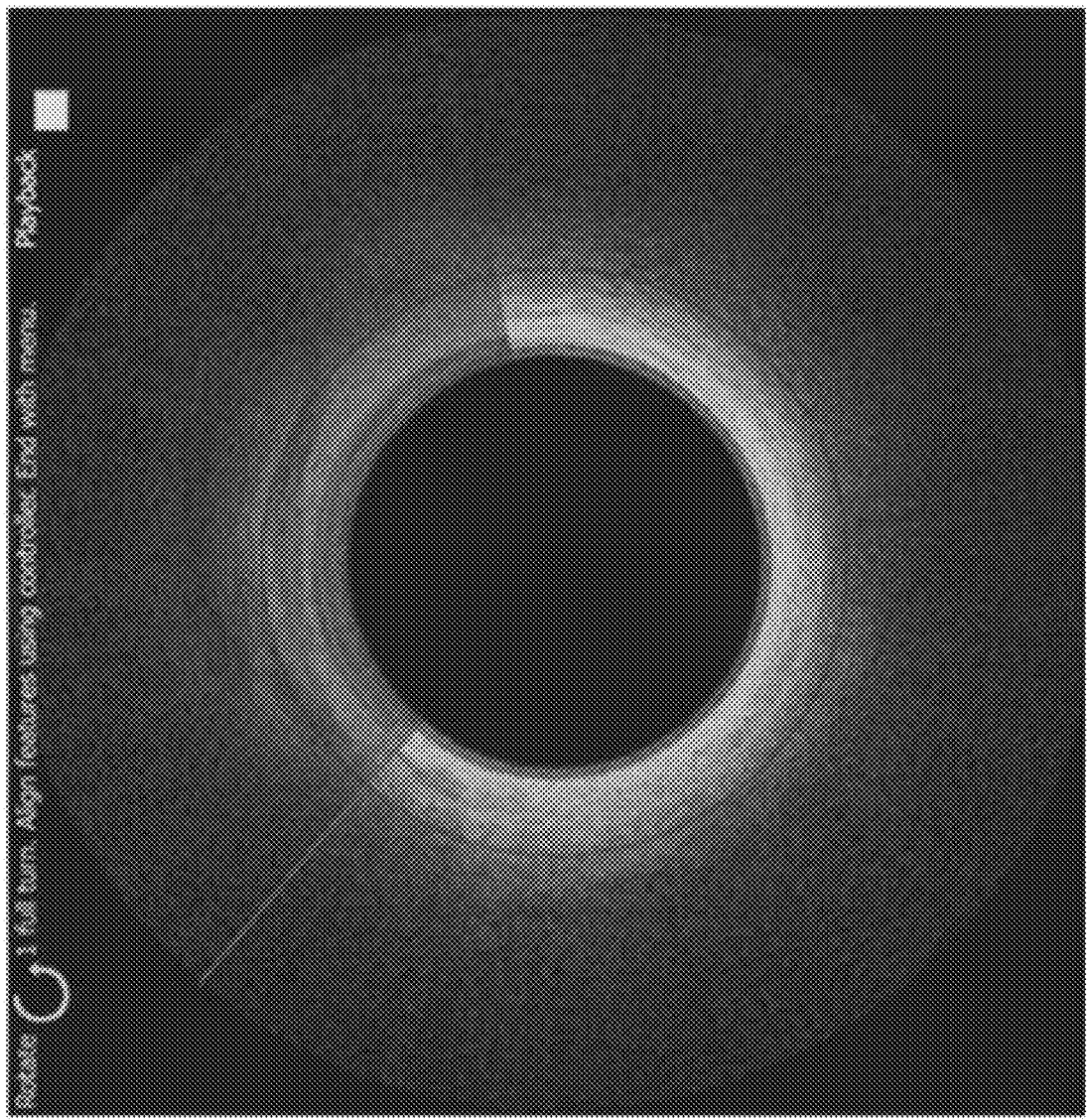
FIG. 15 illustrates a method of determining the proper orientation of a scan image when the direction of rotation changes.
Figure 24:
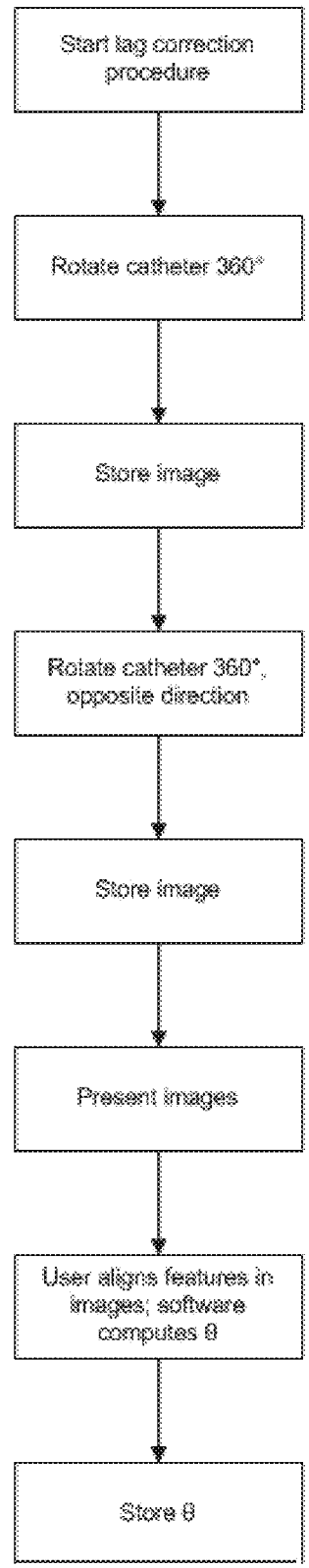
FIG. 24 schematically illustrates one method of determining a lag-correction angle, θ.

One method of determining $\theta$ can be referred to as the "overlay" or "side-by-side" mode. In this method, the operator can take one complete rotational scan within the vessel or lumen to be imaged, preferably in a zone with a visible anatomical feature or fiducial mark. The operator can then take a complete rotational scan in the opposite direction at the same physical location. The processor (e.g., logic, such as hardware, software or firmware) then overlays the two images or presents them side-by-side on the display(s). The operator can align the two images by rotating the image using the user interface, which should differ in angle by $\theta$. Once the images are aligned, the software can store $\theta$ and use that transparently in subsequent scans to correct the image. This method is illustrated in FIG. 15. In FIG. 15, the azimuthal display shows a radially extending line (upper left) indicating the orientation of the sensor. Overlays of the two images (each of which may be partially transparent with respect to each other) may be manually or automatically performed. A schematic of this method is outlined in FIG. 24.

Another method of correcting for lag uses a fluoroscope or other real-time view of the distal end of the catheter as a guide to determine when torque has been fully transmitted down the shaft. A schematic of this method is outlined in FIG. 25. The catheter body can be rotated until motion is seen on the real-time view. The operator (or an automatic system) can then prepare to determine $\theta$. The catheter body can then be rotated in the opposing direction until motion is again seen or detected on the real-time view. In some variations, the operator then informs the system that the determination is finished. Alternatively, the system may automatically determine this. The difference in angle at the proximal end from the time the procedure started to the time the operator ended it is $\theta$.

Yet another method of determining and/or correcting for lag automates the procedure by detecting motion from scan to scan. If, for example, the catheter is not rotating due to torque build-up, each single line scan should differ from the next by a small value. Using the difference of squares method, or other suitable image comparison algorithm, the system can distinguish motion from non-motion and hence not update the rotational reconstruction of the image while the distal tip is not moving.

Figures 16A, 16B:
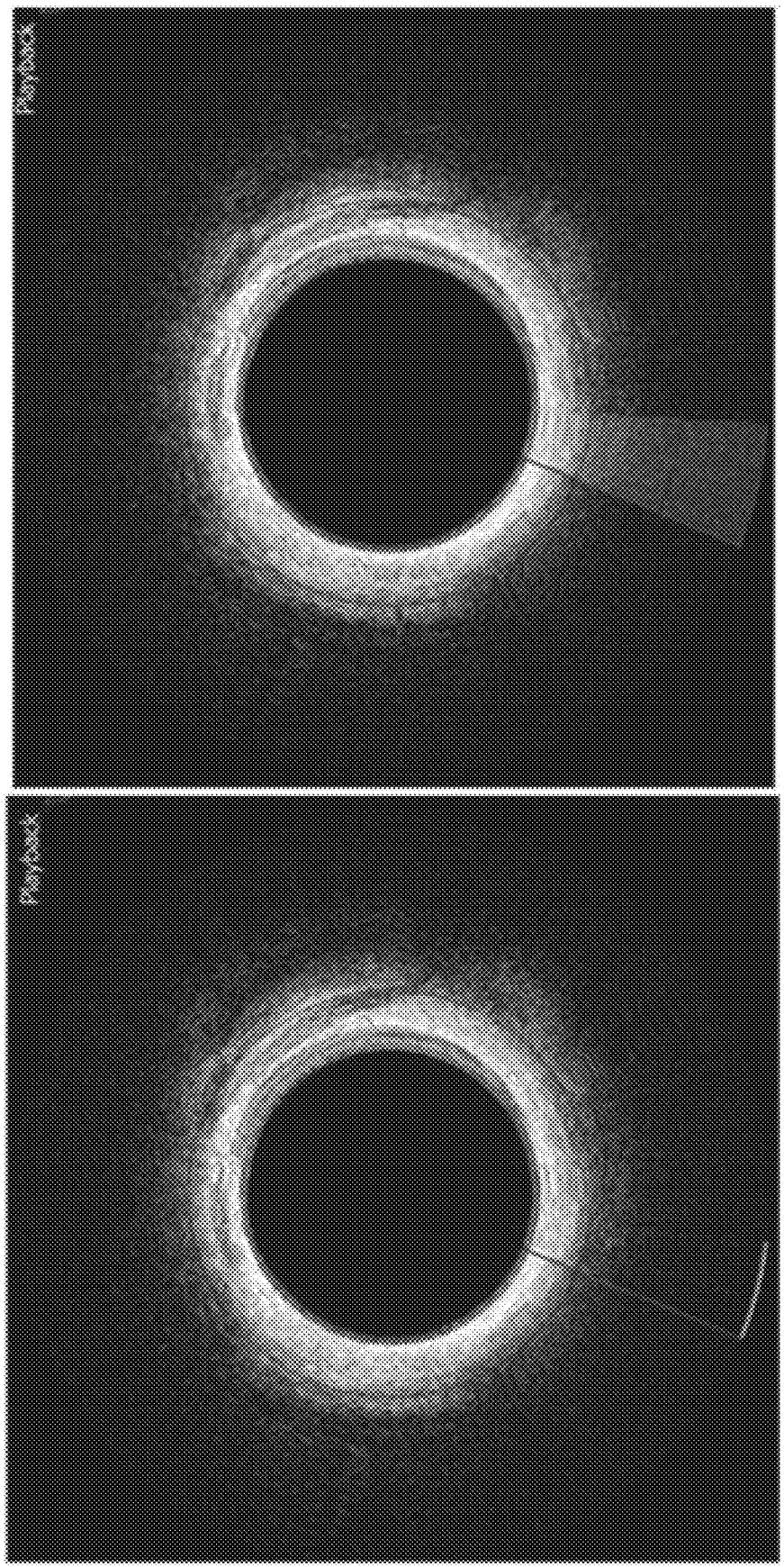
FIGS. 16A-16B illustrate various methods for showing when phase delay compensation is occurring.
Figures 25, 26:
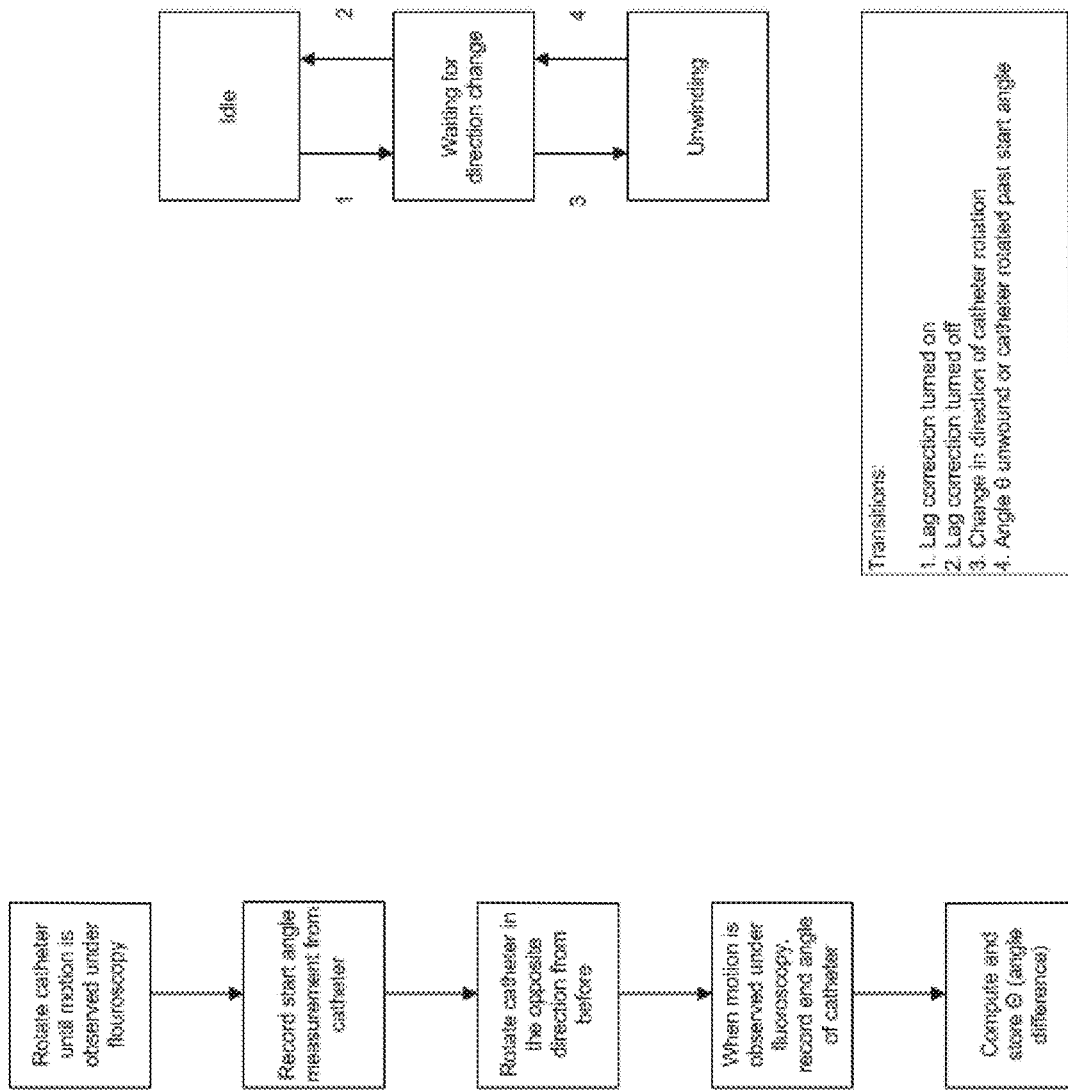
FIG. 25 schematically illustrates another method of determining a lag-correction angle, θ.
FIG. 26 schematically illustrates a method of indicating lag correction.

All of the above methods can be accompanied by user interface elements that indicate when compensation for $\theta$ is occurring. As shown in FIG. 16A, an arc can be displayed along the outside of the sector image. As shown in FIG. 16B, a transparent wedge indicating how much $\theta$ remains can be displayed. These methods may or may not include fading, hysteresis, and other means to remove unnecessary distraction from the user while still conveying that windup is being removed instead of active imaging. FIG. 26 show a schematic illustration of this method. The lag correction methods described herein are of particular interest in the off-axis OCT catheters described herein because both the catheter and the optical fiber (producing the OCT image) are being rotated.

Figure 17:
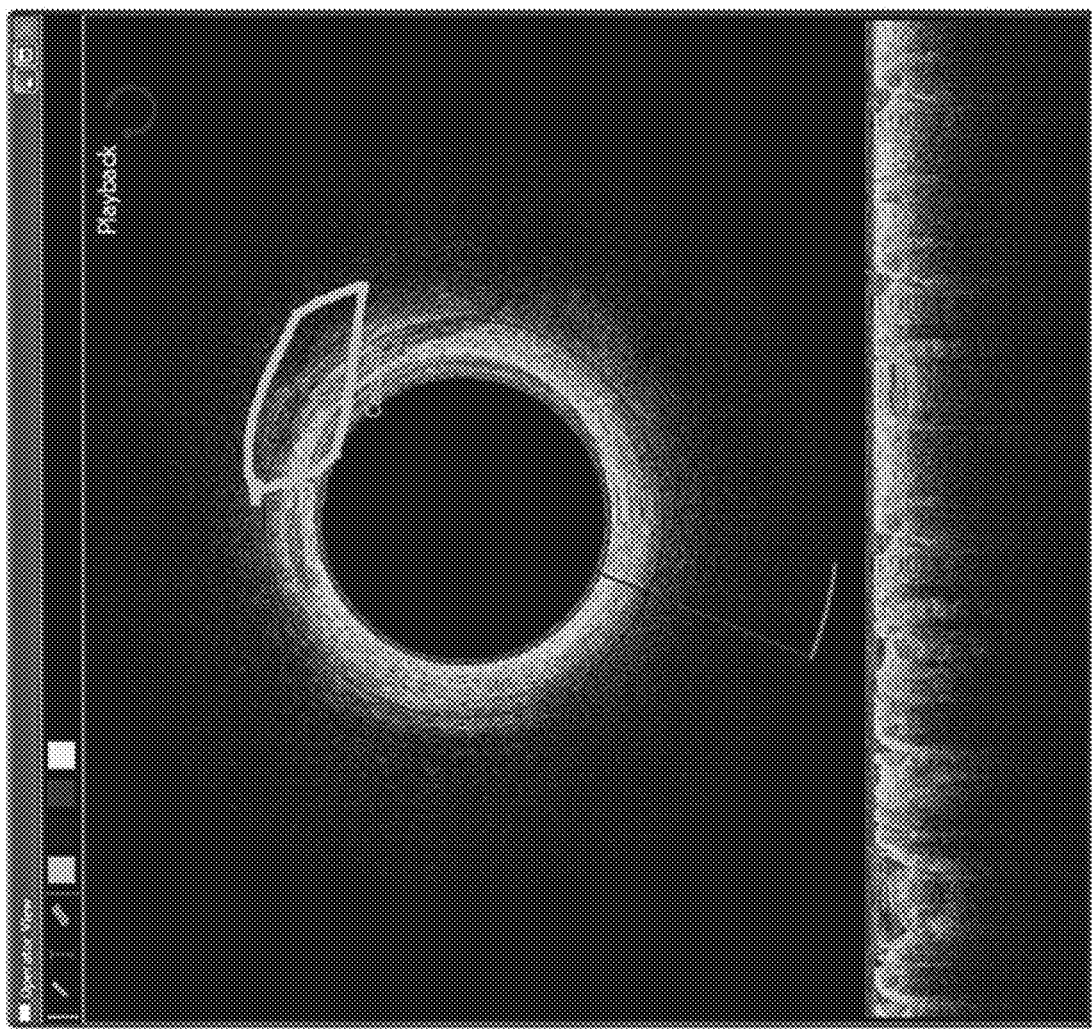
FIG. 17 shows notes and illustrations overlaid on a sector image.
Figure 18:
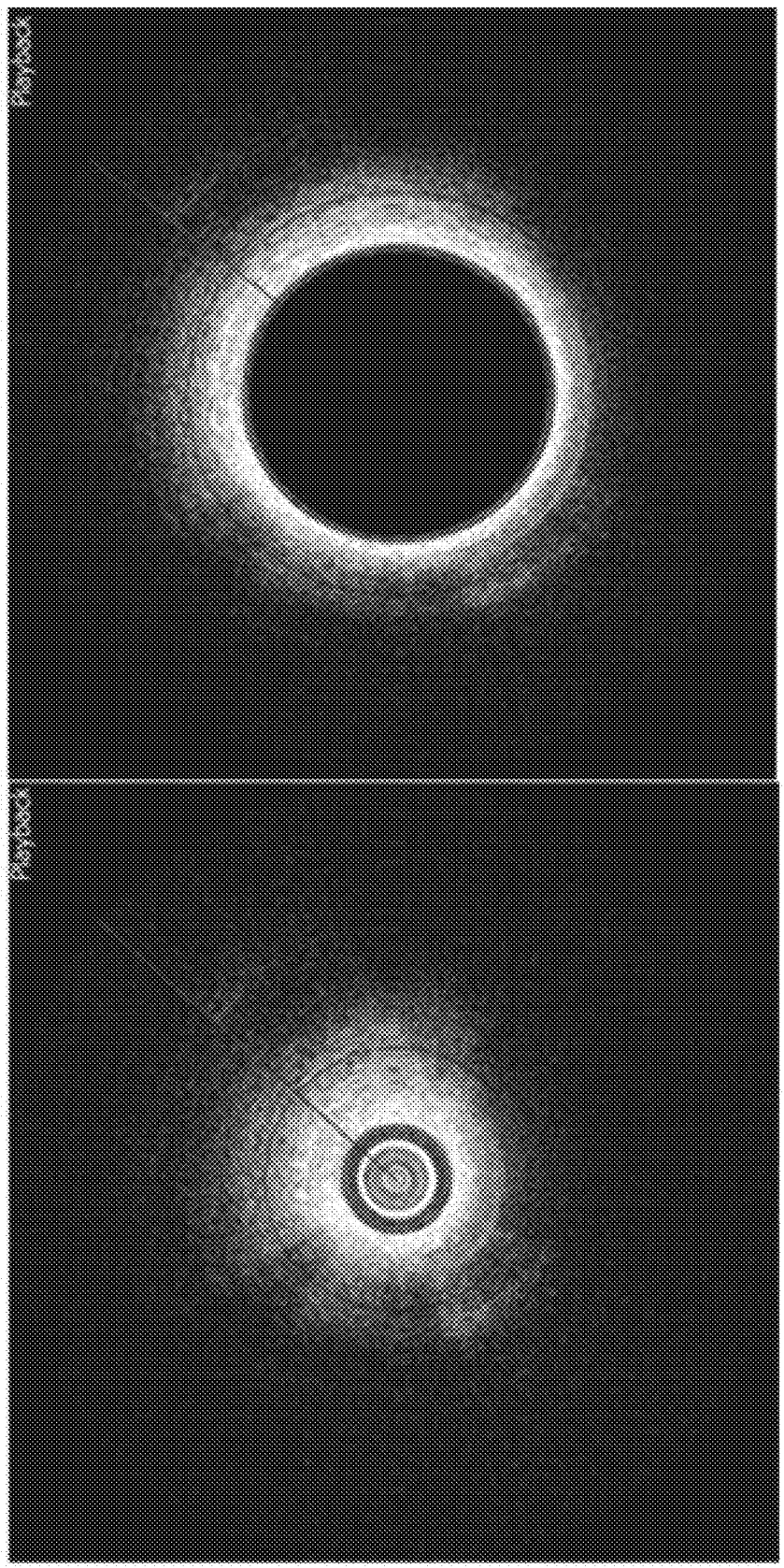
FIGS. 18A-18B illustrate one method of image distortion correction.

As described above, real time imaging information from the catheter can be displayed for the operator. In some embodiments, a substantial proportion of interaction with the system is performed by a technician, and the operator (e.g., physician) is most often a consumer of the data on the display. The technician can annotate the physician's screen image with text and/or simple graphics in a non-destructive way that does not distract from the images on display. FIG. 17 illustrates one example of notes and illustrations that can be overlaid onto the image on display. This may allow the technician to highlight regions of interest, such as anatomy, diseases, etc., in real-time, discuss treatment with the physician, and allow for clearing or storing of the annotations for later review. This could also be useful for other experts outside the sterile field to interact in a precise graphical way with the operating physician.

Because the imaging system described herein is a manual scan device, allowing arbitrary angle positions and sweep ranges, old data may sometime appear on screen if the operator does not scan over previously visited positions. One method for reducing confusion and enhancing the focus on new data is to gradually fade old on-screen image data based either on motion (the more scanning the operator does, the faster the images fade) or on strict time. This highlights the newest data, as it always appears with maximum brightness and opacity, while allowing the old data to still be visible, but easily distinguished.

Depending on the current activity being performed by the physician (i.e. cutting, rotating, etc.) various portions of the data display have different significance. For example, when cutting it may be more advantageous to focus on the "waterfall" (time vs. depth) display. When targeting, it can be more useful to focus on the sector (two dimensional azimuthal) display. Using a variety of sensors, the system can deduce the action and automatically highlight or enlarge the appropriate display for the situation. When cutter actuation is detected the waterfall portion of the display can be enlarged and the sector display can be reduced, for example. These different displays may be advantageous because they may optimally allow a users own natural edge-detection to discern features from the otherwise one-dimensional information. In some variations, additional signal processing may also be applied to detect or determine features from these OCT images. For example, tissue boundaries may be determine or detected, and indicated on one or more of the displays.

The systems described herein may also automatically or manually toggle between the one or more display types, or may emphasize one or more of the display types. For example, if the system is being used to modify tissue (e.g., cut tissue using an atherectomy element), the waterfall display (which may more easily allow detection of the tissue boundaries) may be enhanced by showing it larger than the azimuthal display, or by showing just the waterfall display. This may be done automatically if the controller indicates that the user will be (or is) using the atherectomy element(s), or it may be done manually before the user selects it.

When displaying the OCT data, the system described herein may correct for various sources of error. For example, one source of error arises because the sensor (OCT imager) is positioned at the outer edge of a rotating catheter. A naïve rendering implementation might draw the sector image from the very center outward (e.g., so that the azimuthal display is more of a circle than a toroid). This depiction would, however, be completely artificial, and result in the features toward the center appearing pinched. While this distortion has no impact on the assessment of depth of features, any decisions based on morphology in the azimuthal direction could be effected by the resulting underestimation of their size. Since the catheters used herein have a known diameter and image position, the system can take this into account when rendering by remapping the origin of the polar coordinates to a new radius and scaling the entire image to fit within the field of view of the display. This ensures that tissue morphology is correctly represented. FIG. 18A represents an uncorrected image, and FIG. 18B illustrates the same image after correction for the diameter of the catheter (or radial position of the OCT sensor relative to the catheter central axis). In other embodiments, the exact imager position can be encoded into an RFID or other non-volatile memory associated with the catheter to automate the configuration.

Figure 27A:
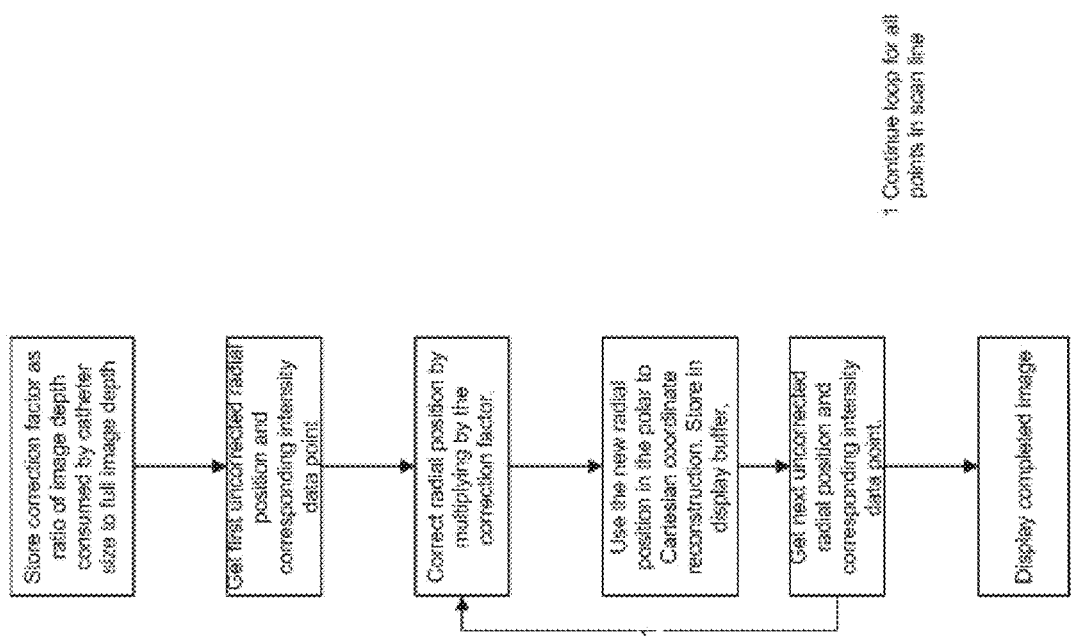
FIG. 27A-C schematically illustrate various methods for correcting the image to adjust the scaling.
Figure 27B:
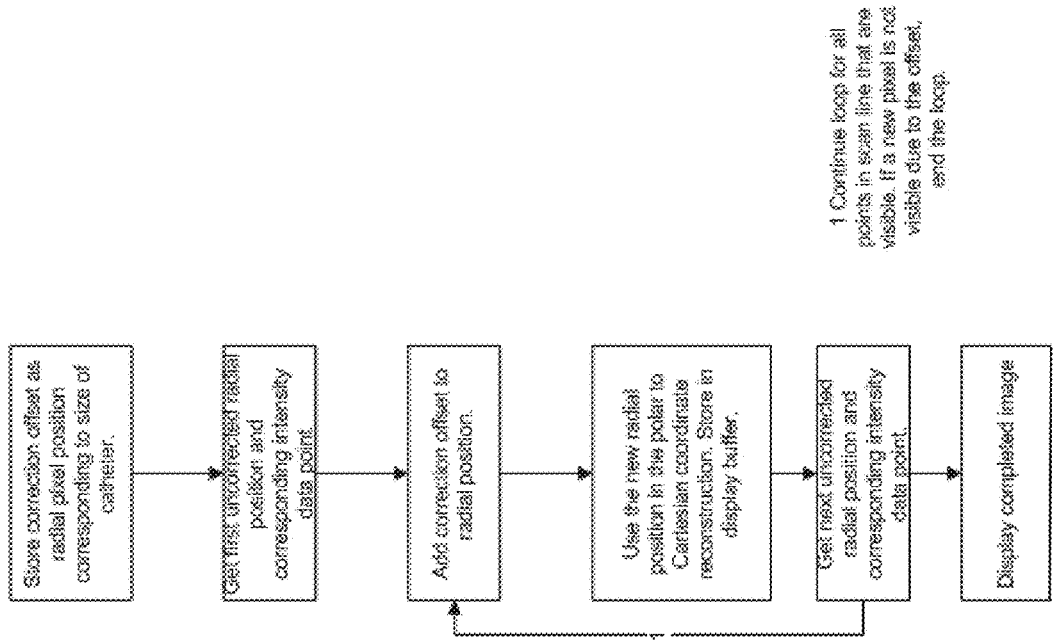
Figure 27C:
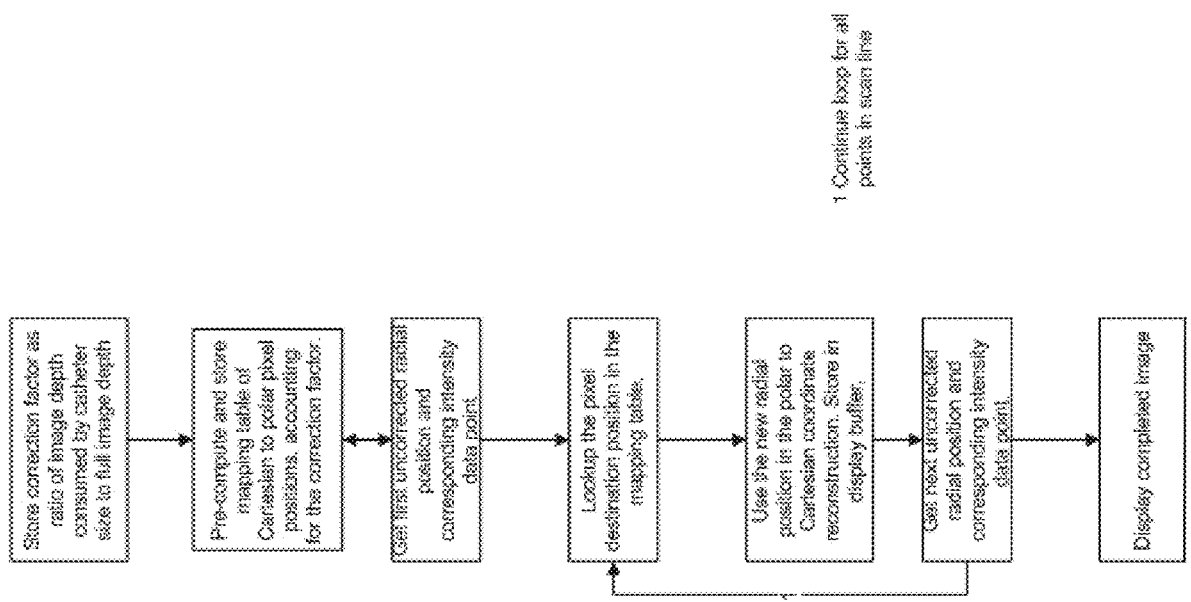

A second source of error may arise in the scanning system. It is possible that the depth vs. sample number mapping could be nonlinear, resulting in some radial distortion in the image. By characterizing each system at manufacturing time, a mapping of sample number to depth can be constructed and the system can correct for any non-linearity during rendering. FIGS. 27A-27C schematically illustrate various methods for correcting the image to adjust the scaling as described above.

Overlaying an artificial indicator at a fixed depth from a tissue interface would enable pre and post-cut depth evaluation, comparison of normal healthy tissue morphology to actual image appearance, and possibly other applications.

Figure 19:
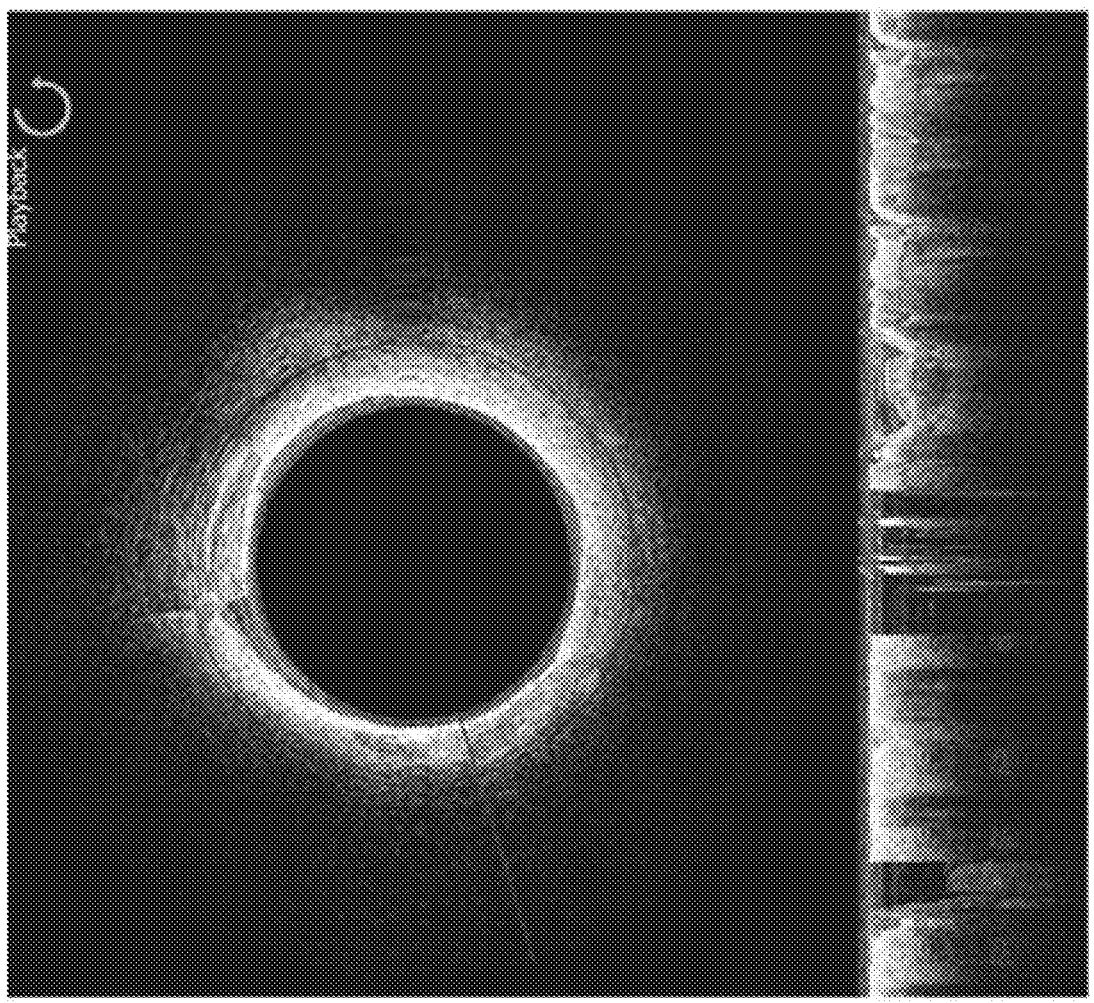
FIG. 19 illustrates an indicator superimposed over the image corresponding to a desired tissue depth to be monitored.
Figure 20:
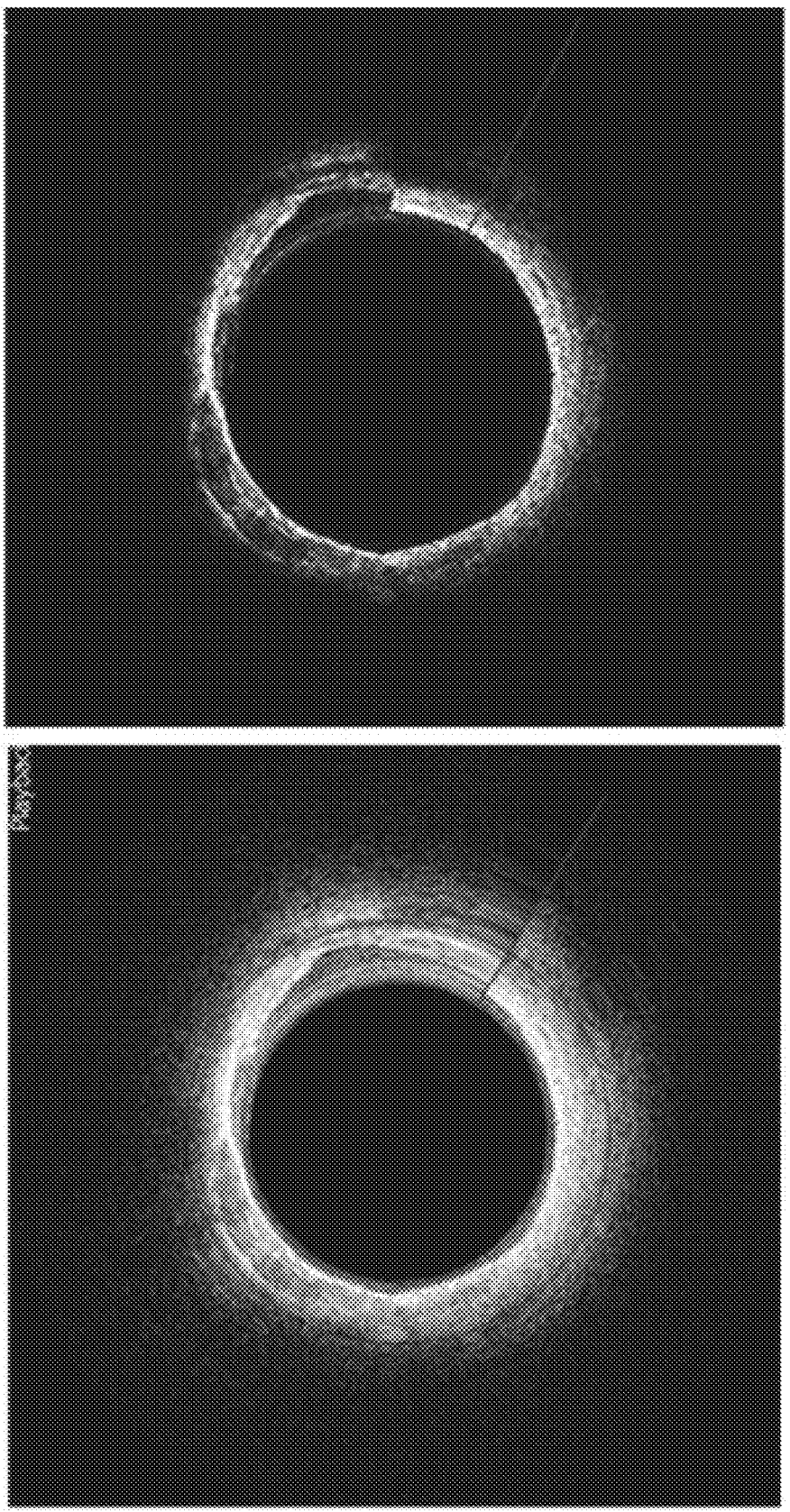
FIG. 20A illustrates a normal image and FIG. 20B illustrates the same image after applying an aggressive contrast stretch technique to enhance the image.

As mentioned above, a software approach can be implemented that detects tissue boundaries (and particularly the intimal boundary of a blood vessel) by searching each scan line for a sharp peak in the first portion of the scan. Each peak position can be averaged together to reduce noise. Those averaged values can then be added to a fixed configurable offset (indicating cutter depth, statistical average media depth, etc.) and an indicator can superimposed on the image at that new position. FIG. 19 illustrates an indicator superimposed over the image corresponding to a desired tissue depth to be monitored. It can be seen from FIG. 19 that the depth indicator is superimposed on both the sector scan image (the top image in FIG. 19) and the waterfall image (the bottom image in FIG. 19).

Visualizing the adventitia is one key to a successful outcome in image guided atherectomy. It can be difficult in some instances to distinguish from noise or other layers, depending on image quality. Using image processing techniques, it is possible to enhance the visibility of the layer structure, making the adventitia easier to pick out.

Figure 21:
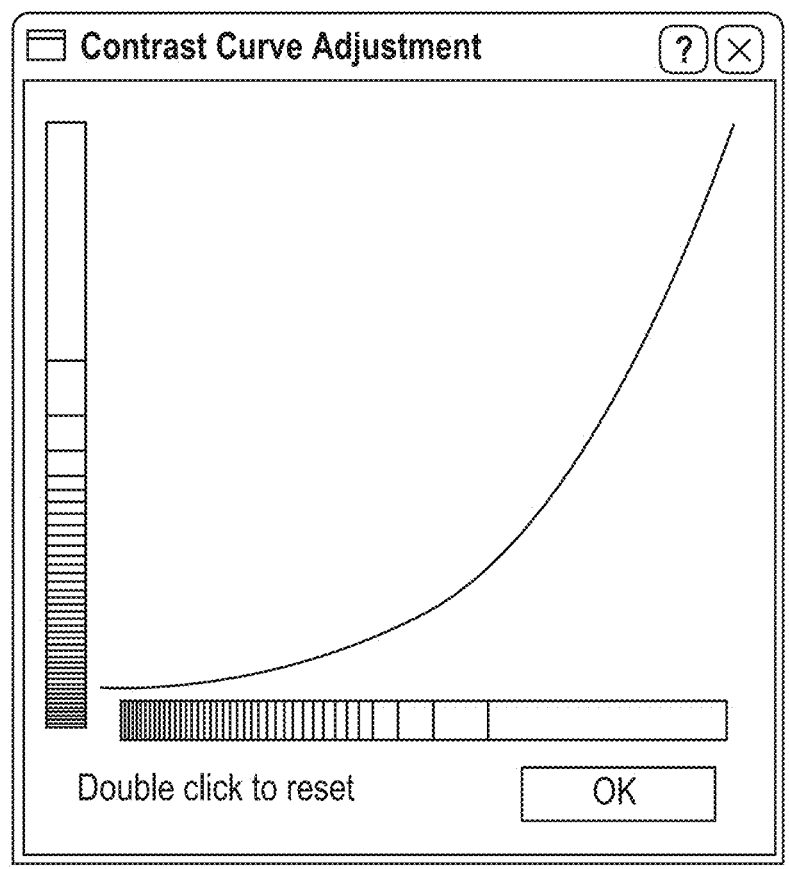
FIG. 21 shows the contrast curve used to achieve the contrast stretched image of FIG. 20B.

One method for enhancing the image uses a non-linear contrast stretch to "pull-apart" layers of different reflectivity. The operator can adjust the mapping of input gray level to output gray level in a way that emphasizes small differences in intensities. FIG. 20A illustrates a normal image and FIG. 20B illustrates the same image after applying an aggressive contrast stretch technique to enhance the image. FIG. 21 shows the contrast curve used to achieve the contrast stretched image of FIG. 20B.

Figure 22:
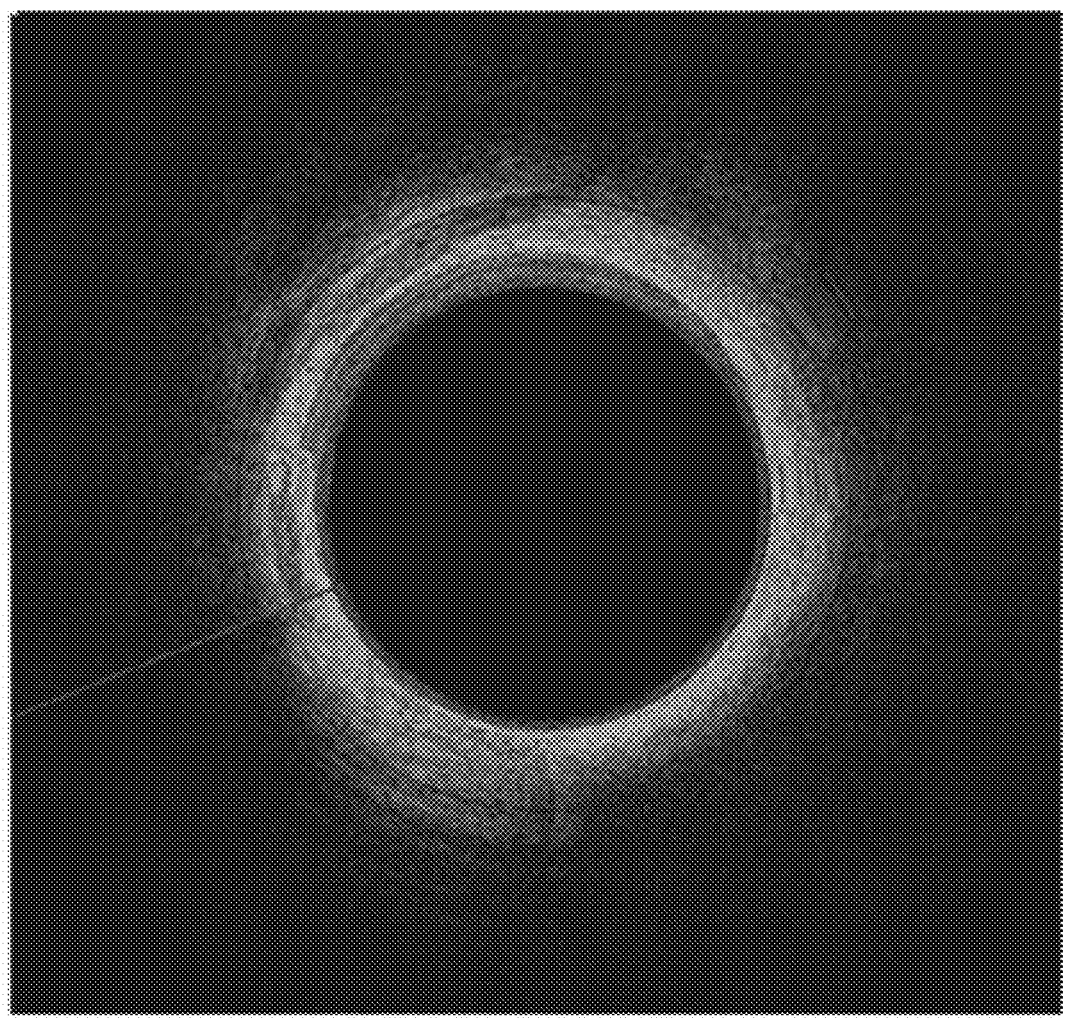
FIG. 22 shows a scan image where the bright layers have been highlighted.

Another method for enhancing the image attempts to detect the layer structure directly and overlay or highlight "bright" layers by overlaying a color or other transparent indicator on the image. The difference of Gaussian's approach can be used to find bright layers. Once the image has been processed to find layers, it can be superimposed over the raw image in a new transparent color. FIG. 22 shows an image where the bright layers have been highlighted.

Figure 23:
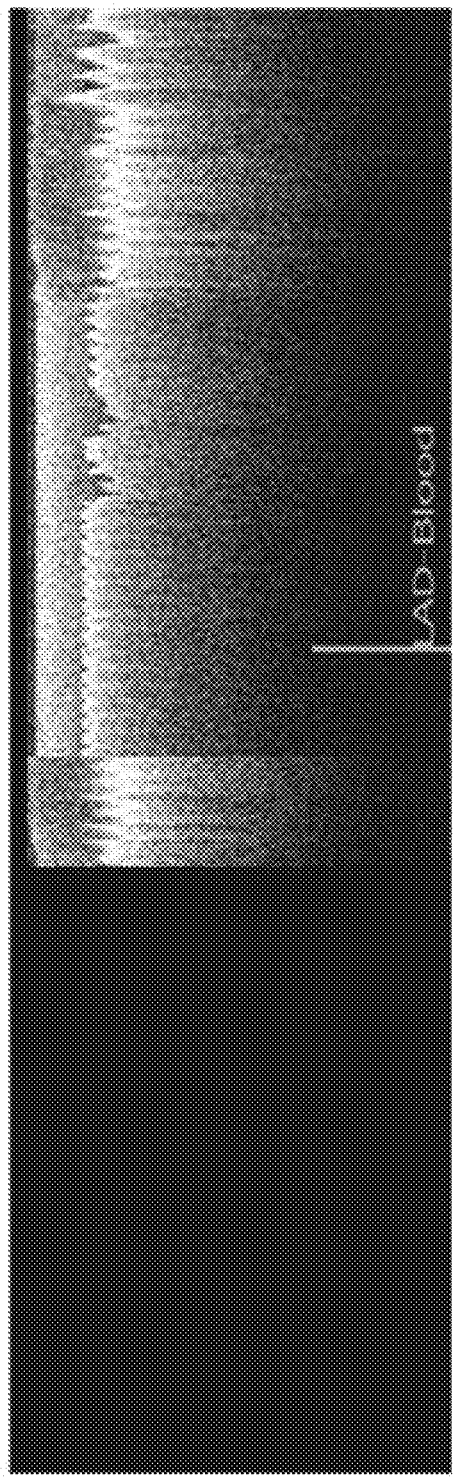
FIG. 23 shows a waterfall image superimposed with tag information.

In some embodiments, when an event takes place (such as a capture, cutter activation, lag calibration, etc.) the system can automatically store in a meta-data file the time and type of event. In addition, the tag information can be superimposed on the waterfall (time vs. depth) display. This allows real-time marking of disease structure, cut starts and ends, and other events. FIG. 23 shows a waterfall image superimposed with tag information. As the events are stored on disk, they will appear on the waterfall during playback, providing easier interpretation of the display.

Figure 28:
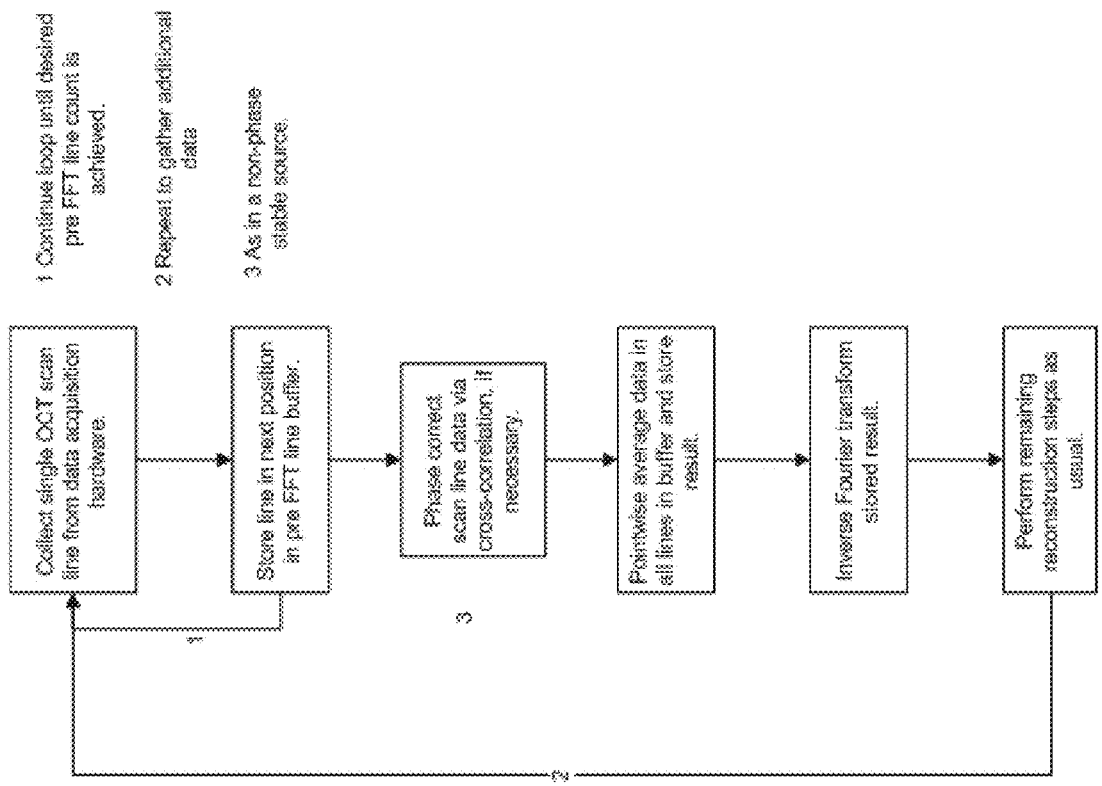
FIG. 28 schematically illustrates a method for reducing noise by FFT averaging of the signal(s).

Other methods for improving image quality will now be discussed. Given a very phase stable laser as part of the imaging system, it is possible to average several immediately consecutive line scans prior to the inverse Fourier transform. Empirical results suggest that this lowers the noise floor without impacting the signal level. If the laser is not phase stable, or if the lines differ in phase from some other source (high-speed motion, for example), destructive interference may occur which could impact the signal level. A mitigation of this effect can be performed by cross-correlating or otherwise differencing the consecutive lines to evaluate similarity. Lines which differ too greatly from the other in the averaging set could be discarded so as not to impinge on the final result. The effect of this averaging procedure is to virtually increase the laser power without actually delivering more power to the tissue. FIG. 28 schematically illustrates one variation of a method for reducing noise by FFT averaging of the signal(s).

Figure 29:
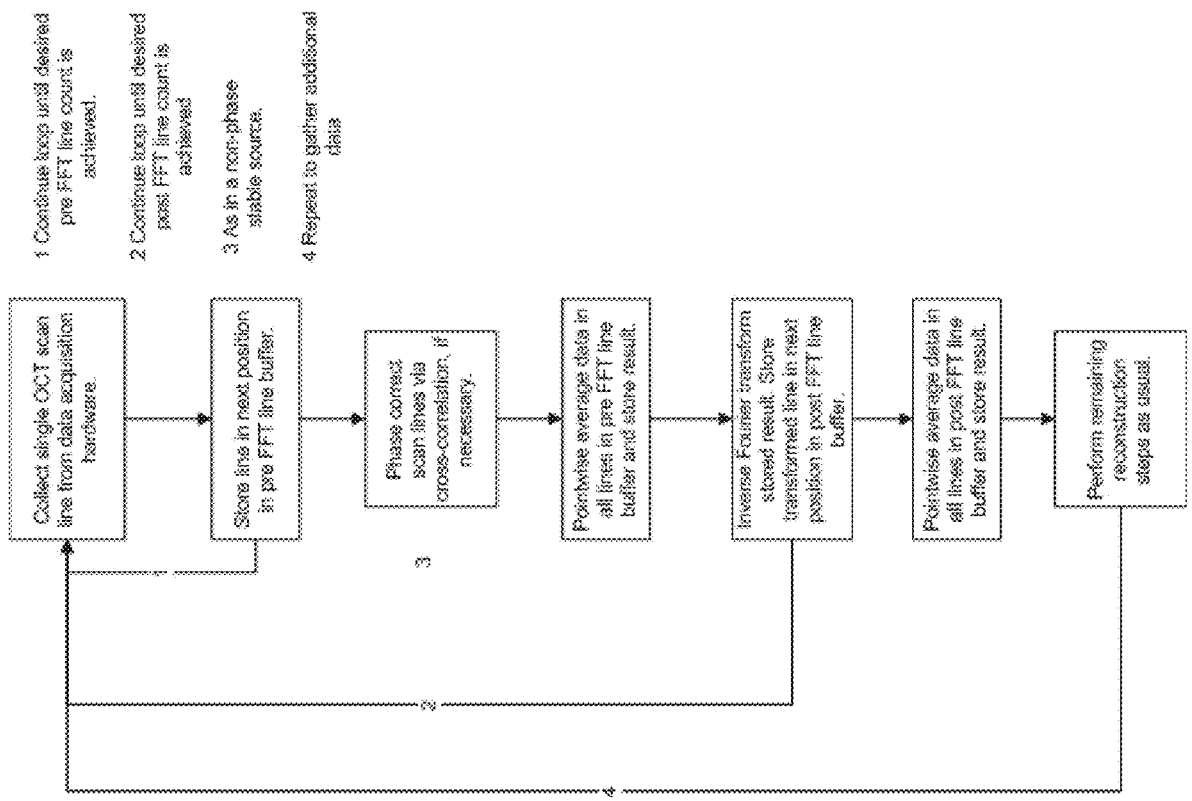
FIG. 29 schematically illustrates one variation of the post-FFT averaging method.

In an alternative embodiment related to the averaging procedure discussed above, several of the averaged line results can be bundled together and further averaged together after the transform. This has the empirical effect of reducing speckle noise in the image. This procedure is more computationally intense, and may slow the effective scan rate more dramatically than averaging consecutive line scans alone. Post-FFT averaging has no requirement for phase stability however, as it is performed in the intensity domain. High-speed motion may produce blurring, but not destructive interference effects. FIG. 29 outlines one variation of the post-FFT averaging method described above.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of imaging a body lumen with Optical Coherence Tomography (OCT), the method comprising:
    inserting an elongate catheter into the body lumen, the elongate catheter having a distal portion comprising a cutter and an OCT sensor, wherein the OCT sensor includes an optical fiber that extends through a central lumen of the catheter along a path that is off-axis of a length of the catheter, wherein a distal end of the optical fiber is fixedly attached to a distal end region of the catheter;
    rotating the cutter and the distal end of the optical fiber while acquiring OCT images of the body lumen, wherein a proximal portion of the optical fiber is allowed to wind helically within a proximal handle of the catheter during gathering of the OCT images;
    displaying the OCT images as a toroidal mapping in which the OCT images are displayed around a center region corresponding to a location of the elongate catheter;
    steering the elongate catheter towards an identified region of the body lumen based upon the toroidal mapping; and
    cutting tissue or plaque at the identified region with the cutter.

2. The method of claim 1, wherein displaying the OCT images comprises determining the toroidal mapping based on a radial position of the OCT sensor relative to a central axis of the elongate catheter.

3. The method of claim 1, further comprising correcting radial distortion in the OCT images by scaling the OCT images.

4. The method of claim 1, further comprising correcting radial distortion in the OCT images by multiplying radial positions of the OCT sensor by a correction factor.

5. The method of claim 1, further comprising correcting radial distortion in the OCT images by adding a correction offset to radial positions of the OCT sensor.

6. The method of claim 1, further comprising correcting radial distortion in the OCT images by applying a mapping table of correction offsets to radial positions of the OCT sensor.

7. The method of claim 1, further comprising monitoring a cut progression and depth in real time using the OCT images.

8. The method of claim 1, wherein the elongate catheter comprises a directional atherectomy catheter.

9. The method of claim 1, further comprising collecting the cut tissue or plaque in an internal storage of the elongate catheter.

10. The method of claim 1, further comprising providing fluid across the OCT sensor while rotating the OCT sensor.

11. The method of claim 1, wherein acquiring the OCT images comprises:
    acquiring a first plurality of OCT scan lines using the OCT sensor;
    point-wise averaging of data in the first plurality of OCT scan lines; and
    transforming the averaged data in the first plurality of OCT scan lines by Inverse Fourier Transform.

12. The method of claim 11, further comprising repeating the steps of acquiring, point-wise averaging and transforming for multiple pluralities of OCT scan lines.

13. The method of claim 12, further comprising point-wise averaging of the multiple pluralities of OCT scan lines to post-FFT average the OCT image.

14. The method of claim 1, wherein acquiring the OCT images comprises acquiring the OCT images using a lens that is positioned so as to face radially outwards relative to a longitudinal axis of the elongate catheter.

15. The method of claim 1, wherein rotating the cutter and the distal end of the optical fiber comprises simultaneously rotating the distal portion of the elongate catheter.

16. The method of claim 1, wherein the proximal handle includes an encoder that encodes rotational position information of a side-facing window of the catheter.

17. The method of claim 1, wherein displaying the OCT images comprises displaying an indicator indicating an orientation of the OCT sensor.

18. The method of claim 1, further comprising determining a phase delay by determining differences between the OCT images generated by rotating the catheter in opposing directions, acquiring a real-time view of the distal portion of the catheter as it rotates, or distinguishing motion from non-motion from scan to scan.

19. The method of claim 1, wherein the proximal portion of the optical fiber is allowed to wind and unwind as the catheter is rotated in clockwise and counterclockwise directions.

\* \* \* \* \*